(12) United States Patent
Ochoa et al.

(10) Patent No.: US 9,359,643 B2
(45) Date of Patent: Jun. 7, 2016

(54) DISCRIMINATION OF BLOOD TYPE VARIANTS

(71) Applicant: Progenika Biopharma S.A., Derio (ES)

(72) Inventors: Jorge Ochoa, Derio (ES); Monica Lopez, Derio (ES); Araitz Molano, Derio (ES); Diego Tejedor, Derio (ES); Antonio Martinez, Derio (ES)

(73) Assignee: Progenika Biopharma S.A., Derio (ES)

( * ) Notice: Subject to any disclaimer, the term of this patent is extended or adjusted under 35 U.S.C. 154(b) by 52 days.

(21) Appl. No.: 13/791,284

(22) Filed: Mar. 8, 2013

(65) Prior Publication Data

US 2014/0255923 A1 Sep. 11, 2014

(51) Int. Cl.

| C12Q 1/68 | (2006.01) |
|---|---|
| C12P 19/34 | (2006.01) |
| C07H 21/02 | (2006.01) |
| C07H 21/04 | (2006.01) |

(52) U.S. Cl.
CPC .......... *C12Q 1/6881* (2013.01); *C12Q 2600/156* (2013.01)

(58) Field of Classification Search
None
See application file for complete search history.

(56) References Cited

U.S. PATENT DOCUMENTS

2012/0172239 A1   7/2012   Ochoa et al.

FOREIGN PATENT DOCUMENTS

| EP | 1780217 | 5/2007 |
|---|---|---|
| EP | 2471949 | 7/2012 |
| WO | WO 01/77384 | 10/2001 |
| WO | WO 02/38594 | 5/2002 |
| WO | WO 2012/171990 | 12/2012 |

OTHER PUBLICATIONS

NEB catalog (1998/1999), pp. 121, 284.*
Genbank, NCBI Reference Sequence: NG_007494.1, version GI: 171184448, 2013 (19 pages).
Genbank, NCBI Reference Sequence: NG_009208.2, version GI: 301336136, 2013 (19 pages).
Pham et al., "Heterogeneous molecular background of the weak C, VS+, hr$^B$-, Hr$^B$-phenotype in black persons," *Transfusion*, vol. 49, pp. 495-504, 2009.
Silvy et al., "Identification of novel polymorphism restricted to the (C)ce$^s$ type 1 haplotype avoids risk of transfusion deadlock in SCD patients," *Br. J. Haematol*, vol. 160, pp. 863-867, 2013 (including 2 pages of Supporting Information).
Tax et al., "*RHC* and *RHc* genotyping in different ethnic groups," *Transfusion*, vol. 42, pp. 634-644, 2002.
Westhoff et al., "DIIIa and DIII Type 5 are encoded by the same allele and are associated with altered RHCEce alleles: clinical implications," *Transfusion*, vol. 50, pp. 1303-1311, 2010 (Author manuscript version, 17 pages).
International Search Report and Written Opinion for International Application No. PCT/EP2014/052411, dated Apr. 10, 2014 (14 pages).
Sala et al, "Analysis of the Protein S Gene in Protein S Deficiency," *Methods in Molecular Medicine*, vol. 31, pp. 249-268, 1999.

* cited by examiner

*Primary Examiner* — Jehanne Sitton
(74) *Attorney, Agent, or Firm* — Klarquist Sparkman, LLP

(57) ABSTRACT

The present invention provides a method for detecting the presence or absence of, or for discriminating between, blood type variants, including RHD*r's, RHD*DIIIa and RHD*DIVa-2. The method comprises amplifying by PCR a sample obtained from a human subject at intron 3 of the RHD gene locus. The invention also provides products, in particular, probes, primers and kits for use in the method of the invention.

27 Claims, 7 Drawing Sheets

Figure 2

| | RHD | | | RHCE | | RHD | Serology |
|---|---|---|---|---|---|---|---|
| | presence or absence of an RHD/RHCE hybrid exon 3 allele | exon 4 (position 602) | exon 7 (position 1048) | presence/absence of an RHCE*C allele | exon 7 (position 1006) | intron 3 at position 3100 | |
| r's | presence | G | C | absence | T | G | C+w |
| DIIIa | presence | G | G | absence | G or T | A | C- |
| DIVa | presence | C | C | absence | G | A | C- |
| New variant | presence | G | G | absence | G | G | C- |

Figure 3

```
              3010       3020       3030       3040       3050
RHD       TTATTCCCAA GGCAAATATG GAAATTTGAT CATGTACTAA TCATAATAAA
RHCE*ce   .......... .......... ...G...... ...A.G.... .....C....
r´s       .......... .......... ...A...... ...G.A.... .....C....
DIVa      .......... .......... ...A...... ...G.A.... .....A....
DIIIa     .......... .......... ...A...... ...G.A.... .....A....
#425      .......... .......... ...A...... ...G.A.... .....A....

3060       3070       3080       3090       3100
RHD       GCTGGATTCT CTTTAAGAGA TTGAGAAATT AAAAGGCAAA AGCTGATATA
RHCE*ce   .......... .......... .......... .......... .........A
r´s       .......... .......... .......... .......... .........G
DIVa      .......... .......... .......... .......... .........A
DIIIa     .......... .......... .......... .......... .........A
425      .......... .......... .......... .......... .........G 3110       3120       3130       3140       3150
RHD       TCATGTTTAG TTATATTGTG AGTCTTATAA GAAGCTGGGA GGCAACCCCA
RHCE*ce   .......... .....C.... .......... .......... ..........
r´s       .......... .....T.... .......... .......... ..........
DIVa      .......... .....T.... .......... .......... ..........
DIIIa     .......... .....T.... .......... .......... ..........
#425      .......... .....T.... .......... .......... ..........

3160       3170       3180       3190       3200
RHD       TTAACTCACC AGAATACAGA ACTCAGTCTC ACAACTTAGA TATAATTCCT
RHCE*ce   .......... .......... .......... ........A. ..........
r´s       .......... .......... .......... ........A. ..........
DIVa      .......... .......... .......... ........G. ..........
DIIIa     .......... .......... .......... ........G. ..........
#425      .......... .......... .......... ........G. ..........

3210       3220       3230       3240       3250
RHD       CTCAAACCTT TTCCTCAAAG ATTAAATTCT GAAAATAATC TTGTGATTAA
RHCE*ce   .......... .......... -......... .......... ..........
r´s       .......... .......... -......... .......... ..........
DIVa      .......... .......... A......... .......... ..........
DIIIa     .......... .......... A......... .......... ..........
#425      .......... .......... A......... .......... ..........

RHD       (SEQ ID NO: 29)
RHCE*ce   (SEQ ID NO: 30)
r´s       (SEQ ID NO: 31)
DIVa      (SEQ ID NO: 29)
DIIIa     (SEQ ID NO: 29)
#425      (SEQ ID NO: 32)
```

Figure 7

SEQUENCE LISTING

```
<160> NUMBER OF SEQ ID NOS: 32

<210> SEQ ID NO 1
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 1
atatggaaat ttgatcatgt                                                       20

<210> SEQ ID NO 2
<211> LENGTH: 11
<212> TYPE: DNA
<213> ORGANISM: Artificial sequence
<220> FEATURE:
<223> OTHER INFORMATION: Synthetic sequence: Primer

<400> SEQUENCE: 2
astaatsata c                                                                11

<210> SEQ ID NO 3
<211> LENGTH: 14
<212> TYPE: DNA
<213> ORGANISM: Artificial sequence
<220> FEATURE:
<223> OTHER INFORMATION: Synthetic sequence: Primer

<400> SEQUENCE: 3
aaatttgatc atgt                                                             14

<210> SEQ ID NO 4
<211> LENGTH: 11
<212> TYPE: DNA
<213> ORGANISM: Artificial sequence
<220> FEATURE:
<223> OTHER INFORMATION: Synthetic sequence: Primer

<400> SEQUENCE: 4
actaatcata c                                                                11

<210> SEQ ID NO 5
<211> LENGTH: 11
<212> TYPE: DNA
<213> ORGANISM: Artificial sequence
<220> FEATURE:
<223> OTHER INFORMATION: Synthetic sequence: Primer

<400> SEQUENCE: 5
actaatgata c                                                                11

<210> SEQ ID NO 6
<211> LENGTH: 11
<212> TYPE: DNA
<213> ORGANISM: Artificial sequence
<220> FEATURE:
<223> OTHER INFORMATION: Synthetic sequence: Primer

<400> SEQUENCE: 6
```

-continued

```
agtaatcata c                                                        11

<210> SEQ ID NO 7
<211> LENGTH: 25
<212> TYPE: DNA
<213> ORGANISM: Artificial sequence
<220> FEATURE:
<223> OTHER INFORMATION: Synthetic sequence: Primer

<400> SEQUENCE: 7
aaatttgatc atgtactaat catac                                         25

<210> SEQ ID NO 8
<211> LENGTH: 15
<212> TYPE: DNA
<213> ORGANISM: Artificial sequence
<220> FEATURE:
<223> OTHER INFORMATION: Synthetic sequence: Primer

<400> SEQUENCE: 8
atgtactaat catac                                                    15

<210> SEQ ID NO 9
<211> LENGTH: 25
<212> TYPE: DNA
<213> ORGANISM: Artificial sequence
<220> FEATURE:
<223> OTHER INFORMATION: Synthetic sequence: Primer

<400> SEQUENCE: 9
aaatttgatc atgtactaat gatac                                         25

<210> SEQ ID NO 10
<211> LENGTH: 25
<212> TYPE: DNA
<213> ORGANISM: Artificial sequence
<220> FEATURE:
<223> OTHER INFORMATION: Synthetic sequence: Primer

<400> SEQUENCE: 10
aaatttgatc atgtagtaat catac                                         25

<210> SEQ ID NO 11
<211> LENGTH: 26
<212> TYPE: DNA
<213> ORGANISM: Artificial sequence
<220> FEATURE:
<223> OTHER INFORMATION: Synthetic sequence: Primer

<400> SEQUENCE: 11
ggaaaaggtt tgagaggaat tatatt                                        26

<210> SEQ ID NO 12
<211> LENGTH: 19
<212> TYPE: DNA
<213> ORGANISM: Artificial sequence
<220> FEATURE:
<223> OTHER INFORMATION: Synthetic sequence: Primer

<400> SEQUENCE: 12
tgggcttcct cacctcaaa                                                19

<210> SEQ ID NO 13
<211> LENGTH: 19
<212> TYPE: DNA
```

```
<213> ORGANISM: Artificial sequence
<220> FEATURE:
<223> OTHER INFORMATION: Synthetic sequence: Primer

<400> SEQUENCE: 13
tgatgaccac cttcccagg                                                    19

<210> SEQ ID NO 14
<211> LENGTH: 17
<212> TYPE: DNA
<213> ORGANISM: Artificial sequence
<220> FEATURE:
<223> OTHER INFORMATION: Synthetic sequence: Primer

<400> SEQUENCE: 14
ggccaccacc atttgaa                                                      17

<210> SEQ ID NO 15
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 15
ggtagcaggc gtctgtaaaa a                                                 21

<210> SEQ ID NO 16
<211> LENGTH: 19
<212> TYPE: DNA
<213> ORGANISM: Artificial sequence
<220> FEATURE:
<223> OTHER INFORMATION: Synthetic sequence: Primer

<400> SEQUENCE: 16
catagacagg ccagcacag                                                    19

<210> SEQ ID NO 17
<211> LENGTH: 17
<212> TYPE: DNA
<213> ORGANISM: Artificial sequence
<220> FEATURE:
<223> OTHER INFORMATION: Synthetic sequence: Primer

<400> SEQUENCE: 17 tgccctgga gaaccat                                                       17

<210> SEQ ID NO 18
<211> LENGTH: 25
<212> TYPE: DNA
<213> ORGANISM: Artificial sequence
<220> FEATURE:
<223> OTHER INFORMATION: Synthetic sequence: Primer

<400> SEQUENCE: 18
aaattaaaat aagcatttga ccatc                                             25

<210> SEQ ID NO 19
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 19
cctgagatgg ctgtcaccac                                                   20
```

<210> SEQ ID NO 20
<211> LENGTH: 17
<212> TYPE: DNA
<213> ORGANISM: Artificial sequence
<220> FEATURE:
<223> OTHER INFORMATION: Synthetic sequence: Primer

<400> SEQUENCE: 20
acatgccatt gccgttc                                                17

<210> SEQ ID NO 21
<211> LENGTH: 19
<212> TYPE: DNA
<213> ORGANISM: Artificial sequence
<220> FEATURE:
<223> OTHER INFORMATION: Synthetic sequence: Primer

<400> SEQUENCE: 21
tctcacctgc caatctgct                                              19

<210> SEQ ID NO 22
<211> LENGTH: 64956
<212> TYPE: DNA
<213> ORGANISM: Homo sapiens

<400> SEQUENCE: 22
gacaccccag ccacgccaag ccgggaagtc cccgcctcct ggagctgaac ccgcccctct    60
cccagaggtg gagctgcggg gggcgggaac aggcacggag aaaataaaca agactaaaaa   120
gtcctgagta gcgctgtgtg ccgcaaaacc tgaacccacc ttttgcacca cgcgggaccc   180
ggcacgcttc ctgccacccc ccctgagag ggctgcgcgg ccgaccccag tactagaaaa   240
cactcgtcac ctcaatcaag acgggtacga aggccaacgg acgccttcct ttagaacgct   300
cagcacacag agcaacttct cacgcctact ctcaaatggc gtactccaaa ctagcactcc   360
cgacgtccag ctgtgaaccc agagcggcgg aaagcccctg aacccagcgc ccgggcatgc   420
gcagacgcgt tgttgtggtg ggcgtggctc cctccggacc cggcgccccg ccctccgccc   480
cgtgtccgca tgcgcgactg agccgcgggg gtggtactgc tgcatccggg tgtctgaaga   540
tccgatgaaa taacatatgc aaaatgattg ggtccgtgat tggcattcca gaaatggtag   600
ctgttattca gccaacaaat atttattgag cacctactat ggacttccct ggtgctgagg   660
atacaacagc aaccacagca gtcaaaagtc cctgtcttca tgttgctcag attctcatag   720
gggaaagcaa ataatgaaca aatacacggc cgggcgcagt ggctcacgcc tgtaatccca   780
gtactttgcg aggccaaggt gggcaagtca cctgaggtca ggagttcgag accagactag   840
ccaacgtggt gaaaccctgt cactactaaa aatacaaaaa ttagcgcggt gtggtggctc   900
atgcctgtag tcccagctac ttgggaggct gaggaaggag aatcgcttga acctaaaagg   960
cagaagttgc aatgagccaa gatcgtgcca ctgcattcca gcctgggtga cagagtactc  1020
cgtctaaaaa aaaaacctaa atacacaagt aaaaatatag acctcgtcag atgctagtaa  1080
gtgctgtgaa ggaaactaaa aggggaacac aaggaaccct tgtcaagggg agaagaaagg  1140
ggagttgatg ctgtcctttt aaatagggca gtcagaggcc gggcacagtg gttcacacct  1200
ataatcccag cactttggga ggttgaggtg ggtggatcac ttgaggtcag gagttcaaga  1260
ccagcctggc caacctggtg aaatcctgtc tctactaaaa aaacaaaaac tagccgggtg  1320
tggtatcacg cgcctataat cccagctact cgggaggctg aggcgggaga atcacttgaa  1380

```
cctgggaggt ggaggttgca gtgagccgag attgtgccat tgcagtccag cctaggcaac    1440
aagagcaaaa cttcatctca aaaaaaaaaa aaaaaatagg gcagtcaggg aaaacttttcc   1500 tgagaagggg atggtggagg atccagggag gtgaggtggg gagcaagcca gtacagttgt    1560
tccttgactt tcgatgggt tatgtcctga taaagccatg gtaagtagga aatattgtaa    1620
gtcaaaaatg catttaatac atctaaccta cggaacatca tagcttagtc tcacctacct    1680
taaacatgct tagaacactt acattagcct acagttgggc aaaatcctct aacacaaagc    1740
ctattttatg ataaagtatt gaatatctca tgtaatgtac tgagtactgt acggaaagtg    1800
aaagacggag tggtgggatg ggaactctaa gcgcggcttc cactgcatgt gtgttgcttt    1860
cgcgccatca taaagttgaa aagcgttaag tcaaaccatc gtacgtcgga ggccatctgt    1920
atctggtagg aggagtgttt cagacagaga gaacagcagg tgcacagagt gcttttttcc    1980
cagcatttta ttatgaaaaa tttcaaacat ctaccaaaaa aagttgaaag acttgtacag    2040
tgaaaagcca tacatctcac agctagaatc aacaattaac attttactgt atttggtttt    2100
tgacttatct atcctagatc ccttgtgctt tctgtagcag gtgacctgcc ttgaagattt    2160
aaagacagaa tatcaggaaa tgtagtcaga aaatgggcc ttttataaga gtcagagggg    2220
aagagcaaaa cctctgcttt tgacaaatct gttgggagag gccaactgca gggatacctc    2280
ccttttttaa tgaaagcatt tctgttctgc gaggagcggg atcctcttgt caagcagtca    2340
gtccctgctg cttccttact ggggcaggat caggacgcac agggatttgg agtgccttgg    2400
aaccaaccac cacccacgcc gtttgccagc tggtaaacat gcccatcagg tccgggggtt    2460
ggcattgcct ggacatcttt agtgttcatc ttgctgacat ctggtgccct cgggcaggta    2520
ggtgcagttg gctgcctggt ttacagagct tgtactgggc ccaggttagc agaggtcaca    2580
tccatttatc ccactgcgca gaggagttcc ttctcaggaa acccagttta taagaagtac    2640
tgactgccag aaatagagca gaaatgagaa ccaggaggca attgtgagag gaatggagac    2700
ttctgacctc tggggattgg ggtacccctcc cccttaattg ctgttggggt agcagagggc    2760
ttagaagccc atgttcctag acttttagaa ttggaagaag acttagaagt aatctaggct    2820
gggggtcccc aaccccagg ctgtggcccg ttaggaacct gaccgcacag catgagggat    2880
aggccagcga gcactaccgc ctgagctccg cctcctgtca gatcagcagc ggcattagat    2940
tctcataggg gcacaaaccc tattgggaac cgcgcatgag agggatctag gttgcgtgct    3000
ccttaggaga atctaactaa tgcctgatga tctgaggtgg aacagtttca tccccaaacc    3060
atccctccaa cctcaccccg gtccatgaaa aaattgtctt ttacaaaacc cgtccctggt    3120
gccaaaaagc ttggggaccc ctgatctagg ctacagttaa gtggtcaaac acccaggtcc    3180
tgaagttagg ctgcctgggt ttaaatccca gctctactgc ttactagccc tgtgaccttg    3240
agcaagtcac ttagttttc tgtgcctcag ttcactcatt tgtaataaat cctaatagta    3300
cccatcccag tgtcatgaac taagttcata tatgtaaagt acttagaatg gtgcctagca    3360
agtacttaat aacagttagc tctgaaaatg tataaagcaa aattaaccaa tgttttagtg    3420
gtttgcagcc aacttttttc tatgcgtgtg ctaacatatt attttataag agtgggaata    3480
tattgtacat gctgttatat aacttgcttt ttcactaaac agtctatcct ctgtgtcagt    3540
tttgataaaa gcgttttcct cttgcttttc ctgcatatgt tcagaaccat catattggta    3600
gcaagtttca tgtcctgtag ttttcttaac caacccctg ctagtggaca tttaggttag    3660
tctcagtttt ttccttctgt aaataaagct gcactgagca agaagtgact gatgccaagt    3720
gactagatga ccttaggtat gacctctctg ggtcttggtt tcttggtcta aaaacaaaat    3780
```

```
gacaggattc gactgggtga ttaaaatctc ctctgatcta cataggaatt gttttcaaga    3840
catttctgca ttcctctagt gacagggtgc tcactacctc atgagtattt cagtggacaa    3900
ctgtaatggt caataaagta tccactttcc acctccctgc agctcctggc cctggcttta    3960
ttctctgggg ctccacacat tcagtttaca ctcagtggcc agtggctggg accattgtag    4020
aaaataagga aactccaatt ccttccttct tttcttcctc tttcatctct tcctccctct    4080
ctacatccct ctctctcttc cttccttcct cgacacttac catgtaccag accttctgcc    4140
aggcacatgg atgggagcac aggggaagtt ggctgcaggg ttagaactaa gtcccaagcc    4200
ccctaaagct catgccaggg gactggactg tccagtactg agggatgggg atgctgaggc    4260
tggtggcctt cctcaaatgc actgtagtgc cccaggcaga gtcctgggct gccctgtgag    4320
gaggtgacca gaggtagagc aacttcaccc taaggctgga tcaggatccc ctccaggttt    4380
ttactagagc caaacccaca tctcctttct cttctgccac ccccccttaa aatgcttaga    4440
aacacataga tttaaataca aattcaaatg taagtaattt caactgtgta actatgagga    4500
gtcagttcta cgtgggtcct atctgtatcc tccccagggc tcagctccat tctttgcttt    4560
cattcattct cattcaatac attgttgtta agagctcact gggtgccctc tctgtcatgt    4620
agtaaggttt taaaagaaa gcctcttctg agcttcagtt tccttattca taaaatagga    4680
gtattgatcc attccttgct tttcttacaa ggatatgctg aagatgactg aagtacagag    4740
taaagaagga ttatgtttgg gtgtcaaagg aatagaatgc cctcttttcaa actgagcaca    4800 gcaggaacct gtaacaggaa cacagcaact tgttgaatga atgacaatat tggaaaacat    4860
acatttcctc ccctccccat catagtccct ctgcttccgt gttaactcca tagagaggcc    4920
agcacaacca gccttgcagc ctgagataag gcctttggcg ggtgtctccc ctatcgctcc    4980
ctcaagccct caagtaggtg ttggagagag gggtgatgcc tggtgctggt ggaacccctg    5040
cacagagacg gacacaggat gagctctaag tacccgcggt ctgtccggcg ctgcctgccc    5100
ctctgggccc taacactgga agcagctctc attctcctct tctatttttt tacccactat    5160
gacgcttcct tagaggatca aaaggggctc gtggcatcct atcaaggtga gagttcattg    5220
gaaaagtggt cacaggagca aatagcaggg gcaggggcgg gggaggcctg tggttctcca    5280
ggggcacaga tgttcctttc tacaaaatcc caaggaaaaa gattccccca tcttcttccg    5340
tagattgcac cgaaattcag ccaacaatgt aagctttcct ttagaagcag cctgggcatg    5400
ccctcttctg tgaagcctgc cttgattttt cagcacagtg agaggcatcc tctttggtgt    5460
tcctcaaatt ccctctacca aatggtcttc ataattctct gcttctctgc ttccccttct    5520
ctctcctcag tggcaaggaa ttttttttatt tttatagatt tagggataac aagtgcagct    5580
atcttatgca agcaatttca tgttgttggg ttttttggttt ttgtttcctt tttgtggcct    5640
ctcgctcatt tcttatttct ttttgaggca gggtctcact ctgttgccca ggctgaagtg    5700
cagtggcatg atcatggttc actgcagcct tgacctccta gtctcaagca atcttcccac    5760
ctcagcctcc caagaagctg gaccacagg agggcaccac catgcctggc taattttttt    5820
tttttttttt tttggtagag atgtgggtct cctgtgtttt cccagactgg tctcaaactc    5880
ctggacacaa gcgatcctcc agcctcagtc tcccaaagtg ctggaattac aggcgtgaag    5940
cactgtgccc agctctcttg ctcatatcta tactagtttt cttttggaag cttcagcctg    6000
ttgctacccc ccaccccac ccccaccgac cccagctttc ttctcactta ggggctggga    6060
agtctgcatg ctgtctataa atccagaacc agaaggtatg gctgaagggg agggtaggat    6120
```

```
gatggttatt ttatattcag ctaaaaatat tcccagactg tgatgagaca actgtaaata    6180
agacagatgt ccacaatggt gtgactttgc ttttttaaaa atattgaaat gagtttcagg    6240
catctcagtg ggctgatagg ttgttgataa tagacagggc ctccttgaag aatgtccctg    6300
agacaaagtt gaagcttgag cctggttgag tccttgcttg ttcctaggtt gatatgaacg    6360
gctagttaac tggaagcaaa gagaagtcat cctgggggcc atggcagtga caagtaggac    6420
ttagggaggg aagcccttat accatttaag gtgctggccc agagaggagc cttcagtgac    6480
agacaaacaa gagctggcac aattttaatt cacttcaatt tactctaatt catttcaatc    6540
caatacaatt caatgcattc cattcattca accatgtatg acatccaatg tgggatccag    6600
actcatgatg attagagctg atatttatga gcacttacta tgtaccaggc actattctac    6660
atgctttaca ttgaaccctc acaataaccc aatgaggtgg gtactattat gatcttcgtt    6720
tttcatatga ggaaactagg catatggatg ttgagtaatt tgcccacggt cgctcagcta    6780
gcaatagcac agcgtattta aatttagcca ccctggattt agtttcctta cacttaacca    6840
ttatgcatca tggccccatt ttacagtggg cttgagtctt tgtcatataa cccagtaggt    6900
tagcagccac tattccaacc ctgtagattg actctagggt ccatgttctt taccoctgca    6960 ccgtgctact aacgtaggta caaaatgtcc tcagaaactc actttatacg gaagctcaga    7020
ggagggtcca aacccaggc aggggagacg atggtgtcag gggagggagg tgactgccca    7080
gccaggtctt gaaggctcag taggaattac ctgtgggaca aaggagggtc atccaagtga    7140
gggcacagtg ggtgccatgg cgtgcacaca aatagagca gactgagcct gggcttaaca    7200
ttgcattgcc ctggagccta aaaggggaaa caaagggccg ggcgacgtgg ctcacgcctg    7260
taatcccggc acattgggag gccaaggctg gagaatcacc tgaggttagg agttcgagac    7320
cagcctggcc aacatggcaa aaccgcatct ctactaaaat tataaaaact ggctgggtgt    7380
ggtggcacac gtctataatc cgagctactt gggaggccat tacactccag cctgggcgcc    7440
agagtgagac ttcatctcaa aaaccaaac aacaaaaaca acaacaagaa caacaaaaaa    7500
acaaagagga gagcagggac tgggtgtggt gactcatgcc tgtaatccca aacactttgg    7560
gagaccaagg caggcagatc acctgaggtc aggagttcga gaccagcctg gccaacatgg    7620
taaaaccctg tctctactaa aaatacaaaa attagccgga tgtggtggca cgtgcctgta    7680
gtcccagctg cttgggaagc tgagggagga gaattgcttg aacccaggag gcagaggttg    7740
ctgagctgag aacatgccac tgcactccac cctgggtgac agagtgggac tctgtctgaa    7800
aaaaataata gtaataaata aaaataaaga gggaagcagc gggtggcaga ctcactgggc    7860
tgcatacgaa gtttggcttc agtctgaggt ccgaatagta aacagcagcg agacaagttt    7920
gggtttgggt catggaggaa gccatgccag ggctggtgtt gggcacaggg aaagggggcat    7980 ggcttgagac accagaccag cgtggaggct gtagtgtagt attgacctga ggacttcaac    8040
attctgatgg tgtacacacg attttttgag catgtaccat ggttatatat tacacttttaa    8100 gtattacttt aagtattact acattaatat attttgtatg ttacaataaa tacatacaaa    8160
ttaggaaaat tgaaagagat caaaatgaaa tatataatat tttcaaatta ctaatcataa    8220
tggtgtcaat ctccaggcag ggtccattgc tacagttgac gatagtggat gaaaattcac    8280
tcctcagagt cttcttgata atttgaaatt gtcttgattg acttgtcaga tctgattaga    8340
tcaacatgtt ttaaatctcg aatgtgactg acagcttgta cgaggagaag tttcactctg    8400 cctttttccct tttgttcact tgactgccat tatttctatg cttccaatct gtgttttttct    8460 gcacgagttg gttaagccat tacttcattt tgtgaaagtt tgttgagtta aacttaggta    8520
```

```
acttaatctg tcaatccact taattgaatt cagtcctggt aaactataat agattattca    8580
aacctgccaa ttctaaaaag acattttgag acaatcagga aatctgaata tagcatgaat    8640
atcttacgat atacaaggat tattgttaat tttgttaggt atgataaaag catggtgggt    8700
tgtttttgtt tttgttttt  aagtctccat ctgttagaga ggcacattga aatggcatga    8760
tatctggggt ttgcttttat gccagaaaaa agaaaagta  cagaaggatt atagaaacaa    8820
gattggtctc atgtgacaat catcagagtt tggagatggg cacgtagggt catcgtgctg    8880
ttctctctgt tttcgtatat gctttaaaag ttctgtaata gttaattaaa aaaaaaaaa     8940
aacaccctgg ctgagcattt agggaggcca agtgggagg  atcgcttaaa ccaaggagtt    9000
caagacgagc ctaggaaaca tagggagacc cccccccatc tctaaaaaaa aaaaaaaaa     9060
aaaaaacttt aaaatttaac ccagtgtggt ggcacatgcc tatagtccca gctactcagt    9120
aggctgaggt gagaggcttg cttgagcctg ggagcttgag gctgcagtgg gacgggattg    9180
taccacttca ctccagcatg ggcgacagag caagaccctg tctcaaaaaa aataaaaata    9240
tttgaggtga agcgaggctg taataacaaa tttaaaaata taaataaaac ataaaggctg    9300
ggtgtagtgg ctcacgcctg taatcccagc actttgggag gccaaagcag gcagatcacg    9360
aggtctggag atggagacca tcctggctaa cacgatgaaa ccccatctct accaaaaata    9420
caaaaaatt  agccgggtgt ggtggcgggt gcctgtagtc ccagctactt gggaggctga    9480
ggcaggagaa tggcgtgaac ccaggaggcg gagctttcag tgagctgaga ttacgccact    9540
gcactccagc ctgggcaaca gagcgagact ccgtctaaaa aaaatgaaa  ataaaaataa    9600
atgaaacata aaaccctgcc attagttgca atatgaagaa tatagagaaa tgcatatcaa    9660
atccttctca ttggaccaat attcccttag ggcaccttcc aaagctagga gactcaaggc    9720
tgtatgacat cctgagcaag tgaggggtgg cttctgggtg aatctgaata ttaaatattt    9780
gcagaattga aaacttcaca aagtaccttt agagatagaa tagcctagat ccatgtttct    9840
caaagtgtgg tccccagacc tgctgcctca gcatctcctg gaaatttagt agaaatgcag    9900
attctcaggc cctaggccag acctactgat cagaagctct gggcctgggg cccagcagtc    9960
tgtgttttca caagccctct tggtgattct tctgtgcatg aaagttcgag aattcctgga   10020
gctagactga ttcaaatctt gcctctgtat cttagagacc ttgggcagat tagtcaacct   10080
cttttctgcct ctgtttctac ttctgtcaga ggatgatagt acttgtttca ttaagttgtt   10140
gaaaggataa atgaattgac acacataaag agtattagct tttattatca aaagcttttt   10200
ttttgagaca gagttttgct cttattgccc aggggagtgc agtggtgcga tcttggctca   10260
ccgcaacctc cacctcccag gttcaagtaa ttctcctgcc tcagcctccc gagtagctgg   10320
gattacaggc atgcgccacc acgcccggct aatttttgtat ttttagtaga gatgggttt   10380
ctccatgttg gtgaggctgg tctcgaactc ccaacctcag gtgatgcacc cgccttggcc   10440
tcccaaagtg ctgggattac aggcgtgagc caccgcgcct ggcccaaaag ctttaatttc   10500
ttaattttt  aaataaaata aataaaacta gaattgcttg ttttcttcca gctaccctgg   10560
tgattgtatt gagcattttc tggggtgtgt gttcttttgct gtaatgacta ctggtctgga   10620
tgacctgtga tgagaccaga tgggcagggg cagtggagga gattctagag atatttagga   10680
gataagtcag ctgtacttga tgaaaagagt ggggagttaa ggctggctgc agatgtatga   10740
tttggcatag agaggtgcca gttcctgaga tgagagacag aaggggaggg acaggttgtg   10800
aggatgaatg aacaatgata tgttcattct gggcttggag ttaaggggcc tatgatatgc   10860
```

```
ttaggggaag cagagagtat caattaccta ttgctgcata acagccaccc caaacttagt   10920
ggcttaaaat agtaacctttt taatttactc atgatcatga ttctgtggtg caacaactgg   10980
gctgggttca gctgggcagt tcttctgtta gtttcaccca gggtcattca tgcatctgca   11040
gtttggggtg ggatggcctc agatgacctc attcacgtgt ttggcagttg gtgattcact   11100
gggggccatt actgtaacaa tcgcctacca ggcagagctt ccctaaggct tccaaactag   11160
gagactatcc tgggtcctgt gctgtggata ccactcagtc ccccatcccc accccatatt   11220
cctcaaaggc agagagaggg gctactagaa gacagaggag ttttcccagt gacatgtaaa   11280
cactccaaac cctggcacct tccacactgc agctttggtc tgccccttttg ggaaatctct   11340
gttttttcttc ccaggctgct ggaggggtga gagtcgccgg tagagtagag gctgtgggcg   11400
aggaggtggc ggcctcctga ggctgcagtg gtctttccag gcagcagtgg gagcacaggg   11460
tggaggtcaa ccctagagcc tgggagagtg aagctgggtg tgacttcaga gctgttggtg   11520
ctgaagtttc tgcaggccag aaggaggggc aagagtggga ggggcgcag atccagaatc    11580
acggaggcag ctgaccggag gaggcagctg cccaaggga tggactcaga aggccaaagt    11640
gctgttatcc aaacgaactc tttgcaagtg gtctctttgc aacaggcctg ggggagagca   11700
gtcttgccta aagtcacacc gctaatcagc ggccggcacg gggtaacagt tactaacact   11760
cactacgtac ccaatgctgg gcgaagtgac ttgcatgagc cagcgagctc aatgctcatg   11820
gcaatcctct gagcagctgg cattgtttca tctcaattt acagctcagg aagctgggac    11880
acagaggaag agccaggctc tgaacactga caacctgatt gagagaccca cactgttcat   11940
caccgttacg ctatatatgc tgtatagaaa ggcaggatgg cataatggtt aaacctaggt   12000
aggtagggtt tgaatcctcc tgctaccatt tactagctct gtgacttgga ctagttatag   12060
cacctctctg tgcctcccctt tccccatctc taaaatgggg ataataaatc gtacctccta   12120
cctgaggctg ttgtgggcta agtctgtaag gcacgtagaa cagtgcctgg aacgtggggt   12180
actgtctatc tgtgtgcctg ctgttacaac aatggtgagt attgccttat ctctcgctgc   12240
tgaactacca ggttagactt cttttctgcaa gtcatgaggc tttcataaac ttttcctgaa   12300
ggcttttccgt agaatgtaca attccccctct gggtccaggc atgggcgccc gggtagcaca   12360
tccacttctt atcacccctg aacaccttag agcccatcag cttatcaaac cagcagctga   12420
tgtgagtgca gagcagactg tgagaggtgg aggctgatac cagtgaggat gctccaagct   12480
gggacccagc cctgaagcgg gagcccagat aatggatggg tggaaatggg cctggagccc   12540
aggagaagtg ggaggatgag ggggcagggg gaggagaagc ctgaaatcaa atgttatttc   12600
ctgaccagtt tggggtgcat gagctctgtc aacagctcat ggaaactgct gccctaatttt  12660
catcttgttg gctgaggcac aattcctctc tcagggacag tgtagagcct tggggaggaa   12720
ggccctgagc gcgtatacct ggaatcaggg aatcgggatc aggggcagca gctgtgccca   12780
ataaagcccc cacccaggat cctctgactt cctcatctct tttttttttt ttttgagctg   12840
cagtctcact ctgtcatcca ggctggagta cagtggtgcg atctcggctc actgcaacct   12900
cagccttctg ggttcaagcg attctcctgc ctcagcctcc tgagtagctg ggattacagg   12960
catgcgccac catgccaggc taattttttgt attttttagta gagacggggt ttcaccatgt   13020
tggccaggct ggtctcaaac tcctgacttc aagtgatctg cccacctcag cctcccaaag   13080
tgctaggatt acagacataa gccactgtgc ctggcctttt tttttttttt tttttgtaa    13140
acagggtctc cctctgtcac ccaggctgct ggagtgtagt ggtgtgaccg cagctccactg   13200
cagccttaac cttctaggca caagccatcc tcctacctca ccctcctgag tagctgggac   13260
```

```
tacaggcact cgccaccacg cccaagtaat tttgtatttt ttgtagagac aaggtcttgc   13320
tatgttgcct aggctggtct tgaactcctc agctcaagca atcctccctc cttggcctcc   13380
caaagtgctg ggattgtgct gggattacag gtgtgagcca ccatacctgg tctgacttcc   13440
taatctttag ggccccaact ctgcccttat ccaggcaact ctcctctccc catcttccac   13500
taacttcttt ggaatattcc agagctgtaa aagccttaga gagtatcaag tccaactcct   13560
atgtgttaca gacagggaaa ctgaggccta agagggtaa tggacttgcc taagatcact   13620
tagtgaggtg agagaagaaa gagctagaga cagcctagcc tgtgcaagga catagttcca   13680
ggcattcaga gctgggctct gctgccggca tgtttgggc ctggtagtta gttcactgct   13740
gaactaccag gttagatttt cttctccaa gttgtggagc tttcataaac ttttcctgaa   13800
ggtcttcctt acaatgtaca attctcctct gggcccggtc atgagcgccc tcacaggct   13860 ctctctggtc cccttctgta aaatgagagg aaaatggaag aattgctcta ctcatggaat   13920
cttcaataag tctgggccct atgcatatag cattgctaca aaatggcaga tgcactttaa   13980
caatcgtgtt taataaaagg ttggatttgc atatctgaag tggggcatgc agtctccaac   14040
tgaacacaag cctcactgct cccgcatgtg cactgcacct tcatatacat atttcctgct   14100
tggctcctga gggaatttga gtaatcccaa gaggaacccc tgtagaaaat gtcccctggc   14160
cacacacccc cattcctaag gatgcaagca ggagatagaa acattccctg cacctccctc   14220
cttgttgtca aagaagtgc aaagagttga atccttccta atgcccactt ctcacccacg   14280 cccccaaatcc ccaggtccca tggaggtcct tggggggcctc ctatatcctg gtggtgtcag   14340
gttgatttgg aaatgtcagt gtcctcccctt gtcctctctg gcagaccctg ggtatgtgta   14400
tgtttcaatg gaagtgaatt taatgtact ttataaatca aagactttt ctgagacttt   14460 ggagagttcc agtaatgaga gcttctcatt gttatcaagg ccagggctgg agaccagtgg   14520
caggtgagtt cctattgctg tgattgtcat gatgatgttg atgaacagtc actatttatt   14580
gagcgttctc catgtgccag tcactgtact aaacattatt cctttggat ttcccagaaa   14640 cctctcaggt gggtctaatt acccttattc agctgataag gaaagtaagc aacttacaag   14700
accacagggc tatgaagtgg aaacacataa attgatattt cattttattt atttattat   14760 tttgagacag agtctcactg tgtcgcccag gctggagtgc agtggtgcgg tctcagctca   14820
ctgcaacctc tgcctcccgg gttcaagcga ttctcctgcc tgcctcccga gtagctggga   14880
ttacaggtgc ccaccaccac atccagctaa tttttttgta attttagtag agacggggtt   14940
tcaccatgtt ggccaggcta gtctcgaact gctgacttca tgatctgccc acctcatcct   15000
cctaaattgg tatctttata tgtccaaaag agtcaactgg tggcaattta gtgaggttta   15060
atctaatagg aaatgataga gctgggatcg aacagagcca tgtgaactca aaacctatgc   15120
ttccccttcc acctttttga aaaacattgt ctaggctggg cacgatggct catgcctgta   15180
atcccagcac tttgggagac ggaggtgggt ggattacatg aggtcaggag ttcgagacca   15240
gcttggccaa aaattagcca ggcgtggtgg cgcgcgcctg tggttcccac tgaagcacag   15300
gaggctgaag cacaagaatc acttgaaccc gggaggtgga ggttgcagcg agccgagatc   15360
gcaccactgc actccaacct gggcaacaga gagactctgt ctcgaaaaaa aaaaattgtc   15420
tacatgctgg ttgcagaaaa tttaaacact aaaactaaaa aagtaaaaca cctcccaaac   15480
ttagagacaa tattaatgac ggaaaaaaaa ttcttcaaga tctctctctc tccagtcatt   15540
tattcatgtg cgaaaacagt tggtgattat tgataaaata gcttttagag tttggagcaa   15600
```

```
ttatgtgcat tacatatacc atttgattct ggcaacctaa tgaaggagta tgatcatttc   15660
ccctatttaa cagacaagaa caagaagagg gagggcagat ggtgtggtag tctaaggcac   15720
aggctccagc agattatcta ggtgtaaatc ttggctgtag gccaggccct gtggctcatg   15780
tctgtaatcc catcactttg ggaaaccgag gtgggcagat cacttgaggt caggagttcg   15840
agaccagctt ggccaacata gcgaaacccc ttctctatta aaaatacaaa aattagccgg   15900
gcacggtggc aggcacctgt aatcccagct acttgggagg ctgaggcagg agaatcactt   15960
gaacccagga ggcagaggtt gcagtgagcc aagatcttgc cactgtactc cagcctgggt   16020
gacgagtgaa actctatctc gatattaaaa aaaaaaatct tagctctacc caccggggca   16080
agttacgtaa cgcctctgtg ccttggtttt catatctgta aaatggtgac agtaacagca   16140
cccacgtcaa agtgtggttg tgagaacgaa acaagatagt ctatgtaaag tgattaaaac   16200
agcgtaggca catggtaaac gcttaggaaa tgtaggctgt tataaagctc agagatgtta   16260
agtaactaga tcaagatcac acagttagag ggtgccagag tcctgatttg aacccaagtt   16320
tgtctcgttc tggagctcaa gctgctaacc cttttcaaa actggaatta aaccaaagtg    16380 ctcacctcc gctttgctgg gcccctccct gccctcaggt gcgtctcttc cactcacctg     16440
ccacagcagc ctctgctcag ggtctgagac cgggaaaggt gagggctacc caggtggccc   16500
tgatgttttc tgccagccag ctcaccaggt ccctcgcagc aggcggcaaa gggagggagg   16560
tttgctgtga agattatgtg gttcccaaca acaagagcgc tgggcctatc tctgccctct   16620
cttttctgtg tgtcctggga caagtcactt ggcttctgtg gcttcatttt ctcatgtgcc   16680
cagccagggg gttggccctc atatgcaata acagcagcaa tgacctttac tgagtgtcca   16740
tgtgcgtcaa gcacgtgtgc tttacacttg ttcttattat taggtttaat aatagaataa   16800
ttgccacatt tactgagcac tcattatggg ccaggccctg ccctaagtgc ttaattagct   16860
ttagctcctc taatccttat cttatcccca cacggcatgt tatgttatcc ccattattca   16920
gttgagaaca ttgaggctca aagaggcaaa gtaacttgac caaatacttg taaacgatct   16980
tgcatgcccc ttccagctgc catttagtaa gactctaatt tcataccacc ctaaatctcg   17040
tctgcttccc cctcgtcctt ctcgccatct ccccaccgag cagttggcca agatctgacc   17100
gtgatggcgg ccattggctt gggcttcctc acctcgagtt tccggagaca cagctggagc   17160
agtgtggcct tcaacctctt catgctggcg cttggtgtgc agtgggcaat cctgctggac   17220
ggcttcctga gccagttccc ttctgggaag gtggtcatca cactgttcag gtattgggat   17280
ggtggctgga tcacttctgg gtcatagagg gaatggaccc cgaaaggaca ggttccagaa   17340
gatctgggat attgccccct ctctgtctag caccagtgct gtgcaatatt taggacatcc   17400
ttatactaaa agattattca ttgtttaaaa ttcaaattaa ctgggcatcc tgtattttac   17460
tggacagccc tactccgtgt atcacaagga atccaggcct acattcctcc tgcatccttt   17520
ctttcctgtt attgtcgatt atgatttgt aaagttacat aatcaatata agtttatgga     17580
aaacgtaaga aggaaacacg ttagacagag agaaatagac atgccacacc tagagagaca   17640
ttctattttt tttttttttt ttgagacgga gtttcacttt tgttgcccag gctggagtgc   17700
aatggcgcta tctcggcaca ccacaacctc agccttctgg gttcaagcga ttctcctgcc   17760
tcagccgcct gagtagctgg gattacaggc atgtgccacc gcgcctggct gattttgtat   17820
ttttagtaga gataggggttt ctccgtgttg gtcaggctag tctcaaactc ctgacctcag    17880
gtgatccgcc cgcctcggcc tcccaaagtg ctgggattac agacatgagc caccgcgtcc   17940
agcctgagag acattctctt gaaaagaaag gactttcagc cccctaatgc tgctagacaa   18000
```

```
taaatagcca tgcctttatt ttcattaaat tacctgtgct tgtttacat gcatttgtgt    18060 gaaatgctaa gaaccatcac aactaatgta tggtgccaga agtcagaata gttgttacct   18120
gggcaggagg tggatattga ttaggaagga acacaaaata accgcatggg gtgcagaaaa   18180
tgttctctat gttcacctgg gtgatgatta cacatcaagc tatacacgtt ttaaaagggc   18240
attggcactt aataggagga agtaggctaa attttttcct gaaacattgt tttgttttgt   18300
tcaaacctct gaatccctgt gctgcccaga tgatggtaaa cgtcatccta ggcatcttag   18360
ggacctctca aggccattcc agcctcccct tctaagaccc tgctaaacct ctgggcactg   18420
ctgttaaaca tttctctatg agccaggaac tgtgctgagc actccacaaa tattattttg   18480
tttaactctt ccgggtaggg atctaacctg gtatacaggt aaggaagtgg aagctcagag   18540
agggcaaggc acttgcctag ggccacacag ctaagtggtg gagatggctc caactttta   18600 ttataacctt ttccacatgc tccagagtgc tcagaacatg aaacacagtc tagccagctc   18660
ccgattggcc ctggagggaa aaactttat atattttct ttttaaaag gtttagaggc     18720 tgggcatggt ggttcacacc tgtaatccca gtactttgg gaaccgaggt gggcagatca    18780
cttgagccca gaagtttaag accagcctga ctaacacagt gagatcctgt ctctgcagaa   18840
aatagaaaaa tcagctaggc gtggtggtgt gcacccacag tcccagctac ttgggaggct   18900
gaggcaggag gatcacctga acccagtgag gttgaggctg agtgagccat gatcgtgcca   18960
cttcactcca gcctggacaa cagagtgaga ccctgtctca aaaaacagtt ttaggggccg   19020
ggcgcagtgg ttcatgcctg taatcccagc actttgggag gccaaggcgg ggggatcatg   19080
aggtcaggag atcgagacca tcctggctaa ctcggagaaa ccctgtctct actaaaaata   19140
caaaaaatta gccgggcgtg gtggtgggcg cctgtagtcc cagccactcg ggaggctgag   19200
gcaggagaat ggcgtgaacc cgggaggcgg agtttgcagt gaaccgagat ggtgccactg   19260
cactccagcc tgggtgacag agcgagactc cgtctcaaaa aaaaaaaaca aaaacagttt   19320
taggccaggc gcggtggttc atgcctgtaa tcctagtact ttaggaggcc tagcaggtgg   19380
attacctgag gtcaggagtc cgagaccaac ctgagcaaca tggtgaaatc ctgtctctac   19440
taaaaacaca aaaattagct gggtgtggcg gcaggcacct gtaatcccag ctacttggga   19500
ggctgaggca gcgaatcac ttgaacccgg gaggcggagg ctatagtgag ccgagatcgc    19560
accattgcac tgtagcctgg gcgacagagt gaggctctgt ctcaaaaaca aaacaaaaca   19620
aaaacagtct atgagttaat tcccaccaga attcaataca cacacgcaca catgcacgca   19680
tacacacact gtgtccacct gggaagtgac aaagggcacc ctgggggatt tcaaatggtg   19740
gtggccctgg tttggtgttg ctgccttagc ttaaggtcac accagccttc agcctcctgc   19800
cccacagtct agggctgctc ccctcatctg atgtccacag ggacctgttt gttcttgact   19860
caatctagaa agacgagaag ggagagaagt cactcgcagc ctgagtgaac tcccctgccc   19920 caccctgac tgcttggatc ccctagggg tgaccctgc tgaaactggc tcttcctga      19980 ccggttcccg tcagggctgt gctgatgggt ggtgcccagg cctgcccctg ggacggggt    20040 actctccctt ggcaacactc cagcttgtgc cacttgactt gggactgatt tggttctgtt   20100
ttgagtccct tcaggggagg ggcctatctt attcaacgtt gttgtttgtt ttcctcacat   20160
actgataact tagcaaatgg ctattggagc aaaaatgaaa ataaacggaa ctctgaagtg   20220
ggatgtttta aaatttttat tatttttta gagacagggt cttgctctgt tgcccagtct    20280
ggagtgcagt ggtacaatca tagctcattg cagcctgtgc ctcctgggct caagtgatcc   20340
```

-continued

```
tcccacctca gcctcctgag ttaaattttt ttacaggcgc ctgctaccat gccctgctaa   20400
tttttgtatt tttagtagac aagggggtttc accaggtggg tcaggttggt ctggaactcc   20460
cgacctcaag tgatccacct gcctaggcct cccaaagtac tgggattaca ggcgtgagcc   20520
actgtgtcca gcctaaaact gttttttgaga cagggtctca ctctgttgtc caggctggag   20580
tgaagtggca tgttcatggc tcactcagcc tcaacctcac tgggttcagg tgatcctcct   20640
gcctcagcct cccaagtagc tgggactgtg ggtgcacacc accacgccta gctgattttt   20700 ctatttctg cagagacagg acctcactgt gttgctcagg ctggtctcaa actcctgggc   20760
tcaagtgatc tgcccacctc ggctctgaaa agtactggaa ttacagcctc ctgagtagct   20820
gagaccacag gcacacacca ccacacctag ctttttttttt ttttgctttt tgtagagatg   20880
gagtctcact atgttgccca ggctggtctc aaactccagg ccttaagcaa tcctcccacc   20940
tcagcctccc aaagtgcgaa gattacaggt gtgagccacc attcctggcc ttaaaagtgt   21000
gatattttta atgtattttg aaatctgcag gactctccct agaagataat agcaataacc   21060
aactccttta ttgtgcttga cgtatatcaa ctcactttgc ccttaccgtg gctccagagg   21120
cattgggtcc accttataaa tggaggcacc aaggcacaga gtgattaaat aaattgccca   21180
ggatcacaca gccagaaagt gtctgagtca agattccagc ccaggcagcc tagacctgag   21240
agcacgctcc taaccactgc acatcactgt cttagcacct cctcagcaca aactggccct   21300
tgaggaatga ataccgccg ccggcacaca cgctcctgag ttaagccttt gtcaatgaaa   21360
tgaacaccca cttaaaagga ataacctgtc caggcacgat ggaacattga gtaaccccctt   21420 attctaaatt cctggtccct gtaagactcc ttccccatgc ccttgccctt ttctgacctt   21480
cccctaaagt ccttgaggct taagcgggca tagtctgcag caaacactgg ggaagctgag   21540
tccagacttc agagcacagg ctttggatct aggccagctg gattgaacc tcacatttgt   21600 gatcagctgg catgactgtt tccaaaaagt ccattttaat cctctacgtg accctctgta   21660
aaatgggata ctgaatggtg agctagcacg attttacaga gagtgaattt ttttttgtgtg   21720 tgtgtgaggc agtcttactc tgttgcccag gctggagtgc agtggtgcag tctcggccca   21780
ctgaaacctc tgcctcccgg gttcaagcga ctgccatgcc tcagcctcga gagtggctgg   21840
gattacaagc atgcaccacc atgcccgggt aattttgta ttttttagttg agacagagtt   21900 tcaccatgtt ggccaggcca ctcttgaacc cctggcctca agtgatccac ctgccttggc   21960
ctcccaaagt gctgggagta caggcatgag ccactgcacc cagccttata gggttaaaat   22020
ttaaaagagg tgatgctgtt acaagcctgt tttacaaaat gctcttataa taaatcatta   22080
tcatcactgt tgctgtggtt gtagcatcat catcattaac tcccagaggg aggagggagt   22140
ctcagagcaa gctgctcagg ggagactgga tgtccatgga ttgtccagct cagtaccact   22200
tcctccagga agtcctccct gataagtcca gtcagcatca ccctctcctt ccaatgaacc   22260
ccactagcct tgtgatatca cagatattct tagttgacag gctcatggtg tagcctgtct   22320
agatcataag tacatttttt ttttttttgg atcataagta tcttcaagac caaaataatt   22380
ttctactcct gagcatgctc attggtcaaa ggaaggaagg aatcataata gcgttaataa   22440
ggctagcgtc ttttcagaag ttggttcttt gtgccagtct tggtgctaga cacaccgata   22500
ggaagaatac tccttcacat ccccaggaca ccaacatggg atacgtttga tcatcattct   22560
taatttgcag aaggagaaat aggctcagtg agatgaaata gccactccag tggcaaggct   22620
gggactggaa gccgggcttg tcctgattcc aaatccagtt tctttccact gccacgagga   22680
cggagagaag ggacagtggc cccagatggg gatggggtga ctggatgtgg gcaggcctgc   22740
```

```
ggggaagag tgccctctgt tgagcatccg aatgatggca gcagaaaaga agactgggca    22800
gaatcccagt tatcagatcc cctgagggaa cagtcacccc gatcaccctc agtcagatga    22860
gtgtgtgtag atcaatgcct catagatgaa ggcactgagg cacagagtgg ttaagtcatc    22920
tgccagacca catggctcag ggtgcagagg ccaccttaac gggagaagag atggtcactc    22980
cactctgcag catcagcgcc caggtgggta gaaatcttgt cttctattcc cacagaaagt    23040
aggtgcccaa cagtgtttgt tgaaagaatg aatgaatgaa tgaatgaatg aatgaatgag    23100
tgagaggcat ccttccttct cagtcgtcct ggctctccct ctctccccca gtattcggct    23160
ggccaccatg agtgctttgt cggtgctgat ctcagtggat gctgtcttgg ggaaggtcaa    23220
cttggcgcag ttggtggtga tggtgctggt ggaggtgaca gctttaggca acctgaggat    23280
ggtcatcagt aatatcttca acgtgagtca tggtgctggg aggagggacc tgggagaaaa    23340
gggccaaaag ctccatttgg tggggtttcc agggttttga aaataaaga caacctgtaa    23400 tcccagctac ttgggaggtt gaggagggaa gatcacttga ggccaggagt ttgagaccag    23460
cctgggcatc atagcaagat cctcatctct aaaagtaat tttttctaaa ttatccagtt    23520
gtggtggcat gcacctgtag tctcagttac tcaggaggct gaggtgtgag ttggaaggat    23580
tgtttgagcc caggagttag ggaccgagct gggcaacata gcaagacctc atctctaaat    23640
aaataggtag gtggatagac agatagatag atagacagac agacagacag acagacaggc    23700
tgggtacagt ggctcacacc tgtaatccca gcactttggg aggccaagga gggcagatca    23760
cctgaggtca ggagttcaag accagcctgg tcaacatggg ggaacctcat ctctactaaa    23820
aatacaaaat ttagctgggc atggtggcag gcgcctgtaa tcccagctac tcaggaggct    23880
gaggcaagag aatcgcttga acccgagagg tggaggttgc agtgaaccga gatcgcgcca    23940
ttgcactgca gcctggggga caagagcaag acttcatctc aaatttaaaa taagaaaaa    24000 agaaaagaaa agattgatag atagatagat atccaaatga gtttacaaaa atgtggtctg    24060
tgcaaatgtt taaacacaac aaaccaatgc cttaactac tacagtataa tcctgtagga    24120
ttgtgctatt catgatataa ttatggttat ataaaagtaa ttaattctca gagcctcacc    24180
agcagtgggt ccagcaagtt tgtacagcca gcatcttctt tcagtcagtg cgtgtcagta    24240
actgcatatg tcctctcatt gggagagcct gtcgaaagtc taaatttgaa ggcagctgtg    24300
aaggtaaggc caatccaaat ggctctccca gatcctctgc tgtaaccctg accctgagtg    24360
aggacatagc caaccttccc atctcatagg tgagaaagct gatgcctgga gaggggaagg    24420
gactgcccaa gatcacatag caagatagtg gcagaaccca agcgagaacc cacagttcca    24480
gcctggctta aagaaagtg cactggactt ggagtcaaag gctggggttt gcatcccagc    24540
tctgccataa atccctgtgt gactctgggc aatttaacct cttagagctt tagtttcttc    24600
atctgtaata tgagggtagc agtactacca cataggggttt tgagggagta attgaattaa    24660
tcacatgaga tgatgcatgt ttacaaaaaa aagcatgaag ccccttact gtgcctcagt    24720 gtcccaaagg actttggatt ttactctgag aaatacaggg agaactaggg agtgttgggc    24780
agaggagagc catgatctga cttatgtttt aagatactct ggcttctggg ttcagaaaag    24840
actgaagggg caagagagga agcaggtgga gaccagagcg gcagtgattg ccatcatcca    24900
gactcagact aggacaatag ctgtgagagt gatgggaagt ggttggatcc tgactgtatt    24960
ttaatagcag aattgacagg attttgctgat agactgcacg tggggtggga gagggtcaag    25020
atgacttcaa ggttctcatc tggcacaact cagcggctgc tggtgccatt tactgagatg    25080
```

```
gggaatgttg gggtgggata gatctgggag ggaaaaccca gagttcagtg tcgaatgtgg   25140
tagcgttagg gttaaggttg ggggagggg ggtagagatg tgtatgaaac atcccagtgg    25200
agacactgaa tggagatgta caagtctgaa gcttagtgga aaggttaggg ctagggatat   25260
aaatttggga gttgttacaa tacagatggt gtttaaagcc atgagaccca aggagatcac   25320
tcaggagtga ggataaagag agatgggaag aagtctgagg actgagtcct agaacaccct   25380
gcattttaga gggggacat gtgtaagagc cagcaaagga gacagaattg tgcttggaga    25440
ggcaggagga agcccaggag agcgtgaggt cctggaaggc aaggaaagag agggccccag   25500
gtgggctgaa tgctgctgag aggtcaagtc ggatgagggc tgggaagtag ccattggatt   25560
tggccaggag accttggcat gcatggttgt agaggaggat gaaggcaaca gcctggcttg   25620
actgattcaa gagcaggaga tgagaaagtg gagacagcat gcaggggcag ctctgccaag   25680
gactttgcta taaagggaa cagagaaatg gaggagaagc aggagggcaa taatccgata    25740
gagaggaaaa atctgatgat acagaagaga gatgaactgc aagagtcaag cctttgagtt   25800
ggaaagcagg agtgggattt tgagcactga tacctttagg ccgatgcagg gacagttcat   25860
cttttttttt tttttataca acattttatt taaaaaaatt attttcatag aatacatttt   25920
cacattagag attcccattg tgcggaaata acaatttatt acttatagtt ttatatttgt   25980
ggacagattg ttttagaaca agtagaatac atttgagaat taaatctcag tttacaatgg   26040
ataatatttt gatatgtctc tggggaaact tgcccttaaa tggaacttct gtatcttcag   26100
aagcactcca agcgtttctt cctaggattt agaaatttat aatatgagat agcagcattt   26160 cctaattta aaatttccct agtatatgta accatcagta ggtggtatct actgactaga    26220
gagggaagtt tttgaaaatt aaacactgtc taattttctg caaagttttt attcatgaat   26280
taagagtatt tccctttgtc cattattccc aaggcaaata tggaaatttg atcatgtact   26340
aatcataata aagctggatt ctctttaaga gattgagaaa ttaaaaggca aaagctgata   26400
tatcatgttt agttatattg tgagtcttat aagaagctgg gaggcaaccc cattaactca   26460
ccagaataca gaactcagtc tcacaactta gatataattc ctctcaaacc ttttcctcaa   26520
agattaaatt ctgaaaataa tcttgtgatt aagagaagaa ggctgtccac caatgggctt   26580
atctgttatt tcttccttat tgtgagctta atggcatgac aaagcagagg caaagaggca   26640
tacatcaatt cttcaaagta ggaagtcaaa aaggtcagag cttccacagc atggcaacag   26700
ctttgcagat gcccacatcg tgatagttga aatagcaaag cccagcaaag gttaaagctg   26760
aaaatgccaa aagccctgcc ttggcagctt tctgcgaggc atccccatga acataatcag   26820
taacaacttg tccaaggccc cagtgaccat gaagagtgag ggctgcagcc agggaatagt   26880
ccgtcgcaga gcaaggattc aaataagcag ccggaagcag acccgggagc aaaacactga   26940
caaccctctc gctagtccag tggagagatg cagccttgga gccagaatgg tggctcggtg   27000
acaagtgtat gtgctgcact ccacaccatt ctgggatagg tcggtcctga agaaatgctg   27060
agatatgagc aggtctgacc actggagttc gcagcaacag agctcggcct ccttgggcac   27120
cgcaaacggc actcagcctc cagggaaccg ccatctcgtt cctgaggcgg agttcatc    27180 ttaacgagag aaatgcagg gactgtgaat aggccggcag atttggtggc gggtgccaca    27240
ggttcagtct cctgcaggga gaggagaaaa tgccttacta attccttgta ttttctcaga   27300
gaaacaagag gcaccgtcat cagcctcatg tgagggtggg aaggagggat ggggtttgcg   27360
gagagggaaa gtgtggtatg gtcatctgtg ggagtggaag agagtgagag ggctgcaggg   27420
gtgcagcggg actgcaggct ggcaccaggg tccctagggc ttgtagttgg tggaaagtgc   27480
```

```
atcagtgacc agggctgtgt gcagctgctc caggcaggtg tggaagaagc agagttgaac   27540
ttgcccagcc tggagtgctg cccagagtga gcccaaagcc caggggagac cagagatggg   27600
gctgtttgca aaggaggaag tataacagta gcccacaaaa tctgagctgg ttaagaaagg   27660
agagagagtg aaaatgggga gcccagcctg gcagcctggg tacacatctc agctcaaccc   27720
acactagctg aatccatttg ggcccctccg ttgacctctc tgtgcctcag tttccctatc   27780
tatagaatgg ggataagaat aaggctactt cctagggctg ttgtgaggat tgaacaagtg   27840
accgaacact tgttcaattt tgaacactgt tctaaagcat ttaggacagt gcctggcatg   27900
gggtaagtgt tgcggcagtg ctgttatttt catcatcacc attgttctca ggctgcgttg   27960
attggagctg ctgaagggag gcaatttaag gaagtgagcc ggacagatag gaggtggtgg   28020
tggttatcag gtgcgatgct tgaaactgag gcttcggagg caacagttac tggtaatgac   28080
aaggtctaag gcttgacagt gggtggcaga agtgtaacgc agggaaagag acgagcggtc   28140
aaggagccga gagggaagga gttgggtgga ctaagatcat ttgtggaaga atgatggaga   28200
gaaaggctga agggcagggg ctgacatcat cagtgaccaa gaggcggccg ggaggctgag   28260
accacagcaa gaaagggaga gtgtgatggc atcttcttca agggagctgg ggatgtttgg   28320
ggtggaaaaa agaacaatgg tctgggaggg aatatgggaa attttttttt ttttttttt   28380 tttttttttt gagatggagt ttcgctgttg tcatccaggc tggattgcaa tgttgcaatc   28440
ttggctcact gcaacttctg ccttccaggt tcaagtgatt ctcctgtctc agcttcccga   28500
gtagctgaga ttacaggcac acaccaccac gcctggctta ctttttgtatt tttagtagag   28560 acggagtttt gccatgttgg ccaggctggt ctcaaactcc tgacctcagg tgatccaccc   28620
gccttggcct cccaaagtgc tgggattaga ggtgtgagcc accgcgccca gcctggaagt   28680
ttgtatttat taattttggg ttgtcttcat ctgtgtatgt gactttaacc cctaaatact   28740
tcagtgtaca tttctttttt tttttttctt tgagacagag tcttgctcca tcaatcaccc   28800
aggctggagt gcggtggtgt gatctcggct cactgcaacc tccgcctcct ggattcaagc   28860
aattcttgtg cctcaccctc ccgagtagct gggattaggg gcatgccacc atgcccagtt   28920 aattttgta ttttagtag agatggagtt tcaccatatt ggccaggctg gtcttgagct   28980
cctggcctca gttgatccac ctgtctcagc ctcccaaatt gctgagatta caggcgtggg   29040
ccaccataac cggcctcagt gtatatttct gatgcagttg ggttctgtat cccctccaa   29100 tctcatctcg aattgtaatc cccacgtgtt gagggcatga cctcgtggga ggtgattgga   29160 tcacagggt ggtttccccc atgctgttct tgtgacagtg agtgggtttt caggagagct   29220
gatggtttga aagtgtggca cttcctctct ctctttctct ctctctctca cctgacacca   29280
cgtaagatgt gccttgcttc cctttcacct tccaccatga ttgtaagttt cctgaggcct   29340
ccccggccat gccaaactgt gagtcaattc agcctctttt gtttataaat tacgcagtct   29400
caggaagtat cttatagca gtgtgaaaac agactaacac aatttcctaa aacaagggga   29460
cattctctta cataaccttt tttcagttaa caaaaatgag aaattgacat tgatatatta   29520
tgattacctt attctcattt caccaatttt ctcaataata tcttttctag aaaaaaatat   29580 atatttttg tggtcgagga ttacatccttg catttagttc tcatgtctta ttaaattcca   29640
tcaatctgga gcagtttctt catctttctt tatctttcat gaccttgaca tgttttgaag   29700
tttcgagcca gttctttttgt agaatgtggg tttgtctgct gttcctcatg attagattgt   29760
gggtatgcat ttttggtagg aattctccaa gagccgtgtg tgcccttctt agtatatcat   29820
```

```
atcagaagac atgctatcaa tttgccccat tactgggtgt gttaactgtg atcattgggt    29880
taagatggta cctgccagga tcttccactg caaagttact attttcccct ttgtaattaa    29940
taaacatctt gtgaggagat aatttcctat agaaatcctg ttgatcatcc aactttcacc    30000
cactgatttt agtgttcatt gattcttccc tgaataaatt agtactataa taattgccaa    30060
tggtggtttt ctaattccat ctttccttca gtagttggca ttcttctgta aggaaaagct    30120
ttcgcttctc tgttcatcca ctcatctatg tacttattta tatcaccatg ggctcctgga    30180
ttccggttta cacacttcca ttttctgcct tttctctctg cttaatataa ggattaatga    30240
gaactccctg attcccagga agaaaatgtc agcagagctt tcttaggcgg aatgaagaga    30300
attcagtgta agaaccataa aggtgtatct gtgtagtatg gacagtttta aaaacaaac     30360 aaacacaaag aacctccaag ggcaggaggt gctgccagac tcaggagggc actagaactg    30420
gctatgagaa gccactgaga tcccaggtag tctgtgctct ccatcttttg gctcttattc    30480
tctccgtaca tctaacatct ctgtacacca gctttctctt tagcgaaaaa cgtgtcccct    30540
ccacccaccc atccacctcc acttgttcct gcatttctat gtcccagatc ctgcagaaaa    30600
caactctttt ctctcagtta gtctcaattc tgtagtccag ggagagagaa tctgatcagt    30660
cccctgggtc atttttccac tctggtccaa gcagctacag ctggcatggg aaatagttca    30720
cacagtaaaa acatggctgt caagaagagg agtaaatttc agaggcagaa cactccctgt    30780
gagcccgaac ctcttcctgc tttgttgcag tcttcataac gattgcttta aaagactgca    30840
ttgatataac atcatctctc ttctctgcat ctttgacttg ctagcttaac tggtctagag    30900
gagggcttag cactgatttt gagtattcat tttcctcaaa acttcaattc agcctgggtt    30960
tcttcagcag gagggcccgg gggaaccaga gccagggacc agagtcattt cagtgcacca    31020
gctcaagaaa tgaatattcc aggccaagaa tccccaagtg ttcttcctga actccttcct    31080
ggtggagttc aaagagatga aaaacacaag cccgcttttc agttcttatc aggaaactgc    31140
atagactttc tcttttatgt atgactgagg cttttttacc atcatttgtt cccttcacaa    31200
atatttattt ggtatttact ataccagg gactcttgtg gcagtggaaa atacaactct    31260 catgaacgt ctgttccaga aggaaagact gccaataaac aataaaatag caaaagata     31320 tagcatgtta gagagtggta agtaccacag ataaaaatga aatggagaaa agaaacacga    31380
aaagttgggg agagaggata actgtttgag agggtggcca gggcagctt catcttatca     31440 agagggtgat tttttgagta cagacctgaa ggtaacgagt gcacaagcca tatgggtacc    31500
tgagaacagc ggcagaacaa tggcagggtg ctgggagggc tgtttaccag ccacgctgtt    31560
tagaattgtc agcacatggt gataaaaaa aaaaaaaaa aaaaaaaaca ggctgggagc     31620
agtggctcat gcctgtaatc ccagcgcttt gggaggccaa ggcggatgga tcacttgagg    31680
tcaggagttc gagaccaggc tggggaacat ggtgaaaccc cgtctctact aaaaatacaa    31740
aaattagccg ggcacggtgg tgggtgcctg taatcccagc tacttgggag gctgaagcag    31800
gagaatcgct tgaacccaac gggtggaggt tgcagtgagc caagatggca ccagtgcact    31860
ctagcctggc gacagagtga gactccgtct caaaaataaa taaataaata aatacaaata    31920
aaaagcagac agactttta gttggcttta gaattcttag acaccctcta cagacaaggc     31980
accccgattg cttgcaccca gggtggacta ctccctccac cctgcccttg ttacaccctg    32040 gctggggtc agcatttcag gcagctgaat gacccaaagt gggaacacgc tagtgggttt     32100
gaggatgagc aagtggagga gggcaatagg aggtgacgcc cgagaggtca ggtgagagtg    32160
gatcctgcag ggtcgtggca agaacctgga ccttgacttt gagtgacatg ggagccgctg    32220
```

```
gaggcttctg agcagaggag taacatgatc tgacttgcat tttattttat ttatttattt   32280
gacgcagtgt cactctgtcg ctgaagctgg agtgcagtgg cgacatctca gctcactata   32340
gcctccgcct cccaggttcc agtgaatctc ctgcatcagc ctcccaggta gataggatta   32400
caagcaagca tcaccacgcc tggctaattt ttgtattttt agtagagaca gggttttgcc   32460
atgttggcca ggctggtatc gaactcctga cctcaggtga tccacccacc tcagcctccc   32520
aaagtgctgg gattacaggc aaaattagaa tatatctaga atttcctgaa gaccttagtt   32580
tggtattata agaagtctgg ttgcttcatg ttgcaaaatt tatatcactc atcactcccg   32640
cagagttaaa attccgctga gaagtaggaa tcagtgaggt gcgtgtccat gtgggttttt   32700
gccacaccta agtgaacctt ggtcaaaagc atataagagc tactgatagg ccgggtgtgg   32760
tggctcatgc ctgtaatctc agcactttgg gagggaagga tctcttgagc ccaggagttc   32820
aagaccagcc tgagcaacat agcaagattc catctttaca caaaatttaa aaattggcca   32880
ggcatggttg tacattcctg taatcccagc tactcaggag gctgaggtgg gaggattgct   32940
tgagcctggg agttggagac tacagtgagc tgtggccaca ccactgcact ccagcttgag   33000
caatggagca agactctgtc tcaaaaaaaa aaaaaaagg ccaggcgcag tggctcatgc   33060
ctgtaatccc agcactttgg gaggccgagg cgggtggatc gcctgaggtc aggagtttga   33120
gaccagcctg gcaaacacgg tgaaacccca tctctactaa aaatacaaaa ttagcccagc   33180
gtagtggcgc atgcctgtaa tcccagctac tagggaagct gaggcaggag aatcgcgtga   33240
acctgggagg caaatgttcc agtgagccga gatcgtgcca ttgcactcca gcctgggcag   33300
agcctgctgg gttgggctgg gtaagctctg aacaccagtc tcatggcttc aagtcacacc   33360
tcctaagtga agctctgaac tttctccaag gactatcagg gcttgccccg ggcagaggat   33420
gccgacactc actgctctta ctgggtttta ttgcagacag actaccacat gaacatgatg   33480
cacatctacg tgttcgcagc ctattttggg ctgtctgtgg cctggtgcct gccaaagcct   33540
ctacccgagg gaacggagga taaagatcag acagcaacga tacccagttt gtctgccatg   33600
ctgggtaagg acaaggtggg gtgagtggtc tcctacttgg gctgagcaga atggctcaga   33660
aaaggctctg gctgaaaaaa tctccctcct ttaccaagtt ccctgggtg tctgaagccc   33720 ttccatcatg attcatttct ttgagtagtg tttgctaaat tcataccttt gaattaagca   33780
cttcacagag caggttcagg aggcctgggg tatgcagatt caaccctct ggcctttgt   33840 ttccttgtct gtaaaatgtg gttagctggt atcagcttga gagctcggag gggagacgtg   33900
acttccccat ctaactctaa gtgacaaggc tgagactctc cagccctagg attctcatcc   33960
aaaacccctc gaggctcaga cctttggagc aggagtgtga ttctggccaa ccaccctctc   34020
tggcccccag gcgccctctt cttgtggatg ttctggccaa gtttcaactc tgctctgctg   34080
agaagtccaa tcgaaggaa gaatgccgtg ttcaacacct actatgctgt agcagtcagc   34140
gtggtgacag ccatctcagg gtcatccttg gctcacccc aagggaagat cagcaaggtg   34200
agcagggcgc tgcccttggg cagcacttgg gtctaacagg actagcacac atatttatgc   34260
ccctccccac cccagggcca gcgtgggttg ggagagggca tgccgggtgg tggagctgtg   34320
cctgcctcta cagtggagct ctaggtagaa tgctgggtgg tcacagtggg cctgggactc   34380
aggagactgt ccagtgatca aaggctttct gggggtagtg attaaatcca tccatgctaa   34440
catgaaacag acctcagttt gaaccccatt tctgctagtt gctaaagtca gtcaccatga   34500
gcgagagtca gcagcaacag actagactag aattagccag cctctctctt ccccccaaca   34560
```

-continued

```
aatttcaaga atggaaccat cagaatcaga agtagagaag tatgtgacac tagccatgtg    34620
gctctggtca agccacttca acgttttgag tctcagtggc ctcatctgta aagtgggaat    34680
taagagatgg tgcatgtaaa gtgcttaacg gggagtaaat ggtaggcaaa cattagctgc    34740
tgctattagt aaagagagac gatggtgtgt gtgagtcttg tgggcagaga tgggtgagag    34800
gggagacaaa acaagttctc atgatgatgg gggaaggggc tccagctggt ggtgtcggag    34860
ggaagtctgg acagaccagt ggtggggctc gggtgggagg cactgggggg gctggagtgg    34920
aaagaatgtg gccacagatg acagcttcac agcagaattc agtgctaaga ggaagtgagt    34980
ggccatgagt tccatggtga cagaaagtct aagacaccca gcaaggcagg agtgggtgtc    35040
aactcaggga agcccagagg ctaatcctag gtgagagctg agggtgtcag ataagagcaa    35100
ggcaaggctc cggttctgga gcagtgaagg acatagcaga gctatgaccc aggaacaagg    35160
cccagcttat tgaaactggg cccagtcaca cagggtggca caggcaccaa gtagccaata    35220
ataataataa aaacaataac aatgatttgt gtctactggg catttattca tgttctatgc    35280
cagacactgg gctaagagct ttatatgtgg aaactcattt aatccttaca ataaccttat    35340
gaagaaggta catccaaaac cccattcttc taggccaggt gcagtggctc acacctgtaa    35400
tcccaatatt tgggaggct gaggcaagag gattggttga ggccaggagt tcaagaccag    35460
cccaggcaac atagcaagac cctgtctcta aaaaataaaa caaaaaccca ttcttcccgc    35520
tgcccaggga cacaccacta atgagtgtga tgggtgccta ggatgctgag cacctggact    35580
tcccagctca ttccctaaat gctgcacaat cagggtaact gtgccctgag cctaagaggc    35640
agtagtgagc tggcccatca tgtccactga tgaaggacac gtagccccaa cacaggggag    35700
aagtggtttc aggatcagca agcagggag gatgttacag ggttgccttg ttcccagcgt    35760
gctggtcact tgcagcaaga tggtgttctc tctctacctt gcttccttta cccacacgct    35820
atttctttgc agacttatgt gcacagtgcg gtgttggcag gaggcgtggc tgtgggtacc    35880
tcgtgtcacc tgatccctc tccgtggctt gccatggtgc tgggtcttgt ggctgggctg    35940
atctccgtcg ggggagccaa gtacctgccg gtaagaaact agacaactaa cctcctctgc    36000
tttggctgaa ggccagcagg acgctgggac ctgatgggcc actgtgcagt gcacagctgc    36060
attaggcagg tgtcggcgca ttctcttatt ggcttcaacg cctagtgagg gatccatcct    36120
ggctcggtgg cgcatttgtt aagatgctcg ggagcaggtg gcagaaccca tttgagcttg    36180
cttgggcatt ggggagaatt tgttatcagg ctactggggt gtcacagaac tcaaggacag    36240
ggactggagt gttgtgggga gccccgaagc ccctgtttta cttctttctt tgcttttcct    36300
gaatatctgc tttattctta ctctatagac atgcttcctc ctctttcacc ccacattgtg    36360
gggtgtagtc ttttgcttca agaaagcagc ctggtggatg gaatctcttg gccccaatcc    36420
caaattctct ggagaagggg ctctttggtt taacttggat aatgttgtct tcagctgggg    36480
gtgggcacat cgtgcatatg tggctgctgc cggggaacca cgtggatgat gtgagaggag    36540
cagcacccag aagagggagt gctgggctga tggtccaggt cgtgtccact tctgattgtt    36600
taattcttct tctaagtgga tggatctttc tccaatactc agcaaatcct gatcgttcca    36660
gaatacttca ttatagccaa ttggttataa tgtgcttctc taagagaaat atttagggac    36720
aacaaatctt catgggtttg aagacttgat ggaggaaaaa ggagtagatt ttcgaaggct    36780
ggatttggat gaacagggg tattcaggga gtgcattcca acctaaaatt aggaaaaact    36840
ggctgggcgc agtggctcac gcgctttggg aggccgaggc gggcagatgg cctgaggtca    36900
ggagttcaag accagcctgg ccaacatggt gaaacccatc tctactaaaa gtacaaaaat    36960
```

```
tagccaggca tggtggcggg cacctgtcat cttagcgact caggaggctg agacacgaga   37020
atcacttgaa cctgggagac agagcttgca gtgagctgaa atcgtgccat ggcactccag   37080
cctgggcgac agaacaagac tctgtcttaa aaaaaaaaaa agtggtttat atacagagtg   37140
gaatattatt tagccataaa aagaatgaaa tcctgtcatt tgcagcaaca tggatggaac   37200
tggaggtaat taaaaaataa aattaaataa ggaaaaacgt atcaatactt cgattaacca   37260
aaaccagggc aaatctgatt ttcatctttg caaggggaac aaatttcttt tatctcctct   37320
ggctttgaaa ccctgaaatg aaaggaggaa gggcagaaaa agaacacat agcaagttat    37380
catcagtctc agcgcccatc gcattccctg agcttgtttc cttgacttca tcactggcag   37440
gactattcaa aaatgattcg ctcattcatt catatattca ttcattcatc attccttcat   37500
tcaacacata cgttttaaca ctcatcttgc ttttcaagct atagtttagt gagcgaaatg   37560
gatacacaca atacagtgtg agaacagcaa gagggcacat ctgagctagc ctgggatggg   37620
tctggaaatg cttcctggag cagaggaaac ggttgacagc caagtgttga cagagaagta   37680
gtattagcca ggcagagaca tggggaatgt attccaggca gaaggcacag tgtgtatgaa   37740
agcttattgt taagaagagt gtgtggccca accaggaaac agacattcta aaggcatagg   37800
gtccacccag gagcatggtg gacccagatc cctgaaagat gggaggtgct caggcacact   37860
tcctgggcta gttgaggagt ctggatattt atttatttat ttatttattt atttatttat   37920
ttattgagac agagtctcat tctgtcaccc aggctggagt gcagtggtgc aatctcagct   37980
cactgcaacc tccacctcct gggttcaagt gattctccta cctcagcctc ctgagtagct   38040
gggattacag gtgcccacca ccatgcctgg ctaattttcg tgtgtgtatg tattttgttg   38100
ttgttgttgt tgttgttgtt gttgttgttg agacggtgtc tcgctctttt gcccaggctg   38160
gagtgcagtg gcgccatctc agcttactgc aagctccgcc tcccgggttc acaccattct   38220
cctgcctcag cctcctgagt agctgggtct acaggcgccc accaccacgc ccagctaatt   38280
ttttgtgttt ttagtagaga cggggtttca ccatgttggc cctgctggtc ttgaactccc   38340
gacttcaggt gatccaccca gtcggcctc ccaaagtgct gggattacag gcatgagcca    38400
ccgtgcccaa cctggatttt tattctgaag actaataggg attctaagga aggaaccagc   38460
ctgattgaat ttgcatatgt gtccacatct gctggctcac ggctgtgtgg gaggctgagt   38520
gatgggagg aaggattact gagtagggat ctgaaggtgt ggcctcatgc tttctttcta    38580
accagctgtg ttgtctttgg gatggtgctt aaatttgggc tagaccagtg ggtcttggtc   38640
accccccagg ggacatctta caatgtctgg aggcgttctt ggttgacaca gtggggtgag   38700
ggctgctact ggcagctcgt ggggagagac cagggatgct gcttaacatc ctacagtaca   38760
cagggcagcc cccaccacaa ggaattatca gctgaaattg tgaacagtgt ctacactaga   38820
cccttgctac tcatagtgtg gtccgtagac cagcagcatt ggcatcacct gggaccttgt   38880
tagaaatgct gttagacccc accccacatc cactaaagcc agctcttcat ttcaacaaac   38940
tccccgatga tgtgagtgca cattcaagtc tgagaagggc ttctttgagg tgagccttag   39000
tgcccatccc cctttggtgg ccccggatac caagggtgtg tgaaaggggt gggtagggaa   39060
tatgggtctc acctgccaat ctgcttataa taacacttgt ccacaggggt gttgtaaccg   39120
agtgctgggg attccccaca gctccatcat gggctacaac ttcagcttgc tgggtctgct   39180
tggagagatc atctacattg tgctgctggt gcttgatacc gtcggagccg gcaatggcat   39240
gtgggtcact gggcttaccc cccatcccct taacactccc ctccaactca ggaagaaatg   39300
```

```
tgtgcagagt ccttagctgg ggcgtgtgca ctcggggcca ggtgctcagt aggcttcggt    39360
gaatatttgt tggctgattt attcagaaat tctgtccagc ccctaccttg gatggattta    39420
tcacctctcc aggccacctc ttcttcccaa atagggccac ctaggtatag accaaagaca    39480
cgaaatcttt tgtgatccca caaacacaga gcaggtcaaa taggcccaag ccaattgaga    39540
ctgtggttca ggtcgtgatg cagagctttg ctgtggacgt gctcccactg cgtactagct    39600
gggcatgtgg cttaaccttt ctcagcctca gtcgcccat  tgtaaatgga gataatgata    39660
ctatctcccc tcacaggact gttgggatgc tactggattt aataagctaa tgcagggaca    39720
tgctaagcac aacccatccc tgaggcccag agaggggtgg gccttggctg aggtctcact    39780
gcgaggtggg aatgtgggcc tccagaccag aggtaggtcc tgtggcccct agacagtgga    39840
cagcaatggt cagtttgaca caccagagcc ctagccatta cttcctggat gttgtgtgaa    39900
tattttctgg acatggctta tataaaatga aaaagtgaat tgggcacgat acagggatag    39960 attttagag  atgaactggt agcatgatga taatcatatt cactgataac atttactact    40020
gttattgact gctttaaaag tgttgggcat tgtgctagaa accattatat gcattatctc    40080
cttgaattct cacaaccgcc tactgaggta ttctcagact ctaagaaatg agatttaaga    40140
gaagttatct gcccaaggtc actcggctgg aacctggctg taaaaatggc tgaagcaggt    40200
gatgaggagc tgatgcgttt ggacgtgtct cagagaaatc atggaggcgc tgcggttcct    40260
accggttctt ggatgccttc tacagagaca accatagccc caaattatag ggatcacata    40320
tcagtgggtg agacatcctt gcttgggatg aggaggggat gagctgtgtg aagcaaggcg    40380
cctctgtgat gggttccagt gatgtgtctg ccactgtctt aataactgtg caattctaag    40440
cagaaccttt cctgtctctg ggcctgagag ttccctctg  aaagatgagg acttgaccta    40500
gcaaggtcct actcacatgc ctgtagaaaa caggcagggg aagttagaaa aaaaaaaag    40560 ccagtgaagg aagggagctc ttcagcttgc acccatcatc acagtgcagg acccaggct    40620 cagtgttgcc agatccaatg acttctcaag agctcaaaat ctagagtttt gcatgtgctc    40680
tcccaagtac tggcagaaaa ttcaagattg ttagtaacac tgtgtggcta aattctgctt    40740
gtgggctgcc tagattccca attctgtgat tctgtggttc tctggaagca ttggttctcc    40800
acagcacctg catcacttgg aaacttgtta gaaatgcaag ccctacctac ggccccaccc    40860
cagacctacc cagttagaaa tctggggtg  ggacctatca gtccatgttt gaacaagccc    40920
cacaagtgtt ctcttgcaag ctcaagtttt agaaccactg acctatagcc aaaaaagaaa    40980
aagccaatca gtggttttct ggtaaaggat taacttaaca aactggcttt ccaagaaaat    41040
aaagccttga ttggtagcac ttgcaatttc tatggtacaa acgcttcccg catgactgag    41100
ttcaagctgt caaggagaca tcactataca tggacttggg aagagatgag aacaatcagc    41160
ccactgagcc tatgggaact ggctccagca catccctgca agtcaactct catcagggtg    41220
agtgagttga ggaccaagaa gcagttatcc tcttgccttt gcaggaccca ggcaaaggga    41280
agggcatagt gacagtgatg atctctcttc cggaagtctt tggtttgctg agagtaaaag    41340
gcgtgggctt caccagtggt gaagccagtc atgcagcctt agtcctggta ctgaaactct    41400
ctaaatctca gttttctatc tgtaaaatgg gaaataaga  cctatgtcac agggttgctg    41460
tgcagattta gcaacagaac atagccccgt tctttatgat gactgatgct gcatccgtat    41520
gaggacatct ctatgtaatg gaaagatgga gagaggatta gcgcaaagt  cacaacactt    41580 aatgggaact gtggattagc tacttggtgg cattgggcaa gtcagttgac tttgcattaa    41640
ttccacaaac aatatttccc aatttcctat tcagatgagc atatgtgatt gagtcagatg    41700
```

```
ctgtgatcag aaccaggatg gagcatttcc cacaaactgt gggatttttta agtaatggga    41760 aggcacactg aaatggcact gaatcatgca gttgcagata ctcttttca attctcagtc    41820 ctttgattac gtcagggaga aaagaaagtc cccacttggc ctgagaatct ctgcacccct    41880
ctagctcttg ttaaccactc ttttgaatag cagagaaaac ctcagactgc catatctggg    41940
agagatttta gcaacatttt gttttcattg tatctctttt tacagctacc tcccatttcc    42000
cttctatttc aagctagtaa ctcagttttc ttttaaattc aattatttaa atgtaaaaat    42060
aagtctattt ggagaaaaaa aattttaata gcatctctgg aatgccagta tggctaaatt    42120
catgaatgtt gtcctcaaat gctgaaatct gggaagcatc tggccaagct ttgtggacag    42180
gcctgcctag tttgaatccc aagagccacc cagtccaagc cacaaaacat tggaattctt    42240
ggttcacttc cctaacctga acttgccctc tgtgaaatag ggacactaat agctcactca    42300
cagggctgct gtgaggacat gtgttgagct gagggtctcg ccaggggaga ccctgtgcag    42360
ggagactgtt atcatggtga tggatttctg cttcattcat ttcttttcc agacagcatc    42420 atatagaatg agttgtgggg tggcagtcag caggtttggg tttatcctct attctgccac    42480
ttattactta aaaaaacccc aaaaaaccca acttatatag tataagctat atccagaaaa    42540
gtgcaaatat catacaagta ccatttgatg aatcttctga tatccccaca taaccaacac    42600
ccagaacctc ttcttgtctc attccaggat aaccactaac ctgacttcta acagcatcag    42660
tcagttttgt ctgttttgt acattatata tgtgatggtt tgaatgtgtc ccccaaattt    42720
catgtgctgg aaacttaatc cttcaattca tatgttgatg gttttggag gaagggcctt    42780 tgggaagtaa ttaggattag ataaggtcat ggggtgaggt atgatggcac tggtgactta    42840
taagaagaga aagagaaatc tgagctggca tgctcttgcc ctctcactgt gtgatgactt    42900
ctccatgtca tgatgcagca agaaggccct caccagatgg tggcaccatg ctttggact    42960 tcccagcctc tagaactgtg agctaaatca atttattttc tttataatca cccagtttga    43020
tattttgtca tagcaacaga atatggacaa agaaagaaaa ttaatgcaag aagtagagtt    43080
tttactgtaa cagattcctg aaaatgtgga agtggctttg gaactgggtg atgggaatag    43140
gttggaagag ttttgaggag caggctagaa aaagcctgta ttgtcaagaa tggagcatta    43200
tgccaggcac ggtgtctcag gcttataatc ccagcacttt gggaggccaa agcaggtgga    43260
tcacctgagg tcaggagttc gagaccagcc tagctaacat ggtgaaacgc tgtttctacc    43320
aaaaatacaa aaaattagct gggcgtggtg gcgcacacct gtaatctcag ctactcagga    43380
ggctgaagca ggagaatcac ttgaacccag gaggcagagg ttgcagtgag ctgagatcgt    43440
gctattgcac tccagcttgg gcaacaagag caaaactcca tctcaaaaaa aaaaaaaaag    43500
aaagaaaaag aatggagcat taagacagt tctgcagttc tggtgagggc ttaaaggaag    43560
accccagaac tagggaaagt ctggaacttc ttaatggtta ctgaagtcgt tgagatcaga    43620
gtgctgatag aaatatggct ggtaaaggcc attctgatga ggtctcagat agaactgaag    43680
aaccacgtgt tggaaactgg agcaaaggtc atcctttta taaagaagca aagatcttag    43740
ctgaactttt tctgtgccag agtcatttat ggaaggcaga aaatctgtag gtcagccatg    43800
ttgtagggaa tgaaagaaca ttttcagctg agaacactga gagtgtgaca caactaccga    43860
ctgataagaa aactagtaca cataaattag ccaggcgtgg tggtgggcgc ctgtattccc    43920
agctacctgg gaggctgagg caggagaatg gcatgaaccc gggaggcaga gcttgcagtg    43980
agccaagatc gcgccactgc actccagcct gggcgacaga gcaaaactcc gtctcaaaaa    44040
```

```
gaaaaaaaaa aggaagaaag aaaattagta cacatagaac aaagccagag gctgttcatc   44100
aggacaaggg agaaaaactc caaagccatt tcagagatct tcaagactgc cctcccatt    44160 actggcccag agctctaaga gggcagaatg gtttggaatg accagctgct gcccagggct   44220
gccttgggtc tctgctcccc acatttctgg tgcagcattc ctcagccatc ccagctgtgg   44280
ttcaggtggc cacaggtgtg atgtggaagg taaaagtcat aaaccttggc agcatacaca   44340
tggcactaat tttgcaggtg tgcagaatgc aaaagctgag ggggcatgcc ttcttccacc   44400
tacatttcaa agggtgctgt gaacagccac cccagagagc cctagtaga gcagggtcta    44460 gtggagctac aagggtgggg ccaccgccaa gaccccagaa tggtagagct atcatagtgc   44520
aatgccagct tgggagaact gcaggcatga gactccaacc tgtgcgaagt gcaacatggg   44580
cagaacccag caaaccaca ggggcagagc tccccgaagc ttcggggggtc caaattccat    44640 agtgtgtcca ggaggtggca cacagagtaa aagatcattc tgaaggttta aggtttaatg   44700
ttgttttcta tgttgggttt tgtactttcc tggaaccagt tacccttttt cccttgcctc   44760
tttttccttt tagaatggga atgtctgtcc tatgcctgtt ccactgttgt atttttggaag  44820 tcaataactt gttttgactt tacaggctta cagccagagg gaatctccca tagaatgaat   44880
tgtaccttaa gtctcaccca catctgattt agatgagacc atggactttg gaattttgag   44940
ttggtgctgg aacaagttaa gactttgggg gttgtctaag tgtggtgttt catgcctgta   45000
atcccagtga tttgggaggt tgaggtggga ggattgcttg agcccaggag ctcaagacca   45060
gcctgggcaa catagtgaga cctgtctcta caaaaaataa aaataaaaaa attagccagg   45120
tattgtggca tatacctgta attctagcta ctcaggaggc tgaggtgaga ggatcacttg   45180
agcccaggag tttgaggctg cagtgagcta tggtcgtgcc actgcattcc agccagggca   45240
acagagtgag actctgtctc tacaaataaa attagctgga tatggtggca                45300
cacatctgta gtcctagcta ctcaggaggc tgagacagga ggattacttg agccaaggag   45360
tttgaggctg cagtgagcta tgatcatgcc actgcattcc agcctggatg atagagcaaa   45420
atcccatctc taaaaaaaa aaaaaaaaa aaaaaaaaa aaaaacttt agtgctattg        45480 gaatgaattt tgcatgtaag aaggacatgc attttggggg ctgggcagg atgctgtggt    45540 ttgaatgcat ccctcaaatt tcatgtgttg gaaacttaat ctccaaattc atatgttgat   45600
gaaattggag gtgaagcctt tgggaggtaa ctaggattag ataaagtcat cagggtgggg   45660
cccctatgat gagactggtg gcttacaaga ggaagagaga actgagctga catgctcttg   45720
ccctcttgcc atgtgatacc ctctgccatg taatggcagg cacagcaaga aggtcctcaa   45780
cagatgccag cagcatgttc ttggacttcc cagcctccag aaccatgagc tatatatact   45840
tattttacaa attacccatt ctgtggtatt ctgttatagc aatagaaaat gaactgagat   45900
aatatacatg gaatcataca gtaagtctgt gcttttgtat gcttctttta ctcaacattg   45960
tagttgtgag attcatccag gttgttaagc attgctgtac ccttttttcca ctgggatata  46020 gtgttctgtc atgcttgggt cttaatttat aaaggtgact gagtggcatt tcttccagt    46080 attattggaa ggaaagttttt gttgttcaca gttcccctgt aaacaagagg cagaacacgt   46140
catgcagggc cacacaaaac tgtatcatcc agggaccagg cagcagaaag agaggggaa    46200 ctgggactat gcctttatga aaaagagtgg tgggagagta actgggtgag gcatccact    46260 aatgggcagg aagtgaaaac acatatgtta gaatttgtag ctgaggggtt tataatatga   46320
gtttcctatg cctgagaaag ctgacttgca agaaaatgag ataaacaact ttggccatta   46380
gtgtggccct gtcataaatg aatgccagat aggcaaatag agaatctaag aaaagatagt   46440
```

```
tggaacaagt gttccattgt gtgaatgcag cagaatttat ttatccatta ttgaggagga    46500
tttgggtagt ttccagtttg gagctattat gaatattcta gtattgctcc tatgaacatt    46560
ctagcacttt tattttggga gcacacgaat gcacttctgt tgattatatg cctagaagtg    46620
aaattgttga attatacagt attcacacag tcagctttag tggctactgc taaacaattt    46680
tctctagtag tttgcgccaa tctaatcacc agtagtgtat agaagctcct tttactccac    46740
attttgccaa cacttggtgt tttccttctt tttgattagt catttagcaa tcaaacctat    46800
tgtttacatt ttgatatctc caataactaa ctaaatggag cactttaat atgcttttg      46860 gacagttgaa tatcttttct tgtgaaatgt ctattcaagt tagtttgccc attttctatt    46920
gtggtgttct gtcttttct tattgatttg taggaattcc ttacgtatcc tggatatgaa     46980
tcccactttg tgcgttacct ttttccttct ttctttcttt ttgaaacaga gtctccttct    47040
gtcacccagg ctggaatgca gtggcgctat ctcagcccac tacaacctct gcctcccagc    47100
ttcaagcaat tctcatactt catcctcctg agtagcttag attacaggcg catgccacca    47160
tgcccagcta acttctgtat agacaaaata attttggta gagacagggt tttgccatgt     47220
tggacaggct gatcttggac tcctggcctc aactttggcc caccttggcc tcccaaagtg    47280
ccaggattac aggtgtgagc caccatgccc agcccacctt ttactttctt aatggtgtct    47340
tttgaacaag agaggttctt aattttaata tagcccaatt tatcattgtt ccctttatgt    47400
ttagttcttt tatgtccttt ttaagaattt ttgcagccag cgcggtggct cacacctgta    47460
atcccagcac tttgggaggc tgaggctggc ggatcacaag gtcaagagat cgagatcatc    47520
ctggccaaca tggtgaagcc ctgtgcctac taaaaataca aaaaattagc tgggcgttgt    47580
ggctcttgcc tgtagtctca gctactcggg aggctgagat cacgccactg cactccagcc    47640
tggtgacaca gcaagactcc atctcaaaaa aaatttttt ttgcaaggtc atgcatatgt     47700 cccctgatt ttttcctaa aaatcactta ttattagatc aatgaattga gtaattgact      47760 acattttca gtcattcaac aaatatttcc ctgaggtttt gataacctga actgtgtttg     47820
gagctgggga ggaagcaaac tattgaagat atacaaagat ggcaaagatg agggcctgga    47880
gcttgccaca cggaagggg gatggctgcc tgaatggttg gcaggtagt tgttgacatc      47940 tgcactccct acatgagcag cagggtggca actctttta tcttttaat ttattttct       48000 tttcttctt tctttttttt tttttgagat ggagtctcgc tgtgttgccc aggctggagt     48060
gcagtggcgt gatctcagct cactgcaaac tccacctccc aggttcacgc cgttctcctg    48120
cctcagcctc ctgagtagct gggactacag gcgcctgcca ccactcccgg ctaatgtttt    48180 gtattttag tagagaaggg gtttcactgt gttagccagg atggtctcca tctcctgacc     48240
tcatgatctg cccgcctcgg cctcccaaag tgtgggatt acaggtgtga gccaccacac     48300
ccggccttaa tttatttttc tagtctgcag gtaattcttt ttaattctct ccactctcct    48360
atgatcttat gaggtaggga ctgtcattat ttctcccact ttataatgaa caatcagtaa    48420
agacagggaa gataaccaaa tgacatacaa ggtggggtcc accccatgag gctgcaggct    48480
tggagctttg ctttgtctta aaaatgagaa catgagctgc ccacctgttg agacaagaaa    48540
caggaaaggc ttaaaaaact ggcttgttat gtacaactat ccgtgggct gcagtgaacg     48600 ggctggcagt gcccaggtgc aggctgaacc ctgggacaat cacattcagc atccaagggc    48660
ccccgtaata gcttaatgtt tgaattgaac ccctgggggtt gccttgaagg agagaggtcg   48720
tggaagtatg ttcaaggggt agggatgggc aggggagatg ggtctgaaag ccaagctcta   48780
```

```
ccccacccac cttgccccaa gagaaataga accttcatct ttaattgcct aacgagaaaa    48840
ctggggctgg ccagatgtgg tggctcatgt ctgtaatccc agcactttgg gaggccgagg    48900
cgggcagatc acttgaggtc aggagttcga gatcaccctg gtcaacatgg tgaaacccecg   48960
tctctattaa taatacaaaa attatccagg tatggtggcg catgcctgta gtcccagcta    49020
cttgaggcac aagaatcgct tgaacctggg ggacagaggt tgcagtgagc cgaccactgc    49080
actccagtct ggacgacaga gtgagactcc atctcacaaa caaaaacaga aaaaaaaaaa    49140
aaaaaagag agagagagaa aactggaggc tctgagaggt tgagggactt gcccagggtc     49200
ttgcagctag taagtgacag agctgggact tgagcttggg ttttctgact cctggtctgg    49260
ttcattatcc atgaggtgct gggaactaaa ataagccaca atcttggaat ctccgtcgcc    49320
tccctccctc ccacatgtct gcgtggcttt tgggaaaat gccaggggaa tgtaccagcc      49380
agggagagga cccttgtttt cctcatggcc cttcctggca atggcactac tgacaccgac    49440
agtccttttt gtccctgatg acctctgctg cctgatgccc aagtgaccac ctctgctttg    49500
tcatttctag gattggcttc caggtcctcc tcagcattgg ggaactcagc ttggccatcg    49560
tgatagctct cacgtctggt ctcctgacag gtcagtgtga ggccacctttt cttccaccat   49620
tgccaggaca cagcacccac gtccagagcg caccctgccg tgtggctgga tgtctatgtg    49680
ccccatctcc ttccctgagg atcacataat ttcagaattg gaaaggttct tagaggtcac    49740
ctgctgctaa tgtggactgt gaggccaggg cagggaaggg acatccctga ggttataagt    49800
agggtgagtg gcaacgttgc agacttttga acccagggct ggtgatcaca ctcagttttg    49860
cacagaagcc cgagaaaatc cttacaccca aaagcctacc ttttatttct gaggacaccc    49920
ataatactat tttattcaac agatatttat tcaatatcca ctatgagcca ggcactgggg    49980
acacagcagt gagcaaaaca aattccctga ccccatggaa ttgaccttct agtgggggaa    50040
ggtattagca ataaatagac aaataagtgt ctactacgcc agatgggaag aagtggctgt    50100
gaagacagag caaactagag aaacatagag tcaatgtggg atggggtgtt cttttagggg    50160
ggtggtcagg gaaagcttat ctgagtagtt agcttttaag cagagacccc aatgaagagg    50220
agggagatat gcgatgcatt tagttagggg aagaacattc catgaaaata ggatagcaag    50280
tgcaaaggcc ctgagacagc agcatgcttt gtgtgttgag ggaacagtaa ggagaccagt    50340
gtggttggtg tgaatggagt gagaaggagc agcagggggtt gagggcagaa tggtagtgag   50400
gagcaggccc ttataaaaga tgggaagcca ctggagatct ttcaacaaag gggaaaagta    50460
tgtttctgtt cttgcaataa aatagaacag caaaaaatct aggggagttg ctaattagcc    50520
agttttactt atatgccagg tgaaaatatg tggctaggtg cagtggctca tacctgtaat    50580
tgcagcagtt tgggagaccg aagtgggcag atcatctgag atcaggattc aagaccagca    50640
tggccaacat ggtgaaaccc catctctact aaaaattaaa aataagccca ggcgtggtgt    50700
tggatcccag ctacttggga ggctgaggca gtagaattgc ttgaaccegg gaggcagagg    50760
ttgcagtgag ccgagactct gtctaaaaaa aagaaaaaa agaaaataca cattcaggcc     50820
aggtgcagtg gctcacgcct gtaatcccag cactttggga ggctgagaca ggtagatcac    50880
ttgaggtcag gagttcgaga ccagcctgac caacatggca aaaccctgtc tctaccgaaa    50940
atacaaaaat tagccaggcg tggtggcgtg tgcctgtagt cccagctact ggggaggctg    51000
aagtagggga atggcttgac cccaggaggt ggaggttata gtgagtcgag gttgcaccac    51060
tgccctccag cctaggtgac agagtgagac tgtctcaaaa aaaaagaaa gaaaatatac      51120
attccatcca gaactgttca cctttattct acaagcaaac atctttttatt ggttagacac   51180
```

```
ccatatatgt gtccctaagc aggaggtgaa tgccaaataa gagacaaatg gcgtaagaca    51240
ctatgagttg tgtgacgttg ggcatgtcac tttactccct ctgagccttg gttagcttct    51300
ctgtaaaatg aaaggattat ggtaactaag ctggcttcct tccagcttta acaaactgta    51360
tggaggtact ttttggagtt acctgggtaa tttttgagtg tgagattggc tagaattgct    51420
ttaatatacc atgtctggcc ttagcttttt gcagagtctt tgtgaagaag cagaggcgga    51480
gtagcgttaa ttccgtaagt taacgttcag ttcgtggcag ctggcaatcc aaccctggga    51540
aaggctgccg gatttagcaa aaatgcaagg tgtctgtttt taaatttgaa atgaattggg    51600
tatcctgcat tttatttggc aaccctgtcc tgggactcac actattcact gttatcactg    51660
gtatgttcaa agtggtgctg acttgccctc tgtcttgcaa agtaccagga ggtcttttct    51720
tattcttcac tggagtcaaa aaagagaata gaggaaaaga caatcatatt gttcctttaa    51780
gagttaagac caacaagttt tcttctttac atgttgtttt tgacatgagc aaactggtga    51840
ttaaaaacaa cttgggtggc tcatacttgt aatcccagca ccttgggaag ctgaggtggg    51900
agaatagctt gaggccagga gttcaagcca gggcaacata gtgagacccc atctctacaa    51960
aagatacaaa aattagccag gcgtggtggt acacctgtag tcccagctgc tctggaggct    52020
gagatgggag gatcagttga gcttgggagg cagaagttgc agtgagctga gatcatgcca    52080
ctgcactcca gcctggacaa cagagcaaga ccctgtctca aaaaggaaa caaaacaact    52140 tggacaatgg aaggggaaa aagttcctca agcagccaaa attgcaccaa atggactccc    52200
agaagacaag catttaattt gttaattgag ccctctatgg gcctgtctgt atttatttaa    52260
gaaacaatcc tatcaagcat agttattggg tttctcagcc caggtagatt agaaatagca    52320
gattagaggt gggctaggtt tctagaggta aagtacacca gcagaagtta gaagtgaaag    52380
caaagagcct aacagaggaa gagaaattct ttttttttc ttttttaga cgcagttttg    52440 ctcttgttgc ccaggctgga gtgcaatggc gctatctcgg ctcactacaa cctcagcctc    52500
ctgggttcaa gtgattctcc tgcctcagcc tcccgagtag ctgggattac aggcatgcac    52560
caccacaccc ggctaatttt gtatttttag tagagacagg gtttctccat gttggtcatg    52620
ctggtctcga actcctgacc tcaggtgatc cgcccacctt ggcctcccaa agtgctggga    52680
ttacagggat aagccactgc gaccggccga caaattctta aaactggaca caagaacaca    52740
aaacgcttgg gctgctgaga gattagaaca acaaccctcc acagctacac acctttttcca    52800 cgttatatgg cacgttataa gtgggtgttc ctagtgatgg ttctgatttt ttttaaaaaa    52860
agtctaaata tgtttaatgt tgtctcagaa gacaaaatat attttagaca gatattcctc    52920
agtgatgagt aagcctcagc tatctggaaa attcatgcag gcgccagaga tcgttactga    52980
gtaattcaag ctaactgcgt catgctggtt gtacccctgca tgccaatatc agctaaaagc    53040
agcaccacga aagggaaata cgaatctcac taagcactcg cccattcttg ttaacgacac    53100
tggaactgat catccttaat aatacacaga taaatctatc aggagcattt ccttgcttcc    53160
tgtgaaagga agcactcatt ccatgtgtcc tgtgaaattc atccaacttc aggaagctgg    53220
aggaatacat atggccaagc tatctgggca gagagtagac agggaatgga ggttgggcac    53280
agtggctcac acctgtaatc gcagccattt agaaggcaaa ggcgggcaga tcacttgagc    53340
tcaggtgttc aagaccagcc tgggcaacat ggctaagtcc tgtctctgca aaaaatacca    53400
aaaactgagc tggatatggt agcacacacc tgtggtccca gctacttggg aggctgaggt    53460
gggagggttg cttgacccccg ggagtttgag gctgcaatga gctgtgattg tgccactgca    53520
```

```
ctccagcctg gataacagaa tgagactctg tcccaaaaat aaaaaataaa atcaaagaca   53580
cttaaaaaga tggggaaaag gaaggacagg cacttaagca agttataagc tactttccta   53640
actacacaag tggaatctta agctgaggtt cccaggagtt gactggagcc agagaagaca   53700
gacctatagg agcacccaat tggagtcacc ctccatagta gcccatatgt cttacatgga   53760
tcagctttcg tgggccctt ttactccatc tggggaaggg cgtcagatct gtggctctca    53820
tgtactgctc agtacactgc cattcccagt tctttttttc aaaaaaaaaa aaaaaatgtc   53880
tacagaatcg gccaggtgtg gtggctcatg cctgtaatac tagcactttg gaaggctgag   53940
gtgggtggat cacctgaggt cgggagttcg agaccagcct ggccaacatg gtgaaactcc   54000
atctctacta aaaaaaaaaa aaaaaaaaa attagctgga tgtggtggca ggcgcctata    54060
atctcagcta cttgggaggc tgaggcagga taatcgcttg aacctgggag gcagaggctg   54120
cagtgagccg agatcacgcc attgtactcc agcctgggcg atagagtgag actctgtctc   54180
aaaataaata aaataaaata aaataaaata aaataaaata ggctacagaa ttaagctggt   54240
ccaggaatga cagggcttcc atttatttgt ctttcaattg tgggagaaaa aggatttctg   54300
ttgagatact gtcgttttga cacacaatat ttcgattaat cttgagatta aaaatcctgt   54360
gctccaaatc ttttaacatt aaattatgca tttaaacagg tttgctccta aatcttaaaa   54420
tatggaaagc acctcatgag gctaaatatt ttgatgacca agttttctgg aaggtaagat   54480
ttttcaccta ttaacgtgat agattttgag tgcatgaact taaaaacata cctgagtata   54540
tatgttgact tgctgtttat gagtaaaaca aaaacaaaaa tggagtaagg agcattgcag   54600
gaggaactag aggagaaaca aatccatgat atgcatgtgt gtggggagg gtggcgggga    54660 ggtggtaaag gtcaccattt ccctgatacc tcaaattcat tcagagtcag ggatgagaca   54720
gctttcactg gccacacttc ccctccccct atctgcagtc ctcagcgtag ccaaatagtc   54780
tgacatgcgg gtgacagaac cccacaatgc aaaagctgga agaaacctca gccttggag    54840 tccaaccccct tttttgacag atgctaagag tggagacatg acttatcaag atcttacaac   54900
tggctgggca cggtggctca cgcctgtgat cccagcactt tgggaggctg aggtggggcg   54960
atcacctgag gccaggagtt cgagaccagc ctggccaacg tgtcgaaacc ccatctctac   55020
taaaaataca aaagttagct gggtgtggtg gcacatgcct gtaatcccag ttactcagga   55080
ggctgaggca ggagaatcac ttgaacctgg gaagcgaagt tgcagtgat ctgagatcat    55140 gccactgcac tccagcctgg gtgacagagc gagactttgc ctcaaaaaca aaacaaaaca   55200
attgtacata tttaaagtgt tgtaaccaag tgagttacag agaaacacca cactttgagc   55260
ctaattcagg agtcctttat tagccggcga cctagagacg actagtgctc aaaattctct   55320 cggcccccaaa gaaggggcta gatttttcttt tataccttgg tttagaaagg ggagcgggaa  55380
ttgagctgaa gcaatcttac agaagtaaaa caggcaaaaa agttaaaaag acaaatggtt   55440
acaggaaaac aaacagttcc aggtgcagga gctttaaagc catcacaagg tgacaggtgc   55500
gggggctctg ggtgctatct gccggacaca aacgcagggg cactagagta ctatcacccg   55560
ggcaaattcc tgggaactgc ggacacagct tgccacagta ccttatcagc taattgcact   55620
ctttgatgtg ctgggagtca gcttgcacaa gttaagtcct tgaggaaggg ggtgggtaag   55680
gagcccttaa cgtcttgcaa atgaaggagc cgaatggaat ccctccggct ttcttagcta   55740
agagagagtc aatcaagtta atacaagtta gggtatcaca aaagtatata atttgataca   55800
ttttaacgta tttatacact gaagagacca tcaccaccat caagacaagg agcacaccca   55860
tcacttccac acacttcctc ctgctccttt gaaattcctc cctccctacc cacctggtcc   55920
```

```
cacccaaagg caaccactga actactttct gtcactaagg tttgcatttt ctgtaatttt   55980
tttgttttgag acagggtctc actccgccac ccacaccgta atgcagtggc accatcatgg   56040
ctcactgtag cctcaacctc cccaggctca ggagatcctc cccctcagc ctcctgagta    56100
gctaggacca caggtgtagg ccaccatggc aggctaattt tgtattttt ttgtagagat    56160
ggggtttcac cgtattacct aggctggtct cgaactcatg ggttcaagca atcctcctgc   56220
cttggcctct caaagtgctg ggattatagg catgagccac tgtgcccagc cctctgtaat   56280
gttacacaaa gggaatcatg cagcacgtac tgcccttggt ctggcttctt ttgctcagca   56340
tgattattct gagaatcatc cgtgttgttg cgtgtaactg acttcatcag cttctctctg   56400
cagctgtcag ctcttggctt ctcccaacag ccaatctctc tttatcccct gcaagtgttc   56460
ttgcctattt agcagaatca aggtactcta tcgaaaagac tcggaaaatt ggtttaatct   56520
attcattcat tcctcaggta tttatcgaat aactattcta taccaagtac tatgctaatc   56580
aaccaaggac agcacaaaca ggagaaatct ccagctcagt cacttgagtt gcaataaata   56640
tttgctggat aggtcaggtg cagtggctca cacttgtaat cccagcactt tggggattac   56700
tgagacggga ggatctcttg agcccaggag gccaaggctg cagagaacca tgatcatgcc   56760
actgcactcc agcctgggtg acagagtgag atcctgtctc tgaaaaaaaa tatttgctgg   56820
ataaattaag gaaatctgac gaaccccatc agtagccatt gcagcaacag gtaaactaga   56880
acgagtgtga atttggaatg aggaaacccg atgttggcca tcattctgta atgtcatgta   56940
ttatgtaatg tattatatat taatgtatgt attatgtagg caagttcctt gacctctctc   57000
actggtaaca taagagtagt aatctttgtg ctacttcact gggttatttt aaagatcaag   57060
tgaggtaata atgtctgtaa caacattctg taaaatgcaa accgccacat gaatgtgaaa   57120
gtttattact agggatttag ccaaccacaa gggaatgtgt gagcataaga gctatcatat   57180
tgcaagccta cagtttctga ttttgtgcta ggtgcttttc cacattacct gattttatcc   57240
tcacaacagc cctgcataaa agtaagtatg tcgcccaggt gcggtggctc atgcctataa   57300
tcccagcact ttgggagccc gaggtgggca aatcacttga gatcaggagt ttgaaaccag   57360
cctggtcaac gtggtgcaac cctgtctcta ctaaaaatac aaaaaaaat tagacaggcg   57420
tggtggtgga tgcctgtaat cccagctact gggaagctg aggcaggaga atggcttgag   57480
cccgggagat ggagattgca gtgagatgag attgcgccac tgcactccag cctgggtgac   57540
agagcaaggc tatgtctcaa aagagaaaaa aaagtaagt atctcagtct tgaagatgat   57600
gaaatggagg cctagagaga ttaagtaact tgcccaaaat gacagaacta atgcatagaa   57660
aagaagaaat gtgatgtctt ttggctccaa agacacccca catatgcgtt ggttacagtt   57720
actagagaaa agttattcca ccccaccccc accccagaa atcttctgac ttgttttctc    57780
gcagttgagt aggaccattt attcggcagt gtaccattct cagcttgcag ttgaaagcca   57840
aatatccatt aaagaggcaa ggatgcaaac ttgctaagct gataaatcca ggggtgattt   57900
tttttttttt tgcaaaccat ccaacaagac attttaaata ctcattgaat ttcatagaac   57960
tgactgccag gattggaaag acattaaagc cagctcagcc actgcctcgc tggttggcca   58020
gaccacgcct ggcacttctg ggagggagca ctcaccaccc cccaagggca cccatctcat   58080
cctccgaagg tttatgaaaa tgcactcatc atttgctaat tcattccact acgtgtatta   58140
cctaatttgt gacacgatgt gaagtaccag agagataatt ctaaataaaa tatagttatg   58200
ggtctcaagg agccagatat gctaatctcc tatcctcctg cagtttacag tggtcctcac   58260
```

```
cagatactta tttacaaaaa ttcagtttat tatttatttt tttgagacag agtcttgctc   58320
tatagctcag gctagagtgt aatggtgtga tctcggctca cttcaacctc tgcctcccag   58380
gttcaagtga ttctcctgcc tcaacctccc aagtagctgg gactacaggc acctgccacc   58440
acggctaatt tttggagttt tagtagagac agggtttcac cacgttggcc aggctggcct   58500
cgaactcctg acctcaggtg atctgcccac atcagcctcc caaaatgttg ggattacagg   58560
cgtgagccac catgcccggc caaaacttca gtttataaca caatcttttca cgtgtcttct   58620 gctttcatta aaagaataga cagttccctt ctttatttca gtttaataaa ccatggattt   58680
tatttcatgc tttgcaaaac acaagggctc actgacatgc acttcttaaa ctaattctgg   58740
ctggtcgcct gtaattccag cactttggga ggctgaggcc gacagatcac ttcaagtcag   58800
gagttcaaga ccagcctggc caatatggtg aaaccacgtc tctaccaaaa atataaaaaa   58860
ttagccaggt gtggtggtgc gtgactataa tcccagctac tcaggggcct gaggcagaaa   58920
aatcacttga acccgggagg cggaggttac agtgagctga gatcgcgcca ctgcactcca   58980
gcctgggcga cagagtgaga ctctgtctca aaaataaat aaatacaaat aatgtaaaat   59040
acgaaacaag caatcctggc agtagctgct ggaatgagag gagggagagg tcataggag   59100 gtcggggaca atggagcatg gagttgtgtt ggatttggct aagcagcagg aagtgcaagg   59160
cattccaagc aagaggaggg gggcaggtgg ggagcatctg caagaacaga agcagcatga   59220
gcaacctggc tcggcagtgt gtgaaaaggc tgaaggtgg ctagagccac ttcaatttca   59280
tccttcaggc aaatgggaaa ttcccaaagg tttgagtggg gaagcaatgc ctacaatgaa   59340
agtttgagag tgaagcagag tgatcgaatt aagcatgtag gccgagttct gaaataactg   59400
caatgtgctg aagatcatcc attggcttct gaatgagtat ttgcagttta ttttttaaaa   59460
tgattttatt gccaagaaag ataaacacta ctgttttggt acaaaaacat aacaaaatgt   59520
gttgagtccc tcttgctgtt ttacgcgaag ttttaaaaat ctactcttgt cacagtggta   59580
tcacccctac ttctgatttc aaataaatgt tctagagaca cagtaagggc ccaacaaacg   59640
cttgttcaac aacacaagga gagccagctt ttaaagtagg aaaacaggcc gggcgccgtg   59700
gctcacacct gtaatcccaa cactttggga ggctgaggtg gcagatcac ttgaggtcag   59760 gagttcaaga acagcttggc caacatggtg aaaccctgtc tctactaaaa acacaaacat   59820
tagccaggcg tggtggtgca caccagtagt cccagctatt caggaggctg aggcaggaaa   59880
atggcttgaa ctggggaggc agtggttgca gtgagccgag atcgtgccac tgcactccag   59940
cctgggggac agagggagac tccatctcaa aataaaacaa aacaaaacca aatcatacaa   60000
aaacattagc tgggtgtggt ggtgcatacc tgtaatccca gctacttggg aagctgaggc   60060
agaattactt gaaccctgg ggggaggttg cagtgagctg agatcttgcc actacactcc   60120
agcctgggca acagagtgag gagactctgt ctcaaaaaat atatatatta aaaaaagaa   60180 aaaaaaagt aaactaggaa aacacatcag cagcctgcca acagactccc ctagcctcgg   60240
tgagggccag tgttctggga ggcagatctg aattctagtc ctagttcacc cactggcagg   60300
ctggtgccct tgggcaggtc gcttctctgg ggctcagttt cttcctctat aaaatgagat   60360
caaatcccat gttctaagag tttgtgctct ggagtcagac agatctgggt tctaccactg   60420
ccagctctgt gatcttgtag cttcagtctc gtcatctgac atggagataa cagtaactgt   60480
ctcactgtgt tgttagggtt taaaggagat aatgtatgtg aaatgttagc aaacaagtgt   60540
tagctaccct gatttccggt ttcagagttc tgtggtccca gttatgccca catgcagtga   60600
cgttgtatgg taggctgtgg tgtggcacca cttcagaact cagcgcatgc acagcttgca   60660
```

```
gaagagaagg ccagaggaga cctaagaagg ctcttcgaac acttgaaaga ccggcatgta   60720
ggccgggcgc agtgactcac gcctgtaatc ccagcagttt tggaggtcga ggcgggtgga   60780
tcacctgagt ttgggagttt gataccagcc tgaccaacaa ggtgaaaccc cgtctctact   60840
aaaaaataca aacattagct gggcatggtg gcgggtgcct gtaatcccag ctactccggt   60900
ggttgaggca gaattgcttg aacccgggag gcagaggttg cagtgagctg agattgcatc   60960
actgcactcc agcctgagac aagagcgaaa ctccatctca aacaaaacaa acaaccaacc   61020
aaacaaaacc aaaaaaaaaa ctggcatgta gaagaaaaat acttttctc tacacttctc    61080 caaagaattt aactaggccc aggggaggtg cagtataaat ttctaacaat ctcaactgtc   61140
tgccaaatgg aatgagctac ttcatatggc agtagtgagt cctctgtctt tggaggcatt   61200
caaataaaag ccagatggcc atttatcaac aatccatgta aaacgttaga tgaaataaaa   61260
cctatatatc caagatctct tccaattcag attttatgaa agaatttcta aggtctttgt   61320
aatgagacat ttaggctgtt tcaagagatc aagccaaaat cagtatgtgg gttcatctgc   61380
aataaaaatg tttgttttgc ttttacagtt tcctcatttg gctgttggat tttaagcaaa   61440
agcatccaag aaaacaagg cctgttcaaa aacaagacaa cttcctctca ctgttgcctg    61500
catttgtacg tgagaaacgc tcatgacagc aaagtctcca atgttcgcgc aggcactgga   61560
gtcagagaaa atggagttga atcctttctc tgccactctt tgaggagaat ctcaccattt   61620
attatgcact gtagaataca acaataaaat acagccatgt accacataac aacatcttgg   61680
taaacaacag actgcatata tgatggtggt catccagtaa gctaaggtta atttattatt   61740
attccttgtt tttttttttt tttttttttt tttgagatgt agtcttactc tgtcacccag   61800
gctagagtgc aatggcacca tcttggctca ctgcaacctc tacctcctgg gttcaagcaa   61860
atctcctgcc tcagcctcca aagtagctgg gattacaggc acccaccaca tctggctaat   61920
tttttgtatt tttagtaaag atggggtttc accatgttgg ccaggctgat ctcaaactcc   61980
tgacctcaag tgatctgccc gcctcggcct cccaaagtgc tggaaccaca ggcctgagcc   62040
actgtgccca gccttgtttg ctttttaac agataacagt gtgctcatag aaactgcttt    62100
gacatgactg caatcatgtg cttcatagaa acttaattag attataccac tagagtcttc   62160 agattttat actttttttt tttgaaacgg agtctcactc tgtcaccagg ctggagtgca   62220
gtgccgcaat ctcggctcac tgcaacctcc gcctcccagg ttcaagcaat tctcctgcct   62280
cagcctcccg agtagctgga attacaagtg cgcactacca cacccagcta attttttgcat  62340 ttttacttga cagggtttca ccatgttggc taggatagtt tcaccaggat ctcttggcct   62400
catgatcagc ctgcctcggc ctcccaaagt gctgggatta caggtgtgag ccaccgtgcc   62460
cagcctatac ttccctttt gaataccatt tggtgttttg aagaattaac agctttgtga    62520
acgtggcagt gcttgtgatt caggcttcca ttgagaccaa ggggagaacc tggttgcagg   62580
acaaacagac ggacagcgtg tggcagtgtt taaatgctct tctgaaggct gatacgacag   62640
ctctctgtgc actgattgca tatgcatccc aagattatat tattgttttc tactgctatg   62700
tgtcacactt tgccaaacag gatgtggaaa atgaataagc ggttttctta ggcacttctt   62760
aacagacaat tggtcaaaat gaactccatt gcttaagaaa cacataaaca ccatttagtc   62820
actgaacata gctatatgta tggttgttac tatgggaaat cttgttttgc caattttctt   62880
tgaaaattct ggcagaccaa ggttcttttt gtttacataa tacttgaaaa ataaaaatga   62940
acaagctaac aaactaccaa gttttcactt acataaatgt agttgcatac agaaaatgtg   63000
```

```
actgtgaatt aatttttcta ggacttttaa actataagca ctatttgcac aaaagagaac    63060
caatctatca attacaaact cacataattt tacagatttt ttttttccta cacagcacat    63120
aaaacagaag gaatttgaag ccaccctcca aacacagggg aaggaggctg tgtgtatatc    63180
ctcattgtct ttcacattct aaggtggttc cactcagtga ctgaaatcct taagcgttgt    63240
attagtctgc ttgggctacc ataacagcag cttaaactgt tgtttagcca ctcagactta    63300
aacaacagaa atttatttcc ttatagttct ggaggctgga agttcaaggt gccggcaagg    63360
ttggtttctg gtgagacctc tctccctgtc ttgcagatgg ctgcctcctc cctgtgtcct    63420
catagagcct gtcttctgct tttacacttc tggtgtcatc ttcctttttt ttttttttttt    63480 tttttttttt ttgagacaga gtctcgctct atcgcccagg ctggagtgca gtggcccgat    63540
ggatctcggc tcactgcaac ctctgcctcc caggttcaag caattctcct gcctcagcct    63600
cccaagtagc tgggactaca ggtgcccacc atcatgcctg gctaattttt gtatttttag    63660
tagagacagg gtttcaccat attggccagg ctggtctcga actcctgacc ttgtcatctg    63720
cctgcctcgg cctcccaaag tgctaggatt acaggcgtga gccaccgcac ccggcctctt    63780
cctcttctta taaggacacc agtcctatta gattagggct ccaccctcat aacctcattt    63840
gaccttaact attatttctt taaagcacct atttccaaat atagtcactt tagggggttag    63900 ggcttcaaaa gatgaatctg agggagctca attcagtaaa tagcagtagt cattaatgga    63960
caatgtatac aaagataatt tcgtgattac tgtccttatg cataaacgtc ctcagtgttc    64020
cactgcgttt atccagattt agtatcacaa agactttgct ctgagaaaaa tgtgattttt    64080
tttttttttt tttttttgaga cagagtcttg ctctgtcacc caggatggag tgcagtggtg    64140
caatctcggc tcactgaaac ctccgcctcc caggttcacg ccattctcct gcctcaatct    64200
cccgagtagc tgggactaca ggcgtccgcc aagatgccca gctaattttt tttttttttt    64260 tttttttga cacggagtct cgctctgtta cccaggctgg agtgcagtgg cgcgatctcg    64320
gctcactgca agctccgcct cccgggttca cgccattctc ctgcctcagc ctccggagta    64380
gctgggacta caggcgcccg ccactacgcc cggctaactt ttttgtattt ttagtagaga    64440
cggggtttca ccatgttagc caggatggtc tcaatctcct gacctcgtga tccacctgcc    64500
tcagcctccc aaagtgctgg gattacaggc atgagccacc gcgcccagca gatttttttt    64560
tttttttttg agatggagtc ttgctctgtt gcccaacctg gagtgcagtg ttatgatttt    64620
ggctcactgc aacctctacc atgttcaagc gattctccca cctctgcctc ccgtgtagct    64680
gggatcacag gcacacgcca ccacacctag ctacttttg tatttttagt agaaatgggg    64740
tttcaccatg ttggccagga tggtcccgaa ctcctgacct caagtgatcc tcctgcctcg    64800
gccttccaaa gtgctgggat tacaggtgtg agccactgtg cctggccaaa aatgtgatttt    64860 cttatttccc acattgccaa ttccatttca attaactata atagctatgt ctattgagca    64920
ctcaagcgta ttctagaaac tgttcctgat tctggg                              64956

<210> SEQ ID NO 23
<211> LENGTH: 65624
<212> TYPE: DNA
<213> ORGANISM: Homo sapiens

<400> SEQUENCE: 23
acccttggcg tggacacatt tccagggagg gaccggagga cctcctacct cattggtcac       60
tgccagtgac tgagcttgac tcaggtagga gggcatggca ggtattctca gggagtctgg      120
tgtttacaga aaagtcatga ttacacgtga aagctgtggg ctccctggct tgattcacca      180
```

```
cacctgcagg aagcctggct gctcagacca gcacgccgtg gacatagcac cacttgctca    240
gcttcatttc cgtaactcag gctgccaggc ctgctgacaa attttcacgt ttgtaataac    300
cctgtgagga gaccagagta catcttactt gactcataag gaaattgaga ctgggtgatt    360
tagtaacttg ggaggcagaa ttgcaaagtg attagcaaca caagccatgg tgtcagatgg    420
atctgggtta ggtcccacct ctgccgttta ttagctgtgt ggctttgggt actcacgcca    480
cctctctgag cagcagtttc ctcttttgta agcgtaatga tgcctacact cacaggcttg    540
agaggaagat ccgatgaaat agcatatgca aaatgattgg ttccgtgctt ggcattccag    600
aaatggtagc tgttattcag ccaacaaata tttattgagc acctactatg acttccctg     660
gtgctgagga tacaacagca accacagcag tcaaaagtcc ctgtctttat gttgctcaga    720
ttctcatagg ggaaagcaga taatgaacaa atacacggcc agacgcagtg gctcacgcct    780
gtaatcccag tactttgcga ggccaaggtg ggcaagtcac ctgaggtcag gagttcgaga    840
ccagcctagc caacatggtg aaaccctgtc actactaaaa atacaaaaat tagcgcagtg    900
tggtggctca tgcctgtagt cccagctact gggaggctg aggaaggaga atcgcttgaa     960
cctaaaaggc agaagttgca atgagccaag atcgtgccac tgcattccag cctgggtgac   1020
agagtactcc atctaaaaaa aaaacctaaa tacacaagta aaaatataga cttcgtcaga   1080
tgctagtaag tgctgtgaag gaaactaaaa ggggaacaca aggaacccctt gtcaagggga   1140
gcagaaaggg gagttgatgc tgtccttta aatagggcaa tcagaggcca ggcacagtgg    1200
ctcacactta taatcccagc actttgggag ttcgaggcag gtggatcact tgaggtcagg   1260
agttcaagac cagccaggcc aatgtggtga accctgtct ctactaaaac tacaaaaact    1320
agccaggtgt ggtatcgcgt gcctataatc ccagctactc gggaggctga ggcgggagaa   1380
tcgcttgaac ctgggaggcg gaggttgcag tgagccgaga ttgtgccatt gcagtccagc   1440
ctgggcaaca agagcaaaac ttcatctaaa aaaaaacac agcaaaaaag ggcagtcagg    1500
gaaaacttcc ctgagaaggg gatggtggag tacagatcca gggaggtgag gtggggagca   1560
agccagtaca gttgttcctt gactttcgat gaggttatgt cctgataaag ccatggtaag   1620
taggaaatat tgtaagtcaa aaatgcattt aatacaccta acctacggaa catcatagct   1680
tagtgtcacc taccttaaac atgcttagaa cgcttacatt agcctacggt tgggcaaaat   1740
catctaacac aaagcctatt ttatgataaa gtattgaata tctcatgtaa tgtactgagt   1800
actgtacgga aagtgaaaga cggagtggtg ggatgggaac tctaagcacg gcttccactg   1860
catgtgtgtt gctttcgcgc catcataaag ttgaaaagcg ttaagtcaaa ccaccgtacg   1920
tcggaggcca tctgtatctg gtaggaggag tgtttcagac agagagaaca gcaggtgcaa   1980
tagagtgctt ttttcccagc attttattat gaaaaatttc aaacatctac caaaaaaagt   2040
tgaaagactt gtacggtgaa aagccataca tctcacagct agaatcaaca attaacattt   2100
tactgtattt ggttttgac ttatctatcc tagatccctt gtgctttctg tagcaggtga    2160
cctgccttga agatttaaag acagaatatc gggaaatgta gtcagaaaat ggggcctttt   2220
ataagagtca gaggggaaga gcaaaaactc tgctttcgag aaatctgtcg ggagaggcca   2280
actgcaggga tacctcccct tttaatgaa agcatttctg ttctgcgagg agcgggatcc    2340
tcttgtcaag cagtcagtcc ctgctgcttc cttactgggg caggatcagg acgcacaggg   2400
atttggagtg ccttggaacc aaccaccacc cacgctgttt gccagctggt aaacatgcct   2460
gtcaggtcta ggggttggca ttgcctggaa atctttagtg ttcatcttgc tgacatctgg   2520
```

```
tgccctcggg taggtaggtg cagttggctg cctggtttac agagcttgta ctgggcccag    2580
gttagcaggg gtcacatccc tttatcccac tgtgcagggg agttccttct caggaaaccc    2640
agtttataag aagtactgac tgccagaaat agagcagaga tcagaaccag gaggcaattg    2700
tgagaggaat ggagacttct gacctctggg gattggggta ccctccccct taattgctgt    2760
tggggtagca gagggcttag aagcccatgt tcctagactt ttagaattgg aagaagactt    2820
agaagtaatc taggctgggg gtccccaacc cccaggctgt ggcccgttag gaacctgacc    2880
gcacagcatg aggggtaggc cagcgagcac taccgcctga gctccgcctc ctgtcagatc    2940
agcagcggca ttagattctc acaggggcac aaaccctatt gggaaccgcg catgagaggg    3000
atctaggttg cgtgctcctt aggagaatct aactaatgcc tgatgatctg aggtggaaca    3060
gtttcatccc cacaccatcc ctccaacctc accccggtcc atggaaaaat tgtcttctac    3120
aaaacccgtc cctggtgcca aataggttgg ggaccctga tctaggctac agttaagtgg    3180
tcaaacaccc aggtcctgaa gttaggctgc ctgggtttaa atcccagctc tactgcttac    3240
tagccctgtg accttgagca agtcacttag ttttctgtg cctcagttta ctcatttgta    3300
ataaaagctt aatagtaccc atcccagtgt catgaactaa gttcatatat gtaaagtgct    3360
tagaatggtg cctagcaagt acttagtaac agttagctct gaaaatgtat aaagcaaaat    3420 taccaatgt tttagtggtt tgcagccaac ttttttctat gcgtgtgcta acatattatt    3480
ttataagagt gggaatatat tgtacatgct gttatataac ttgcttttc actaaacagt    3540 ctatcctctg tgtcagtttt gataaaagcg ttttcctctt gcttttcctg catatgttca    3600
gaaccatcat attggtagca agtttcatgt cctgcagttt tcttaaccaa cccctgcta    3660 gcggacattt aggttagtct cagttttttc cttctgtaaa taaagctgca ctgagcaaga    3720
agtgaccgat gccaagtgac tagatgacct taggtatgac ctctctgggt cttggtttct    3780
tggtctaaaa acaaaatgac aggattcgac tgggtgatta aaatctcctc tgatctacat    3840
aggaattgtt ttcaagacat ttctgcattc ctcagtgac agggtgctca ctacctcatg    3900
agtatttcag tggacaactg taatggtcaa taaagtatcc actttccacc ttccacttcc    3960
ctgtagctcc tggccctggc tttattctct ggggctccac acattcagtt tacactcagt    4020
ggccagtggc tggggccatt gtagaaaatg aggaaactcc aattccttcc ttctttttctt    4080 cctctttcat cccttcctcc ctccctacat ccctctctct cttccttcct tccttgacac    4140
ttaccatgta ccagaccttc tgccaggcac atggatggga gcacagttcc gggaagttgg    4200
ctgcagggtt agaactaagt cccaagcccc gtaaagctca tgccagggga ctggactgtc    4260
cagtactgag ggatggggat gctgaggctg gtggccttcc tcagatgcac tgtagtgccc    4320
caggcagagt cctgggctgc cctgtgagga ggtgaccaga ggtagagcaa cttcacccta    4380
aggctggatc aggatcccct ccaggttttt actagagcca aacccacatc tcctttctct    4440
tctgccaccc cccttaaaa tgcttagaaa cacatagatt taaatacaag ttcaaatgta    4500
agtaatttca actgtgtaac tatgaggagt caattctacg tgggtcctat ctgtatcctc    4560
cccagggctc agctccattc tttgctttca ttcattctca ttcaatacat tgttgttaag    4620
agctcactgg gtgccctctc tgtcatgtag taaggtttta aaagaaagc ctcttctgag    4680 cttcagtttc cttatttata aaataggagt attgatccgt tccttgcttt tcttacaagg    4740
atatgctgaa gatgactgaa gtacagagta aagaaggatt atgtttgggt gtcaaaggaa    4800
tagaatgccc tctttcaaac tgagcacagc aggaacctgt aacaggaaca cagcaacttg    4860
ttgaatgaat gacaatattg gaaaacatac atttcctccc ctccccatca tagtccctct    4920
```

```
gcttccgtgt taactccata gacaggccag cacagccagc cttgcagcct gagataaggc    4980
cttTggcggg tgtctcccct atcgctccct caagccctca agtaggtgtt ggagagaggg    5040
gtgatgcctg gtgctggtgg aaccCctgca cagagacgga cacaggatga gctctaagta    5100
cccgcggtct gtccggcgct gcctgccCct ctgggcccta acactggaag cagctctcat    5160
tctcctcttc tattttttta cccactatga cgcttcctta gaggatcaaa aggggctcgt    5220
ggcatcctat caaggtgaga gttcattgga acagtggtca caggagcaaa tagcaggggc    5280
aggggcgggg gaggcctatg gttctccagg ggcacagatg ttcctttcta caaaatcccg    5340
aggaaaagat tcccccatct tcttccgtag attgcaccga aattcagtca caatgtaag    5400 ctttccttta gaagcagcct gggcatgccc tcttctgtga agcctgcctt gattttcag    5460 cacagtgaga ggcatcctct ttggtgttcc tcaaattccc tctaccaaat ggtcttcata    5520
attctctgct tctctgcttc cccttctctc tccttagtgg caaggatttt ttttatttt    5580 atagatttag gggatacaag tgcagctagc ttatgcaagc aatttcatgt tgttgggttt    5640
tcgggttttg tttccttttt gtggcctctc gctcatttct tatttctttt tgagacaggg    5700
tctcactctg ttgcccaggc tgaagtgcag tggcatgatc atggttcact gcagccttga    5760
cctcctagtc tcaagcaatc ttcccaccTc agcctcccaa gaagctggga ccacaggagg    5820
gcaccaccat gcctggctaa attttttttt ttttttggta gagatgtggg tctccctgtg    5880
tttcccagac tggtctcaaa ctcctggaca caagcgatcc tccagcctca gtctcccaaa    5940
gtgctggaat tacaggcgtg aagcactgtg cccagctctc ttgctcatat ctatactagt    6000
tttcttttgg aagcttcagc ctgttgctac cccccacccc cacccccacc gaccccagct    6060
ttcttctcac ttaggggctg ggaagtctgc atgctgtcta taaatccaga accagaaggt    6120
atggctgaag gggagggtag gatgatggtt attttatatt cagctaaaaa tattcccaga    6180
ctgtgatgag acaactgtaa ataagacaga tgtccacaat ggtgtgactt tgctttttta    6240
aaaatattga aatgagtttc aggcatctca gtgggctgat aggttgttga taatggacag    6300
ggcctccttg aagaatgtcc ctgagacaaa gttgaagctt gagcctggtt gagtgcttgc    6360
ttgttcctag gttgatatga acggctagtt aactggaagc aaagagaagt catcctgggg    6420
gccatggcag tgacaagtag gacttaggga gggaagccct tataccattt aaggtgctgg    6480
cccagagagg agccttcagt gacagacaaa caagagctgg cacaatttta attcatttca    6540
atttacttta attcatttca atccaataca attcaatgca ttccattcat tcaaccatgt    6600
atgacatcca atgtgggatc cagacacatg atgattagaa ctgatattta tgagcactta    6660
ctatgtacca ggcactattc tacatgcttt acattgaacc ctcacaataa cccaatgagg    6720
tgggtactat tatgatcttc gttttttcata tgaggaaact aggcatatgg atgttgagta    6780
atttgcccaa ggtcgctcag ctagcaatag cacagcgtat ttaaatttag ccaccctgga    6840
tttagtttcc ttacacttaa ccattatgca tcatggcccc attttacagt ggcgttgagt    6900
catttgtcat ataacccagt aggtgtagca gccactattc caaccctgta gattgactct    6960
agggtccatg ttctttaccc ctgcaccgtg ctactaacgt aggtacaaaa tgtcctcaga    7020
aactcacttt atatggaagc tcagaggagg gtccacaacc caggcagggg agacgatggt    7080
gtcaggggag gcttctggag ggaggtgcct gcccagccag ctcttgaagg ctcagtagga    7140
attacctgtg ggacaaaggc gggtcatcca agtgagggca cagtgggtgc cattgcgtgt    7200
gcacacacta gagcagactg agcttgggct taacattgca ttgccctgta gcctaaaaag    7260
```

```
agaagcaagg ggctgggcga ggtagctgac acctgtaatc ccagcacttt gggaggccaa    7320
ggctggagaa tcacctgagg ttaggagttc aagaccagcc tggccaacat ggcaaaaccc    7380
catctctact aaaattataa aaactagccg ggtgtggtgg cacacgtctg taatcccagc    7440
tacttgggag gccattacac tccagcctgg gcgacagagc aagacttcat ctcaaaaaac    7500
caaacaaaaa caacaacaac aacaaaaaac aaagaggaga gcagggactg ggtgtggtgg    7560
ctcatgcctg taatcccaaa cactttggga ggccaaggcg ggcagatcac ctgaggtcag    7620
gagttcgaga ccagcctggc ccatatggtg aaaccctgtc tctactaaaa atacaaaaat    7680 tagccgatg tggtggcacg tgcctgtagt cccagctgct gggaagctg agggaggaga    7740 attgcttgaa cccaggaggt agaggtagct gagctgagaa tacgccactg cactccagcc    7800
tgggtgacag agtgggactc tgtctgaaaa aataatagt aataataaa aataaacagg    7860 gaagcagtgg gtggtagact cactgggctg catacgagt ttggcttcag tctgaggtcc    7920
gaatagtaaa caggagcgcg acaagtttgg gtttgggtca tggcggatgc catgccaggg    7980
ctggtgttgg gcacagggga aggggcatgg cttgagacac aagaccagcg tggaggctgt    8040
agtgtagtat tgacccgagg gcttcaacct tctgatggtg tacacaccat ttttgagca    8100 tgtaccatgg ttatatgtta cactttaagt attactacat taatatattt tgtatgttat    8160
aataaataca tacaaattag gaaaattgaa agagatcaga atgaaatata taatattttc    8220
aaattactaa tcataatggt gtcaatctcc aggcagggtc cattgctaca gttgacgata    8280
gtggatgaaa attcactcct cagagtcttc ttgataattt gaaattgtct tgattgactt    8340
gtcagatctg attagatcga cattttttaa atctcgaatg tgactgacag cttgtacaag    8400
gagaagtttc actctgcctt tccttttgt tcacttgact gccattattt ctctgcttcc    8460
aatctgtgtt tttctgcacg agttggttaa gccattactt cattttgtga agtttgttg    8520 agttaaactt aggtaactta atctgtcaat ccacttaatt gaattcagtc ctggtaaact    8580
ataatagatt attcaaacct gccaattcta aaaagacatt ttgagacaat caggaaatct    8640
gaatatagca tgaatatctt acgatataca aggattattg ttaatttgt taggtatgat    8700 aaaagcatgg tgggtttttt ttttgttttt gtttttaag gctctatctg ttagagaggc    8760
acattgaaat ggcatgatat ctggggtttg ctttcatacc agaaaaaga aaaagtagag    8820 aaggattata gaaacaagat tggtctcatg tgacaatcat cagagtttgg agatgggcac    8880
gtagggtcat cgtgctgttc tctctgtttt catatatgct ttgaaagttc tgtaatagtt    8940
aattaaaaaa aaaaaaaaca ccctggctga gcacttaggg aggccaagtg gggaggattg    9000
cttaaaccaa gaagttcaag accagcctag gaaacatagg gagaccccc ccgccatct    9060 ctaaaaaaaa aaaaaaaaa ctgtaaaatt taacccagtg tggtggcaca tgcctgtagt    9120
cccagctact cagtaggctg aggtgagagg cttgcttgag cctgggagct tgaggctgca    9180
gtgggacggg attgtaccac ttcactccag catgggcgac agagcaagac cctgtctcaa    9240
aaaaaaatga aaatatttga ggtgaagcga gactgtaata acaaatttaa aaatataaat    9300
aaaacataaa ggctgggtgc ggtggctcac gcctgtaatc ccagcacttt gggaggccaa    9360
ggcaggcaga tcacgaggtc tggagatgga accatcctg gctaacatga tgaaccccca    9420
tctctactaa aaatacaaaa aattagctgg gtatggtggc gggtgcctgt agtcccagct    9480
acttgggagg ctgaggcagg agaatggcgt gaacccagga ggcggagctt tcagtgagct    9540
gagattacac cactgcactc cagcctgggc aacagggcga gactccatct caaaaaaaaa    9600
atgaaaataa aataaataa aacataaaac cctgccatta gttgcaacat gaagaatata    9660
```

```
gagaaatgcg tatcaaatcc ttctcattgg accaatattc ccttagggca ccttccaaag   9720
ctaggagact caaggctgta tgacatcctg agcaagtgag gggtggcttc tgggtgaatc   9780
tgaatattaa atatttgcag aattgaaaac ttcacaaagt acctttagag atagaatagc   9840
ctagatccat gtttctcaaa gtgtggtccc cagacctgct gcctcagcat ctcctggaaa   9900
tttagtagaa atgcagattc tcaggcccta ggccagacct actgatcaga agctctgggc   9960
ctggggccca gcaatctgtg ttttcacaag ccctctgggt gattcttctg tgcgtgaaag   10020
ttcgagaatt cctggagcta gactgattca aatcttgcct ctgtatctta gagaccttgg   10080
gcagattagt caacctcttt ctgcctctgt ttctacttct gtcagaggat gatagtactt   10140
gtttcattaa gttgttgaaa ggataaatga attgacacac ataaagagta ttagctttta   10200
ttatcaaaag cttttttttt ttgagacaga gttttgctct tattgcccag ggagtgcag   10260 tggtgcgatc ttggctcacc gcaacctccg cctcccaggt tcaagtaatt ctcctgcctc   10320
agcctcccga gtagctggga ttacaggcat gcgccaccac gcccggctaa ttttgtattt   10380
ttagtagaga cggggtttct ccatgttggt caggctggtc tcgaactccc aacctcaggt   10440
gatccacccg cctcggcctc ccaaagtgct gggattacag gcgtgagcca ccatgcctgg   10500
cccaaaagct ttaatttctt aattttttaa ataaaataaa taaaactaga attgcttgtt   10560
ttcttccagc tacccggtg attgtattga gcattttctg gggtgtgtgt tctttgctgt   10620
aatgactact ggtctggatg acctgtgatg agaccagatg ggcaggggca gtggaggaga   10680
ttctagagat atttaggaga taaagtcagc tgtacttgat gaaagagtg gggagttaag   10740 actggctgca gatgtatgat ttggcataga gaggtgccag ttcctgaggt gagagacaga   10800
aggggaggga caggttgtga ggatgaatga acaatgatat gttcattctg ggcttggagt   10860
taaggggcct atgatatgct taggggaagc agagagtatc aattacctat tgctgcataa   10920
cagccacccc aaacttagtg gcttaaaata gcaaccttt aatttactca tgatcatgat   10980
tctgtggtgc aacaactggg ctgggttcag ctgggcagtt cttctgttag tttcacccag   11040
ggtcattcat gcatctgcag tttggggtgg gatggcctca gatgacctca ttcacatgtt   11100
tggcaattgg tgattcactg ggggccatta ctgtaacaat cgcctaccag gcagagcttc   11160
cctaaggcta ccaaactggg agactatcct gggtcctgtg ctgtggatac cactcagtcc   11220
cccatcccca cccatactc ctcaaaggca gagagaggg ctactagaag acagaggagt   11280
tttcccagtg acatgtaaac actccaaacc ctggcacctt ccacactgca gctttggtct   11340
gcccctttgg gaaatctctg tttttcttcc caggctgctg gagggtgag agtcgccggt   11400 agagtagagg ctgtgggcga ggaggtggcg gcctcctgag gctgcagtgg tctttccagg   11460
cagcagtggg agcacagggt ggaggtcaac cctagagcct gggggagtga agctggttct   11520
gccttcagag ctcttggtgc tgaagtttct gcaggccaga gggagggca agagtgggag   11580 ggggtgcaga tccagaatca cagaggcagc tgaccgagg aggcagctgc caagggat    11640 ggactcagaa ggccaaagtg ctgttatcca aacgaactct ttgcaagtgg tctctttgca   11700
acaggcctgg gggagagcag tcttgcctaa agtcacaccg ctaatcagcg gccggcacgg   11760
ggtaacagtt actaacactc actacgtacc caatgctggg caaagtgact tgcatgagcc   11820
agcgagctca atgctcatgg caatcctctg agcagctggc attgtttcat ctcaattta   11880 cagctcagga agctgggaca cagaggaaga gccaggctct gaacactgac aacctgattg   11940
agagacccac actgttcatc accgttacgc tatatatgct gtatagaaag gcaggatggc   12000
```

```
ataatggtta aacctaggta ggtagggttt gaatcctcct gctaccattt actagctctg    12060
tgacttggac tagttatagc acctctctgt gcctcccttt cccctctct aaaatgggga    12120 taataaatcg tacctcctac ctgaggctgt tgtgggctaa gtctgtaagg cacgtagaac    12180
agtgcctgga acgtgggta ctgtctatct gtgtgcctgc tgttacaaca atggtgagta    12240
ttgccttatc tctcgctgct gaactaccag gttagacttc tttctgcaag tcatgaggct    12300
ttcataaact tttcctgaag gctttccgta gaatgtacaa ttcccctctg ggcccaggca    12360
tgggcgcccg ggtaggacat ccacttctta tcacccctga acaccttaga gcccatcagc    12420
ttatcaaacc agcagctgat gtgagtgcag agcagactgt gagaggtgga ggctgatacc    12480
agtgaggatg ctccaagctg ggacccagcc ctgaagcggg agcccagata atggacgggt    12540
ggaaatgggc ctggagccca agagaggtgg gaggatgagg gggcagggg aggagaagcc    12600 tgaaatcaaa tgttatttcc tgaccagttt ggggtgcatg agctctgtca acagctcatg    12660
gaaactgctg ccctaatttc atcttgttgg ctgaggcaca attcctctct cagggacagt    12720
gtagagcctt ggggaggaag gccctgagcg catatacctg gaatcaggga atcgggatca    12780
ggggcagcag ctgtgcccga taaagccccc acccaggatc ctctgacttc ctcatctctc    12840
tttttttttg agccggagtc tcactctgtc atccaggctg gagtacagtg gtgcgatctc    12900
ggctcactgc aacctcagcc ttctgggttc aagcgattct cctgcctcag cctcctgagt    12960
agctgggatt acaggcatgc gccaccatgc caggctaatt ttgtattttt agtagagacg    13020
ggatttcacc atgttggcca ggctggtctc aaactcctga cttcaagtga tctgcccacc    13080
tcagcctccc aaagtgctag gattacaggc ataagccact gtgcccggcc ttttttttt    13140 tttttttttt ttttttaaa aaagggtct ccctctgtcg cctaggctgc tggagtatag    13200
tgatgtgatc gtggctcact gcagccttaa ccttctaggc acaagccatc ctcccacctc    13260
accctcctga gtagctggga ctacaggcac ttgccaccac gcccaagtaa ttttgtattt    13320
tttgtagaga caaggtcttg ctatgttgcc taggctggtc ttgaactcct cagctcaagc    13380
aatcctcctt ccttggcctc ccaaagtgct gggattacag gtgtgagcca ccacacctgg    13440
tctgacttcc taatctttag ggccccaact ctgcccttat ccaggcaact ctcctctccc    13500
catcttccac taacttcttt ggaatattcc agagctgtaa aagccttaga gagtatcaag    13560
tccaactcct atgtgttaca gacagggaaa ctgaggccta aagagggtaa tggacttgcc    13620
taagatcgct tagtgaggtg agagaagaaa gagctagaga cagcctagcc tgtgcaagga    13680
catagttcca ggcattcaga gctgcgctct gctgccggca tgtttggggc ctggtagtta    13740
gttcactgct gaactaccag gttagatttt cttttctccaa gttgtggggc tttcataaac    13800
ttttcctgaa ggtcttcctt acaatgtaca attctcctct gggcccggtc atgagcgccc    13860
ctcacaggct ctctctggtc cccttctgta aaatgagagg aaaatggaag aattgctcta    13920
ctcatggaat cttcaataag tctgaccct atgcatatag cattgctaca aaatggcaga    13980
tgcactttaa caatcgtgtt taataaaagg ttggatttgc atatctgaag tggggcatgc    14040
agtctccaac tgaacacaag cctcactgct cccacatgtg cactgcacct tcatatacat    14100
atttcctgct tggctcctga gggaatttga gtaatcccaa gaggaacccc tgtagaaaat    14160
gtcccctggt cacacacccc cattcctaag gatgcaagca ggagatagaa acattccctg    14220
cacctccctc cttgctgtca gaagaagtgc aaagagttga atccttccta atgcccactt    14280
ctcacccacg ccccaaatcc ccaggtcccg tggaggtcct tgggggtctc ctatatcctg    14340
gtggtgtcag gttgatttgg aaatgtcagt gtcctccctt gtcctctctg gcagaccctg    14400
```

```
ggtgtgtgta cgtttcaatg gaagtgaatt taaatgtact ttataaatca aagactttt   14460
ctgagacttt ggagagttcc agtaatgaga gcttctcatt gttatcaaag ccagggctgg   14520
agaccagtgg caggtgagtt cctattgctg tgattgtcat gatgatgttg atgaacagcc   14580
actatttatt gagtgttctc catgtgctag gcactgtact aaacattatt tccttcggat   14640
gtcccagaaa cctctcaggt ggctctaatt acccttattc tgttgataag gaaagtaagc   14700
aacttagaag accacagggc tatgaagttg aaacacgtaa attgatattt tattttattt   14760
atttatttat ttatttattt tgagacagag tctcactgtg tcgcccaggc tggagtgcag   14820
tggtgcggtc tcagctcact gcaacctccg cctcctgggt tcaagcgatt ctcctgcctc   14880
agcctcccga gtagctggga ttacaggtgc ccgccaccac atccagctaa ttttttttgta  14940
attttagtag agacggggtt tcaccatgtt ggccaggcta gtctcgaact gctgacctca   15000
tgatctgccc acctcatcct cctaaattgg tattttata tgtccaaaag agtcaactgg   15060
tggcaattta gtgaggttta atctaatagg aaatgataga gctgggatcg aacagagcta   15120
tgtgaactca aaacctatgc ttccccttcc accttttcga aaaacattgt ctaggctggg   15180
cacggtggct catgcctgta atcccagcac tttgggagac ggaggtgggt ggattacatg   15240
aggtcaggag ttcgagacca gcttggccaa aaattagcca ggcgtggtgg tgcgcgcctg   15300
tggttcccac tgaagcacag gaggctgaag cacaagaatc acttgaaccc gggaggcaga   15360
ggttgcagca accgagatcg cgcaccactgc actccaacct gggtaacaga gagactctgt   15420
ctcgaaaaaa aaaaaattgt ctacatgctg gttcagaaa atttaaacac taaaactaaa   15480
aaagtaaaac atctcccaaa gttagagaca atattcatga tgggaaaaaa aaaattcttc   15540
aagatttctc tctctccagt catttattca tgtgcgaaaa cagttggtga ttattgataa   15600
gaagagggag ggcagatggt gtggtagtcc aaggcacagg ctccagcaga ttatctaggt   15660
ttaaatcttg gctgtaggcc aggccctgtg gctcatgtct gtaatcccat cactttggga   15720
aaccgaggtg ggcagatcac ttgaggtcag gagtttgaga ccagcttggc caacatagtg   15780
aaacccctc tctattaaaa atacaaaaat tagccgggca cggtggtggg cacctgtaat   15840
cccagctact gggaggctg atgcaggaga atcacttgaa cccaggaggc agaggttgca   15900
gtgagccaag atctcgccac tgtactccag cctgggtgac aagagtgaaa ctctatctca   15960
aaattaaaaa aaaaaaatct agctctacc caccggggca agttacataa cgcctctgtg   16020
ccttggtttt catatctgta aaatggtgac agtaacagca cccatgtcaa agtgtggttg   16080
tgagaacgaa acaagatagt ctatgtaaag tgattaaaac agcgtaggca catggtaaac   16140
gcttaggaaa tgtaggctgt tataaagctc agagatgtta agtaactaga tcaagaccac   16200
acagttagag agtgccacag tcttgatttg aacccaaatt tgtctcgttc tggagctcaa   16260
gctgctaacc cttttttcaaa actggaatta aaccaaagtg ctcaccctcc gctttgctgg   16320
gccctccct gccctcaggt gcatctcttc cactcacctg ccacagcagc ctctgctcag   16380
ggtctgagac tgggaaaggt gagggctacc caggtggccc tgatgttttc tgccagccag   16440
ctcaccaggt ccctcgcagc aggcggcaaa gggagggagg tttgctgtga agattatgtg   16500
gttcccaaca acaagagcac tgggcctatc tctgccctct cttttctgtg tgtcctggga   16560
caagtcactt ggcttctgtg gctttatttt ctcatgtgcc cagccagggg gttggccctc   16620
atatgcaata acagcagcaa tgaccttac tgagtgtcca tgtgcatcaa gcacgtgtac   16680
tttacacttg ttcttattat taggtttaat aatagaataa ttgccacatt tactgagcac   16740
```

```
tcattatggg ccaggccctg ccctaagtgc ttaattagct ttagctcctc taatccttac   16800
cttatcccca cacggcatgt tatgttatcc ccattattca gttgagaaca ttgaggctca   16860
aagaggcaaa gtaacttgac caaatacttg taaacgatct tgcatgcccc ttccagctgc   16920
catttagtaa gactctaatt tcataccacc ctaaatctcg tctgcttccc cctcctcctt   16980
ctcaccatct ccccaccgag cagtcggcca agatctgacc gtgatggcgg cccttggctt   17040
gggcttcctc acctcaaatt tccggagaca cagctggagc agtgtggcct tcaacctctt   17100
catgctggcg cttggtgtgc agtgggcaat cctgctggac ggcttcctga gccagttccc   17160
tcctgggaag gtggtcatca cactgttcag gtattgggat ggtggctgga tcacttctgg   17220
gtcatagagg gaatggaccc cgaaaggaca ggttccagaa gatctgggat attgccccct   17280
ctctgtctag caccagtgct gtgcaatatt taggacatcc ttatgctaaa agattattca   17340
ttgtttaaaa ttcaaattta actgggcatc ctgtatttta ctggacagcc ctactctgtg   17400
tatcacaagg aatccaggcc tacattcctc ctgcatcctt tctttcctgt tattgtcgat   17460
tatgattttg taaagttaca taatcagtat aagtttatgg aaaacgtaag aaggaaacac   17520
gttagacaga gagaaataga catgccacac ctagagagac attctatttt ttttttttct   17580
tttttgagac ggagtttcgc ttttgttgcc caggctggag tgcaatggcg ctatctcggc   17640
acaccacaac ctcagccttc tgggttcaag cgattctcct gcctcagcct cctgagtagc   17700
tgggattata ggcatgtgcc accacacctg gctgattttg tattttagt agagataggg   17760 tttctctgtg ttggtcaggc tagtctcaaa ctcctgacct caggtgaccg gcctgcctcg   17820
gcctcccaaa gtgctgggat tacaggcatg agccaccgcg tccagcctga gagacattct   17880
cttgaaaaga aaggactttc agccccctaa agctactaga caagaaatag ccatgccttt   17940
attttcatta aattacctgt gctttgttta gatgcctttg tgtgaaatgc taagaaccat   18000
cacaactaat gtatggtgcc agaagtcaga atagtggtta cctgggcagg aggtggatat   18060
tgattaggaa ggaacacaaa atagcccat ggggtgcaga aaatgttctc tgtgttcacc   18120
tgggtgatga ttacacatca agctatacac attttaaaag ggcattggca cttaatagaa   18180
ggaactaggc taaattttttt cctgaaacat tgttttgttt tgttcaaacc tctgaatctc   18240
tcagctcccc agatgatggt aaacgtcatc ctaggcatct tagggacctc tcaaggcctc   18300
tcaaggccat tccagcctcc ccttctaaga ccctgctaaa cctctgggca ctgctgttaa   18360
acatttctct atgagccagg aactgtgctg agcactccac aaatattatt ttgtttaact   18420
cttccaggta gggatctaac ctggtataca ggtaaggaag tggaagctca gagagggcaa   18480
ggcacttgcc tagggccaca cagctaagtg gtggagatgg ctctaacttt tttttataac   18540
cttttccaca tgctccagag tggtcagaac atgaaacaca gtctagccag ctcctgactg   18600
gccctagagg aaaaaaactg tatgtatttt tctttttaa aaggtttaga ggctgggcat   18660
ggtggttcac gcctgtaatc ccagtacttt tgggagctga ggtgggcaga tcacttgagc   18720
ccaggagttt gagaccagcc tgagcaacgc agtgagaccc tgtctctgca gaaaatagaa   18780
aaatcagcta ggcgtggtgg tgtgcaccca cagtcccagc tacttgggag gctgaggcag   18840
gaggatcacc tgaacccagt gaggctgagg ctgagtgagc catgatcgtg ccactttact   18900
ccagcctgga caacagagtg agaccctgtc tcaaaaaaca gttttagggg ccgggcgcgg   18960
tggctcatgc ctgtaatccc agcactttgg gaggtggggg tggcagatc atgaggtcag   19020 gagatggaga ccatcctggc taactcggag aaaccctgtc tcgactaaac atacaaaaaa   19080
ttagctgggc gtggtggcgg gcgcctgtag tcccagccac tcgggaggct gaggcaggag   19140
```

```
aatggcgtga accttggagg cggagtttgc agtgagccga gatcgtgcca ctgcactcta    19200
gcctgggcga cagagcgaga ctctgtctca aaaaaaaaaa aaccaaaaac aacagtttta    19260
ggccaggcgc ggtggttcat gcctgtaatc ctagtacttt aggaggccta gacagatgga    19320
ttacctgagg tcaggagttc gagaccgacc tgagcaacat ggtgaaatcc tgtctctact    19380
aaaaacacaa aaattagctg ggcattgtgg caggcacctg taatcccagc tacttgggag    19440
gctgaggcag gcgaatcact tgaacccggg aggcggaggc tatagtgagc cgagatcgcg    19500
ccattgcact gtagcctggg cgacagagtg aggctccgtc tcaaaaacaa aacaaaacaa    19560
aaaccatctt agagttaatt cccaccggga ttcaatacac acacacacac acacacacac    19620
acgcacgcac gcacgcacgc ccgcatacac acactgcatc cacctggaaa gtgacaaagg    19680
gcaccctggg gggaattcaa atggtggtgg ccctggtttg gtgttgctgc cttagcttaa    19740
ggtcacacca gccttcagcc tcctgcccca cagtctaggg ctgctcccttc atctgatgt    19800
ccacagggac ctgttcattc ttgactcaat ccaggaagat gagaagggag agaagtcact    19860
cgcagcctga gtgaactccc ttgctccacc cctgactgct tggatccccc tagggtgac    19920
ccctgctgaa actggctcct tcctgaccgg ttcccgtcag ggctgtgctg atgggtggtg    19980
cccaggcctg cccctgggga cggggtactc tcccttggca acactccagc ttgtgccact    20040
tgacttggga ctgatttggt tctgttttga gtcccttcag gggaggggcc tatcttattc    20100
aacgttgttg tttgttttcc tcacatactg ataacttagc aaatggctat tggaacaaaa    20160
atgaaaataa atgaaccct gaagtgggat gttttaaatt tttatttatt atttttttag    20220
agacagggtc ttgctctgtt gcccagtctg gagtgcagtg gtacaatcat agctcactgc    20280
agcctctgcc tcctgggctc aagtgatcct cccacctcag cctcctgagt taaattttt    20340
tacagacgcc tgctaccatg cccggctaat ttttgtgttt ttagtagaga cggggtttca    20400
ccaggtgggt caggttggtc tcgaactcct gacctcaagt gatccacccg cctaggcctc    20460
ccaaagtact gggattacag gcgtgagcca ctgtgcccgg cctaaaactg tgtttgagac    20520
agggtctcac tctgttgtcc aggctggagt gaagtggcat gttcatggct cactcagcct    20580
cagcctcact gggttcaggt gatcctcctg cctcagcctc ctaagtagct gggactatgg    20640
gtgcacacca ccacgcctag ctgattttc tgtcttctgc agagacagga cctcactgtg    20700
ttgctcaggc tggtctcaaa ctcctgggct caagtgatct gcccacctcg gctccgaaaa    20760
gtactggaat tacagcctcc tgagtagctg agaccacagg cacacaccac cacgcctagc    20820
ttttttttt tttttttgc ttttttgtaga gatggagtct cactatgttg cccaggctgg    20880
tctcaaactc caggccttaa gcaatcctcc cacctcagcc tcccaaagtg ctaagattac    20940
aggtgtgagc caccattcct ggccttaaaa gtgtgatatt tttaatgtat tttgaaatct    21000
gcaggactct ccctagaaga taatagcaat aaccaactcc tttattgtgc ttgacgtata    21060
tcaactcact ttgcccttac cgtggctcca gaggcattgg gtccaccta taaatggagg    21120
caccaaggca cagagtgatt aaataagttg cccaggatca cacagccaga agtgtctga    21180
gtcaagattc cagcccaggc agcctagacc tgagagcacg ctcctaacca ctgcacatca    21240
ctgtcttagc acctcctcag cacaaactgg cccttgagga atgaaatacc gccgccggca    21300
cacacgctcc tgagttaagc ctttgtcaat gaaatgaaca cccacttaaa aggaataacc    21360
tgtccaggca cgatggaaca ttgaataacc ccttattcta aattcctggt ccctgtaaga    21420
ctccttcccc atgcccttgc ccttttatga ccttccccta aagtccttga ggcttaagcg    21480
```

```
ggcatagtct gcagcaaaca ctggggaagc tgagtccaga cttcagagca caggctttgg   21540
atctaggcca gctggatttg aacctcacat ttgtgatcag ctggcatgac tgtttccaaa   21600
aagtccattt taatcctcta cgtgaccctc tgtaaaatgg ggatactgaa cggtgagcta   21660
gcacgatttt acagagagtg aattttttt tttttttttt tttgtgagac agagtcttac    21720
tctgtcgccc aggctggagt gcagtggtgc aatctcggct gactgcaacc tctgcctccc   21780
gggttcaagc gactgccatg cctcagcctc gagagtggct gggattacaa gcatgcacca   21840
ccatgcccgg gtaattttg tatttttagt tgagacagag tttcaccatg ttggccaggc    21900
cactcttgaa cccctggcct caagtgatcc acctgccttg gcctcccaaa gtgctgggag   21960
tacaggcatg agccactgcg cccagcctta tagggttaaa atttaaaaga ggtgatgctg   22020
ttacaagcct gttttacaaa atgctcttat aataaatcat tatcatcact gttgctgtgg   22080
ttgtagcatc atcatcatta actcccagag ggaggaggga gtctcagagc aagctgctca   22140
ggggagactg gatgtccatg gattgtccag ctcagtacca cttcctccag gaagtcctcc   22200
ctgataagtc cagtcagcat caccctctcc ttccaatgaa ccccactagc cttgtgatat   22260
cacagatatt cttagttgac aggctcatgg tgtatgtagc ctgtctagat cataagtaca   22320
tttttttttt ttttggatca taagaacctt caagaccaaa ataatttct cctcctgagc    22380 atgctcattg gtcaagggaa ggaaggaatc gtaatagtgt taataaggct agtgtctttt   22440
caggagttgg ttctttgtgc cagtcttggt gctagacaca ccgataggaa gaatactcct   22500
tcacatcccc aggacaccaa catgggatac gtttgatcat cattcttaat ttgcagaagg   22560
agaaataggc tcagtgagat gaaatagcca ctccagtggc aaggctggga ctggaagccg   22620
ggcttgtcct gattccaaat ccagtttctt tccactgcca cggagaggga gagaagggac   22680
agtggcccca gatgaggatg gggtgactgg atgtgggcag gcctgcgggg gaagagtgcc   22740
ctctgttgag catccgaatg atggcagcag aaaagaagac tgggcagaat cccagttatc   22800
agatcccctg agggaacagt caccccgatc accctcagtc agatgagtgt gtgtagatca   22860
atgcctcata gatgaaggca ctgaggcaca gagtggttaa gtcatctgcc agaccacatg   22920
gctcagggtg cagaggccac cttaacggga gaagagatgg tcactccact ctgcagcatc   22980
agcgcccagg tgggtagaaa tcttgtcttc tatttccaca gaaagtaagg tgcccaacag   23040
tgtttgttga atgaatgaat gaatgaatga atgagtgaga ggcatccttc cttctcagtc   23100
atcctggctc tccttctcac ccccagtatt cggctggcca ccatgagtgc tatgtcggtg   23160
ctgatctcag cgggtgctgt cttggggaag gtcaacttgg cgcagttggt ggtgatggtg   23220
ctggtggagg tgacagcttt aggcaccctg aggatggtca tcagtaatat cttcaacgtg   23280
agtcatggtg ctgggaggag ggacctggga gaaaagggcc aaaagctcca tttggtgggg   23340
cttccggggt tttgaaaaat aaagacaacc tgtaatccca gctacttggg aggttgagga   23400
gggaagatca cttgaggcca ggagtttgag acccgcctgg gcatcatagc aagatcctca   23460
tctctaaaaa gtaattttt ctaaattatc cagttgtggt ggcatgcacc tgtagtgtca    23520
gttactcagg aggctgaggt gtgagttgga aggattgctt gagcccagga gttagagatg   23580
aacctgggca atatagcaag acctcatctc taaataaata ggtaggtgga tagatagata   23640
gatagataga tagatagata gatagacaga cagacagaca gacagacaga cagacaggct   23700
gggtacagtg gctcacacct gtaatcccag cactttggga ggccaaggag ggcagatcac   23760
ctgaggtcag gagttcaaga ccagcctggt caacatgggg gaacctcatc tctactaaaa   23820
atacaaaatt tagctgcgca tggtggcagg tgcctgtaat cccagctact caggaggctg   23880
```

```
aggcaagaga atcgcttgaa cccggagggt ggaggttgca gtgaactgag atcgcgccat   23940
tgcactgcag cctgggggac aagagcaaga cttcatctcc aataaaaaaa aaagaaaaaa   24000
gaaaagaaaa gattgataga tagatagata cccaaatgag gttacaaaag tgtggtctgt   24060
gcaaatgttt aaacacaaca aaccagtgcc tttaactact acagtataat cctgtaggat   24120
tgtgctattc atgatgtaat tatggttgta taaaagtaat taattctcag agcctcacca   24180
gcagtgggtc cagcaagttt gtacagccag catcttcttt cagtcagtgc gtgtcagtaa   24240
ctgcacatgt cctctcattg ggagagcctg tcgaaagtct aagtttgaag gcagctgtga   24300
aggtaaggcc aatccaaatg gctctcccag ctcctctgct gtaaccctga ccctgagtga   24360
ggacatagcc aaccttccca tctcataggt gagaaggctg atgcctggag aggggaaggg   24420
actgcccaag atcacatagc aagatagtgg cagaacccaa gcgagaaccc acagttccag   24480
cctggcttag aagaaagtgc actggacttg gagtcaaagg ctggggtgtg catcccagct   24540
ctgccataaa tccctgtgtg actctgggca atttaacctc ttagagcttt agtttcttcg   24600
tctgtaatat gagggtagca gtactaccac atagggtttt gagggagtaa ttgaattaat   24660
cacatgaaat gatgcacgtt tacaaaaaaa agcatgaagc ccctttactg tgcctcagta   24720
tcccaaagga ctttggattt actctgagaa atacagggag aactagggag tgttgggcag   24780
aggagagcta tgatctgact tatgttttaa gatactctgg cttctgggtt cagaaaagac   24840
tgaaggggca agagaggaag caggtggaga ccagagcagc agtgatggcc atcatccaga   24900
ctcagactag gacaatagct gtgagggtgg tgggaagtga ttggatcctg actatatttt   24960
aatagcagaa ttgacaggat ttgctgatag actgcacgtg gggtgggaga gggtcaagat   25020
gacttcaagg ttctcatctg gcacaactca gcagctgctg gtgccattta ctgagatggg   25080
gaacattggg gtgggataga tctgggaggg aaaacccaga gttcagtgtc gaatgtggta   25140
gcgttagggt taaggttggg gcgggtagag atgtgtatga acatcccag tggagacact   25200 gaatggagat gtacaagtct gaagcttagt ggaaaggtta gggctaggga tataaatttg   25260
ggagttgtta caatacagat ggtgtttaaa gccatgagac ccaaggagat cactcaggag   25320
tgaggataaa gagagatggg aagaagtctg aggactgagt cctagaacac cctgcatttt   25380 agaggggga catgtgtaag agccagcaaa ggagacagaa ttgtgcttgg agaggcagga   25440
ggaagcccag gagagcgtga ggtcctgaaa ggcaaggaaa gagagggccc caggtgggct   25500
gaatgctgct gagaggtcaa gtcggatgag ggctgggaag tagccattgg atttgacaag   25560
gagaccttgg catgcatggt tgtagaggag gatgaaggca aaagcctggc ttgactgatt   25620
caagagcagg agatgagaaa gtggagacag catgcagggg cagccctgcc aaggactttg   25680
ctctaaaggg gaacagagaa atggaggaga agcaggaggg caataatccg atagagagga   25740
aaaatctgat gatacagaag agagatgaac tgcaagagtc aagcctttga gttggaaagc   25800
aggagtggga ttttgagcac tgatacccttt aggccgatgc agggacagtt catctttttt   25860
aaaattatta ttattataca acattttatt taaaaattta ttttcacaga atacattttc   25920
acattagaga ttcccattgt gcgaaaataa caatttatta cttatagttt tatatttgtg   25980
gacagattgt tttagaacaa gtagaataca tttgagaatt aaatctcagt ttacaatggg   26040
taatattttg atacgtctat ggggaaactt gcccttaaat ggaacttctg tatcttcaga   26100
agcactccaa gcgtttcttc ctaggattta gaaatttata atatgagata tcagcatttc   26160
ctaattttaa aatttcccta gtatatgtaa ccatcggtag gtggtatcta ccgactagag   26220
```

| | |
|---|---|
| agggaagttt ttgaaaatta aacactgtct aattttctgc aaagtttta ttcatgaatt | 26280 |
| aagagtattt cccttagtcc attattccca aggcaaatat ggaagtttga tcatatgcta | 26340 |
| atcatactaa agctggattc tctttaagag attgagaaat taaaaggcaa aagctgatat | 26400 |
| atcatgttta gttatactgt gagtcttata agaagctggg aggcaacccc attaactcac | 26460 |
| cagaatacag aactcagtct cacaacttaa atataattcc tctcaaacct tttcctcaaa | 26520 |
| gttaaattct gaaataatc ttgtgattaa gagaagaagg ctgtccacca atggacttat | 26580 |
| ctgttatttc ttccttattg tgagcttaat ggcatgacaa agcagaggca aagaggcata | 26640 |
| catcaattct tcaaagtagg aagtcaaaaa ggtcagagct tccacagcat ggcaacagct | 26700 |
| ttgcagatgc ccacatcgtg atagttgaaa tagcaaagcc cagcaaaggt taaagctgaa | 26760 |
| aatgccaaaa gccctgcctt ggcagctttc tgcgaggcat ccccatgaac atagtcagta | 26820 |
| acaacttgtc caaggcccca gtgaccatga agagtgaggg ctgcagccag ggaatagtcc | 26880 |
| gtcgcagagc aaggattcaa ataagcagcc ggaagcagac ccgggagcaa aacactgaca | 26940 |
| accctctcgc tagtccagtg agagatgca gccttggagc cagaatggtg gctcggtgac | 27000 |
| aagtgtatgt gctgcactcc acaccattct gggataggtc ggtcctgaag aaatgctgag | 27060 |
| atatgagcag gtctgaccac tggagttcgc agcaacagag ctcggcctcc ttgggcaccg | 27120 |
| caaacggcac tcagcctcca gagaaccgcc atctcgttcc tgaggcggag agttcatctt | 27180 |
| aacgagagaa atggcaggga ctgtgaatag gccggcagat ttggtggcgg gtgccacagg | 27240 |
| ttcagtctcc tgcagggaga ggagaaaatg ccttactaat tccttgtatt ttctcagaga | 27300 |
| aacaagaggc accgtcatca gcctcatgtg agggtgggaa ggagggatgg ggtttgcgga | 27360 |
| gagggaaagt gtggtatggt catctgtggg agtggaagag agtgagaggg ctgcaggggt | 27420 |
| gcagcgggac tgcaggctgg caccagggtc cctagggctt gtagttggtg gaaagtgcat | 27480 |
| cagtgaccag ggctgtgtgc agctgctcca ggcaggtgtg gaagaagcag agttgaactt | 27540 |
| gcccagcctg gagtgctgcc cagagtgagc ccaaagccca agggagacca gagatggggc | 27600 |
| tgtttgcaaa ggaggaagta taacagtagc ccacaaaatc tgagctggtt aagaaaggag | 27660 |
| agagagtgaa aatggggagc ccagcctggc agcctgggta cacatctcag ctcaacccac | 27720 |
| actagctgaa tccatttggg ccccttcgtt gacctctctg tgcctcagtt tccctatcta | 27780 |
| tagaatgggg ataagaataa ggctacttcc tagggctgtt gtgaggattg aacaagtgac | 27840 |
| cgaacacttg ttcaattttg aatactgttc taaagcattt aggacagtgc ctggcatggg | 27900 |
| gtaagtgttg cggcagtgct gttattttca tcatcaccat tgttctcagg ctgcgttgat | 27960 |
| tggagctgct gaagggaggc aatttaagga agtgagccgg acagatagga ggtggtggtg | 28020 |
| gttatcaggt gcgatgcttg aaactgaggc ttcggaggca acagttactg gtaatgacaa | 28080 |
| ggtctaaggc ttgacagtgg gtggcagaag tgtaacgcag ggaaagagac gagcggtcaa | 28140 |
| ggagccgaga gggaaggagt tgggtggact aagatcattt gtggaagaat gatggagaga | 28200 |
| aaggctgaag gcaggaact gacatcatca gtgaccaagg ggcggccagg aggctgagac | 28260 |
| cgcagcaaga aagggagagt gtgatggcat cttcttcaag ggagctgggg atgtttgggg | 28320 |
| tggaaaaaag aacaatggtc tgggaggaa tatgggaagt tttttttttt tttttcagat | 28380 |
| ggagtttcgc tgttgtcacc caggctggat ggcaatgttg caatctcggc tcactgcaac | 28440 |
| ctctgccttc caggttcaag tgattctcct gtctcagctt cccgagtagc tgagattaca | 28500 |
| ggcacacacc accacgcctg gcttactttt gtatttttag tagagacgga gtttgccat | 28560 |
| gttggccagg ctggtctcaa actcctgacc tcaggtgatc cacccgcctt ggcctcccaa | 28620 |

```
agtgctggga ttagaggtgt gagccaccgc gcccagcctg gaagtttgta tttattaatt   28680
tttggttgtc ttcatctgtg tatgtgactt taacccctaa atacttcagt gtacatttct   28740
tttttttttt tttttttttt tgagacagag tcttgctcca tcacccaggc tggagtgcag   28800
tggtgtgatc tcggctcact gcaacctccg cctcctggat tcaagcaatt cttgtgcctc   28860
accctcccga gtagctggga ttaggggcat gccaccatgc ccagttaatt tttgtatttt   28920
tagtagagat ggagtttcac catattggcc aggctggtct tgagctcctg gcctcagttg   28980
atccacctgt ctcagcctcc caaattgctg agattacagg cgtgggccac cataaccggc   29040
ctcagtgtat atttctgatg cagttgggtt ctgtatcccc ctccaatctc atctcgaatt   29100
gtaatctcca cgtgttgagg gcaggacctt gtgggaggtg atgggatcac aggggtggtt   29160
tcccccatgc tgttcttgtg acagtgagtg ggttttcagg agagctgatg gtttgaaagt   29220
gtggcacttc ctctctctct ttctctctct ctctcacctg ccaccacgta agatgtgcct   29280
tgcttccctt tcaccttcca ccatgattgt aagtttcctg aggcctctcc ggccatgcca   29340
aactgtgagt caattcagcc tcttttgttt ataaattacg cagtctcagg aagtatcttt   29400
atagcagtgt gaaaacagac taacacaatt tcctaaaaca aggggacatt ctcttacata   29460
accattgttc agttaacaaa aatgagaaat tgacattgat atattatgat taccttattc   29520
tcatttcacc aatttttca ataatatcct ttctagaaaa aaatacatat ttttgtggt   29580 cgaggattac atcttgcatt tagttctcat gtcttattaa attccatcaa tctggaacag   29640
tttcttcatc tttctttatc tttcatgacc ttgacatgtt ttgaagtttc gagccagttc   29700
ttttgtagaa tgtgggtttg tctgctgttc ctcatgatta gattgtgggt atgcattttt   29760
ggtaggaatt ctccaagagc cgtgtgtgcc cttcttagta tatcatatca gaagacatgc   29820
tatcaatttg ccccattact gggtgtgtta actgtgatca ttgggttaag atggtacctg   29880
ccaggatctt ccactgcaaa gttactattt tcccctttgt aattaataaa catcttgtga   29940
ggagataatt tcctatagaa atcctgttga tcatccaact ttcacccact gattttagtg   30000
ttcattgatt cttccctgaa taaattagta ctataataat tgccaatggt ggttttctaa   30060
ttccatcttt ccttcaatag ttggcattct cctgtaagga aaagctttcg cttctctgtt   30120
catccactca tctatgtatt tgtttatatt accatggact cctggattcc ggtttacaca   30180
cttccatttt ctgcctttc tctctgctta atataaggat taatgagaac tccctgattc   30240
ccaggaagaa aatgtcacca gagctttctt aggtggaatg aagagaattc agtgtaagaa   30300
ccataaaggt gtatctgtgt agtatggaca gttttaaaaa acaaacaaac aaaaagaacc   30360
tccaagggca ggaagtgctg ccagactcag gagggcacta gaactgacta tgagaagcca   30420
ctgagatccc aggtagtctg tgctctccat cttttggctc tgattctctc tgtacatcta   30480
acatctctgt acaccagctt tctctttagc gaaaaacgtg tccctccac ccacccatcc   30540 acctccactt gttcctgcat ttctatgtcc cagatcctgc agaaaacaac tcttttctct   30600
cagttagtct caattctgta gtccagggag agagaatctg atcagtcccc tgggtcattt   30660
ttccactctg gtccaagcag ctacagctgg catgggaaat agttcacaca gtaaaaacat   30720
ggctgtcaag aagaggagta aatttcagag gcagaacact ccctgtgagc ccgaacctct   30780
tcctgctttg ttgcagtctt cataacgatt gctttaaaag actgcattga tataacatca   30840
tctctcttct ctgcatcttt gacttgctag cttaactggt ctagaggagg cttagcact   30900 gattttcagt attcattttc ctcaaaactt caattcagcc tgggtttctt cagcaggagg   30960
```

```
gctcggggga accagagcca gggaccagag tcatttcagt gcaccagctc aagaaatgaa   31020
tattccaggc caagaatccc caagtgttct ttctgaagtc cttcctggtg gagctcaaag   31080
agatgaaaaa cgcaagcccg cttttcagtt cttatcagga aactgcatag actttcctct   31140
ttatgtatga ctgagggctt tttaccatca tttgttcact tcacagatat ttatttggta   31200
tttactatat accaggcact cttgtggcag tggaaaatac aactctcgtg aacatctgt    31260 tccagaagga aagactgcca ataagcaata aataggcaa aagatatagc atgttagaga    31320
gtggtaagta ccacagagaa aaataaaatg gagaaaagaa acacgaaaag ttggggagag   31380
aggacaactg tttgaggggg tggccagggg cagcttcatc tcatcaaggg ggtgattttt   31440
tttgagtaca gacctgaagg taacgagtgc acaagccaca tgggtacctg agaacagcgg   31500
cagaacaatg gcagggtgct gggagggcta tttaccaccc atgctgttta gaattgtcag   31560
cacatggtga taaaaaaaaa aataggctgg gtgcggtggc tcatgcctgt aatcccagcg   31620
ctttgggagg ccaaggcgga tggatcactt gaggtcagga gttcgagacc aggctgggga   31680
acatggtgaa accccgtctc tactaaaaat acaaaaatta gccgggcaca gtggtgggcg   31740
cctgtaatcc cagctacatg ggaggctgaa gcaggagaat cgcttgaacc cagtgggtga   31800
agtttgcagt gagccaagat ggcaccactg cactccagcc tggcgacaga gcgagactcc   31860
gtctcaaaaa taaataaata aataaataaa aataaaaagc agacagactt tttagttggc   31920
tttagaattg ttagacaccc tctgcagaca aggcaccccg attgcttgca cccagggtgg   31980
actactccct ccatcctgcc cttgttacac cctggctggg ggtcagcatt tcaggcagct   32040
gaatgaccca aagtgggaac acgctagtgg gtttgaggat gagcaagtgg aggagtgcaa   32100
taggaggtga cgcccgagag gtcaggtgag agtggatcct gcagggtcgt ggcaagaacc   32160
tggaccttga ctttgagtga catgggagcc gctggaggct tctgagcaga ggagtaacat   32220
gatctgactt gcattttatt ttatttattt atttgacgca gtctcactct gtcgccgaag   32280
ctggagtgca gtggcgccat ctcagctcac tacagcctct gcctcccagg ttccagtgaa   32340
tctcctgcct cagcctccca ggtagatggg attacaagca agcatcacca cgcctggcta   32400
atttttgtat tttagtaga cagggtttt tgccatgttg gccaggctgg tatcgaactc     32460
ctgacctcag gtgatccacc cacctcagcc tcccaaagtg ctgagattac aggcttgagc   32520
caccacgccc ggcctgactt gcattttaac agggtcactc tgtctgctgt gtggagaaca   32580
gtccgcagga agacaagggt ggaaatgggg agaccagtta ggaggttact gtaacaattt   32640
ggggtagcgg tgatggtggc ttaaaccaag atggggtcag tgggaaatgg tgctaaaaat   32700
cctgccaatt ctgggtattt ttagaaagca cagctgacag cttttctccag tagcccacta   32760 aataagttat gaagcattac taaaatgtga tagtcatgat gcaaaattag aatatatcta   32820
gaatctcccg aagaccttag tttggtatta caagaagtct ggttgcttca tgttgcaaaa   32880
tttatatcac tcatcactcc tgcagagtta aaattccgct gagaagtagg aatcagtgaa   32940
gtgcgtgtcc atgtgggttt ttgccacacc taagtgaacc ttggtcaaaa gcatataaga   33000
gctactgata ggccgggcgt ggtggctcat gcctgtaatc tcagcacttt gggagggaag   33060
gatctcttga gcccaggagt tcgagaccag cctgagcaac atagtgagat tccatcttta   33120
cacaaaattt aaaaattggc caggcatggt tgtgcactcc tgtaatccca gctacttagg   33180
aggctgaggt gggaggattg cttgagcctg ggagttggag actacagtga gctgtggcca   33240
caccactgca ctccagcttg agcaatggag caagactctg tctcaaaaaa aaaaaaaaa    33300 aaaaaaaaaa gaggccgggc acagtggctc atgcctgtaa tcccagcact tgggaggcc    33360
```

```
gaggcgggtg gatcgcctga ggtcaggagt ttgagaccag cctggcaaac acggtgaaac   33420
cccatctcta ctaaaaatac aaaattagcc cagcgtagtg gcgcatgcct gtaatcccag   33480
ctactaggga agctgaggca ggagaatcgc gtgaacctgg gaggcaaatg ttccagtgag   33540
ccgagatcgt gccattgcac tccagcctgg gcaaagcctg ctgggttggg ctgggtaagc   33600
tctgaacacc agtctcgtgg cttcaagtca cacctcctaa gtgaagctct gaactttctc   33660
caaggaccat cagggctttc ccctgggcag aggatgccga cactcactgc tcttactggg   33720
ttttattgca gacagactac cacatgaacc tgaggcactt ctacgtgttc gcagcctatt   33780
ttgggctgac tgtggcctgg tgcctgccaa agcctctacc caagggaacg gaggataatg   33840
atcagagagc aacgataccc agtttgtctg ccatgctggg taaggacaag gtggggtgag   33900
tggtctcata cttgggctga gcagaatggc tcagaaaagg ctctggctga aaaaatctcc   33960
ctcctttacc aacttcccct gggtgtctga agcccttcca tcatgattca cttctttgag   34020
tagtgtttgc taaattcata cctttgaatt aagcacttcc ttttagggac ctctcttcat   34080
taatatccac tagaaaggag agactcatta tgtgtgagtt tcaataagtt tatccaatcc   34140
ctttgttttc aactgaaagg agggaaacgg acaagtgaag aaggtagggc ccaggagtga   34200
aggaacaagg gtgggaatag taataatgtt gtactttgaa aatctactgg gaaaatgatg   34260
aacttagact gctgggagag gctaatagaa aatcgggcag tgagcttgat agtaggcaaa   34320
ggactatcag gccacggggt caagttaaag cagcacattc attaaaaaaa aaaaaataag   34380
cgtttgggcc aggcgtggtg gctcaagcct gtaatcccag cactttggga ggccaaggtg   34440
ggtggatcac ctgaggtcag gagttcgaga ccagcctggc caacagggcg aaaccccatc   34500
tctactaaaa atacaaacaa atcagctggg catggtggtg cacgcctgta atcccagcta   34560
cttgggaggc tgaggcagga gaatcttttg aatccaggtg gtggaggttg cagtgagcca   34620
agatcgcgcc actgcactcc agcctgggca acagagcaag agtccatctc aattaaaaag   34680
aaaaaaaaat taaaataagc atttgaccat cacagagcag gttcaggagg cctggggtat   34740
gcagatttca accctcttgg cctttgtttc cttgtctgta aaatgtggtt agctggtatc   34800
agcttgagag ctcggagggg agacgtgact tccccatcta actctaagtg acaaggctga   34860
gactctccag ccctaggatt ctcatccaaa acccctcgag gctcagacct ttggagcagg   34920
agtgtgattc tggccaacca ccctctctgg cccccaggcg ccctcttctt gtggatgttc   34980
tggccaagtg tcaactctgc tctgctgaga agtccaatcc aaaggaagaa tgccatgttc   35040
aacacctact atgctctagc agtcagtgtg gtgcagcca tctcagggtc atccttggct   35100
cacccccaaa ggaagatcag catggtgagc agggcgctgc ccttgggcag cacttgggtc   35160
taacaggact agcacacata tttatgcccc tccccacccc agggccagcg tgggttggga   35220
gagggcatgc cgggtggtgg agctgtgcct gcctctacag tggagctcta ggaagaatgc   35280
tgggtggtca caggggcct gggactcagg agactgtcca gtgatcaaag gctttctggg   35340
gggagtgatt aaatccatcc atgctaacat gaaacagacc tgagtttgaa ccccgtttct   35400
gctagttgct caagtcagtc accatgagcg agagtcagca gcaacagact agactagaat   35460
tagccagcct ctctcttccc cccaacaaat ttcaagaatg gaaccatcag aatcagaagt   35520
agagaagtat gtgacactag ccatgtggct ctggtcaagc cacttcaacg ttttgagtct   35580
cagtggcctc atctgtaaag tgagaattaa gagatggtgc atgtaaagtg cttaacgggg   35640
agtaaatggt aggcaaacat tagctgctgc tattagtaca gagagacaat ggtgtgtgtg   35700
```

```
agtcttgtgg gcagagatgg gtgagagggg agacaaaaca agttctcatg atgatggggg   35760 caggggggtcc agctggtggt gtcggaggga agtctggaca gaccagtggt ggggctcggg   35820
tgggaggcac tgggggggct ggagtggaaa gaatgtggcc acagatgaca gcttcacagc   35880
agaattcagt gctaagagga agtgagtggc catgagttcc atggtgacag aaagtctaag   35940
acacctagca aggcaggagt gggtgtcagc tcagggaagc tcagaggcta aacctaggtg   36000
agagctgagg gtgtcagata agagcaaggc aaggctccgg ttctggagta gtgaaggaca   36060
tagcagagct ataacccagg aacaaggccc agcttattgg aactgggacc agtcacacag   36120
ggtggcacag gcaccaagta gccaataata ataataaaaa caataacaat gatttatgtc   36180
tattgggcat ttattcatgt tctatgccag acactggact aagagcttta tatgtggaaa   36240
ctcatttaat ccttacaata accttatgaa gaaggtacat ccaaaacccc attcttctag   36300
gccaggtgca gtggctcaca cctgtaatcc caatattttg gaaagctgag gcaagaggat   36360
tggttgaggc caggagttca agaccagccc aggcaacata gcaagaccct gtctctaaaa   36420
aataaaacaa aaacccattc ttcccgctgt ccagggacac accactaatg agtgtgatgg   36480
gtgcctagga tgctgagcac ctggacttcc cagctcattc cctaaatgct gcacaatcag   36540
ggtaactgtg ccctgagcct aagaggcagt agtgagctgg cccaccgtgt ccactgatga   36600
aggacacgta gccccaacac aggggagagg tggtttcagg atcagcaaag caggaggat    36660 gttacagggt tgccttgttc ccagcgtgct ggtcacttgc agcaagatgg tgttctctct   36720
ctaccttgct tcctttaccc acacgctatt tctttgcaga cttatgtgca cagtgcggtg   36780
ttggcaggag gcgtggctgt gggtacctcg tgtcacctga tcccttctcc gtggcttgcc   36840
atggtgctgg gtcttgtggc tgggctgatc tccatcgggg gagccaagtg cctgccggta   36900
agaaactaga caactaatgc tctctgcttt ggctgaaggc cagcaggacg ctgggacctg   36960
atgggccact gtgcagtgca cagctgcatt aggcaggtgt tggtgcattc tcttattggc   37020
ttcaacgcct agcgagggat ccatcctggc tcggtggcac atttgttaag atgctgggga   37080
gcaggtggca gaacccattt gagcttgctt gggcactggg gagaatttgt taccaggcta   37140
caggggtgtc acagaactca aggacaggga ctggagtgtt gtgggagcc cagaagcccc    37200 tgttttactt cttctttgc ttttcctgaa tatctgcttt attcttactc tatagacctg    37260
cttcctcctc tttcacccca cattgtgggg tgtagtcttt tgcttcaaga aagcagcctg   37320
gtggatggaa tctcttggcc ccaatcccaa attctctgga gaaggggctc tttggttaa    37380 cttgataat gttgtcttca gctgggggtg ggcacatcgt gcatatgtgg ctgctgccgg    37440
ggaaccacgt ggatgatgtg agaggagcag cacccagaag agggagtgct gggctgatgg   37500
tccaggtcgt gtccacttct gattgtttaa ttcttcttct aagtggatgg atctttctcc   37560
aatactcagc aaatcctgat cgttccagaa tacttcatta tagccaattg gttataatgt   37620
gcttctctaa gagaaatatt tagggacaac aaatcttcat gggtttgaag acttgatgga   37680
ggaaaaagga gtagattttc gaaggctgga tttggatgaa caggggctat tcagggagtg   37740
cattccaacc taaaattagg aaaaactggc tgggcgcagt ggctcacgcg ctttgggagg   37800
ccgaggcggg cagatggcct gaggtcagga gttcaagacc agcctggcca acatggtgaa   37860
accatctcta ctaaaagtac aaaaattagc caggcgtggt ggcgggcacc tgtcatctta   37920
gctactcagg aggctgagat gcgagaatca cttgaacctg ggagacagag cttgcagtga   37980
gccgaaattg cgccactgca ctccagcctg ggcgacagaa caagactctg tcttaaaaaa   38040
aaaaaagtgt tttatataca gagtggaata ttatttagcc ataaaaagaa tgaaatcctg   38100
```

```
tcatttgcag caacatggat ggaactggag gtcattaaaa aataaaataa aataaataag   38160
gaaaaacgta tcaatacttc gattgaccaa aaccagggca aatctgattt tcatctttgc   38220
aaggggaaca aatttctttt atctcctctg gctttgaaac cctgaaatga aaggaggaag   38280
ggcagaaaaa agaacacata gcaagttacc atcaggctca gcgcccatcg cattccctga   38340
gcttgtttcc ttgacttcat cactggcagg actattcaaa aatgattccc tcattcattc   38400
atatattcat tcattcatca ttccttcatt caacacatac gttttaacac tcatcttgct   38460
tttcaagcta tagtttagtg agcgaaatgg atacacagaa tacagtgtga gaacagctac   38520
agggcacatc tgagctagcc tgggatgggt ccggaaatgc ttcctggagc agaggaaacg   38580
gttgacagcc aagtgttgac agagaagtag tattagccag gcagagacat ggggaatgta   38640
ttccaggcag aaggcacagt gtgtatgaaa gcttattggt aagaagagtg tgtggcccaa   38700
ccaggaaaca gacattctga aggcataggg tccacccagg agcatggtga acccagatcc   38760
ctgaaagatg ggaggtgctc aggcacactt cctgggctag ttgaggggtc tggattttta   38820
tttacttatt ttttttattta ttgagacaga gtctcgttct gtcacccagg ctggagtgca   38880
gtggtgcaat ctcagctcac tgcaacctcc acctcctggg ttcaagtgat tctcctacct   38940
cagcctcctg agtagctggg attacaggtg cccaccacca tgcctggcta atttgtgtgt   39000
gtgtgtgtgt gtgtgtgtgt gtgtgtgtgt tttgttgttg ttgttgttgt tgagacggtg   39060
tctcgctctt ttgcccaggc tggagtgcag tggcgccatc ttggcttact gcaagctctg   39120
cctcccgggt tcacaccatt ctcctgcctc agcctcctga gtagctggga ctacaggcgc   39180
cctccaccac gcccagctaa ttttttgtgt ttttagtaga cgggggttt cgccatgttg   39240 gccatgctgg tcttgaactc ttgacttcag gtgatccacc cacgttggcc tcccaaagtg   39300
ctgggattac aggcatgagc caccgtgccc gacctggatt tttattctga agactaatgg   39360
ggatcctaag gaaggaacca gcctgactga atttgcatat gtgtccacat ctgctggctc   39420
atggctgtgt gggaggctga gtgatgggga ggaaggatta ctgagtaggg atctagaggt   39480
gtggcctcat gctttctttc taaccagctg tgttgtcttt gggatggtgc ttaaatttgg   39540
gctagaccag tgggtcttgg tcacccccca ggggacatct gacaatgtct ggaggcgttc   39600
ttggttgaca cagtggggtg agggctgcta ctggcagctc gtggggagag accaggaatg   39660
atgcttaaca tcctacagtg cacagggcag cccccatcac aaggaattat cagctgaaat   39720
tgtgaatagt gcctacacta gacccttgct actcatagtg tggtccgtag atgagcagca   39780
ttggcatcac ctgggacctt gttagaaatg ctcttagacc ccaccccaca tccactaaag   39840
ccagctcttc atttcaacaa actccccatt gatgtgagta cacattcaag tctgagaagg   39900
gcttctttga ggtgagcctt agtgcccatc cccatttggt ggcgccggat accaaggtg   39960 tgtgaaaggg gtgggtaggg aatatgggtc tcacctgcca atctgcttat aataacactt   40020
gtccacaggt gtgttgtaac cgagtgctgg ggattcacca catctccgtc atgcactcca   40080
tcttcagctt gctgggtctg cttggagaga tcacctacat tgtgctgctg gtgcttcata   40140
ctgtctggaa cggcaatggc atgtgggtca ctgggcttac ccccccatccc cttaacactc   40200 ccctccaact caggaagaaa tgtgtgcaga gtccttagct ggggcgtgtg cactcggggc   40260
caggtgctca gtaggcttcg gtgaatattt gttggctgat ttattcagaa attatgtcca   40320 gccccctacct tggatggatt tatcacctct ccaggccacc tcttctttcc aaataggacc   40380
acctaggtat agaccaaaga cacgaaatct tctgtgaccc cacaaacaca gagcaggtca   40440
```

```
aataggccca agccaattga gactgtggtt caggtcgtga tgcagagctt tgctgtggac    40500
gtgctcccac tgcgtactag ctgggcatgc ggcttaacct ttctcagcct cagtcgcccc    40560
cttgtaaatg gagataagga tactatctcc cctcacaggg ctgttgggat gctactggat    40620
ttaataagct aatgcaggga catgctaagc acaacccatc cctgaggccc agagaagggt    40680
gggcctcggc tgaggtctca ctgtgaggtg ggaatgtggg cctccagacc agaggtaggt    40740
cctgtggccc ctagacagtg gacagcaatg gtcagtttga cacaccagag ccctagccat    40800
tacttcctgg atgttgtgtg aatattttct ggacatggct tatataaaat gaaaaagtga    40860
attgggcacg atatagggat agattttag agatgaactg atagcatgat gataatcata    40920
ttcactgata acatttacta ctgttattga ctgctttaaa agtgttgggc attgtgctag    40980
aaaccattat atgcattatc tccttgaatt ctcacaaccg cctactgagg tattctcaga    41040
ctctaagaaa tgagatttaa gagaagttat ctgcccaagg tcacccggct ggaacctggc    41100
tgtaaaaatg gctgaagcag gtgatgagga gctgatgtgt ttggacgtgt ctcagagaaa    41160
tcatggaggc gctggggttc cttccggttc ttggatgcct tctacagaga caaccatagc    41220
cccaaattat agggatcaca tatcagtggg tgagacatcc ttgcttggga tgaggagggg    41280
atgagctgtg tgaagcaagg tgcctctgta atgggttcca gtgatgtgtc tgccactgtc    41340
ttaataactg tgcaattcta agcagaacct ttcctgtctc tgggcctgag agttcccctc    41400
tgtaagatga ggacttgacc tagcaaggtc ctactcagat gcctgtagag aacaggcagg    41460
ggaagttaga aaaaaaaaa gccagtgaag gaagggagct cttcagcttg cacccaccat    41520
cacagtgcag ggacccaggc tcagtgttgc cagatccaat gacttctcaa gagctcaaaa    41580
tctagagttt tgcatgtgct ctcccaagta ctggcagaaa attcaagatt gttagtaaca    41640
ctgtgtggct aaattctgct tgtgggctgc ctagattccc aattctgtga ttctgtggtt    41700
ctctggaagc attggttctc cacagcacct gcatcacttg gaaacttgtt agaaatgcaa    41760
gccctaccta cggcccccacc ccagacctac ccagttagaa atctgggggt gggacctatc    41820
agtccatgtt tgaacaagcc ccacaagtgt tctcttgcaa gctcaagttt tagaaccact    41880
gacctatagc caaaaaagaa aaagccaatc agtggtttgc tggtagagga ttaacttaac    41940
aactggcttt ccatgaaaat aaagccttga ttggtagcac ttgcaatttc tatggtacaa    42000
acgcttccca catgactgag ttcaagctat caaggagacg tcactgcaca tggacttggg    42060
aagagatgag aacaatcagc ccactgagcc tatgggaact ggctccagca catccctgca    42120
agtcaactct catcagggtg agtgagttga ggaccaagaa gcagttatcc tcttgccttt    42180
gcaggaccca ggcaaaggga agggcatagt gacagtgatg atctctcttc cggaagtctt    42240
tggtttgctg agagtaaaag gcgtgggctt caccagtggt gaagccagtc atgcagcctt    42300
agtcctggta ctcaaactcc ctaaatctca gtttctatc tgtaaaatgg gaaaataagt    42360
cctatgtcac agggttgctg tgcagattta gcaatagaac atagcccgt tctttatgat    42420 gactgatgct gcatcagtat ggggacatct ctatgtaatg gaaagatgga gagaggatta    42480
agtgcaaagt cacagcactt aatgggaact gtggattagc tacttggtgg cattgggcaa    42540
gtcagttgac tttgcattaa ttccacaaac aatatttccc aatttcctat tcagatgagc    42600
atatgtgact gagtcagatg ctgtgatcag agccaggatg gagcatttcc cacaaactgt    42660 gggatttta agtgatggga aggcacactg aaatggcatt gaatcatgca gttgcagata    42720 ctcttttttca attctcagtc ctttgattac atcagggaga aagaaagtc cccacttggg    42780 ctgagaatct ctgcacccctt ctagctcttg ttaaccactc ttttgaatag cagagaaaac    42840
```

```
ctcagactgc catatctggg agagatttta gcaacatttt gttttcattg tatctctttt   42900
tacagctacc tcccatttcc cttctatttc aagctagtaa cacagttttc ttttaaattc   42960
atttatttaa atgtaaaaat aagtctattt ggagaaaaaa aattttttaat agcatctctg  43020
gaatgccagt atggctaaat tcatgaatgt tgtcctcaaa tgctgaaatc tgggaagcat   43080
ctggccaagc tttgtggaca ggccttccta gtttgaatcc caagagccac tcattccgag   43140
ccacaaaaca ttggaattct tggttcactt ccctaacctg aacttgtcct ctgtgaaata   43200
gggacattaa tagctcactc acagggctgc tgtgaggaca tgtgttgagc tgagggtctg   43260
gccaggggag accctgtgca gggagactgt tatcatggtg atggatttct gcttcattca   43320
tttcttttc cagacagcat catatagaat gagttgtggg gtggcagtca gcaggtttgg    43380
gtttatcctc tattctgcca cttattactt aaaaaaaaaa acccaactta tatagtataa   43440
gctatatcca gaaagtgcaa atatcatac aagtaccatt tgatgaatct tctgatatcc    43500
ccacataacc aacacccaga acctcttctt gtctcattcc aggataacca ctaacctgac   43560
ttctaacagc atcagtcagt tttgtctgtt tttgtacatt atatatgtga tggtttgaat   43620
gtgtccccca aatttcatgt gctagaaact taatccttca attcatatgt tgatgctatt   43680
tggaggaagg gccctttggga agtaattagg attagataag gtcatggggt gaggtatgat  43740
ggcactggtg acttataaga agagaaagag aaatctgagc tggcatgctc ttgccctctc   43800
accgtgtgat gacttctcca tgtcatgatg cagcaagaag gccctcacca gatggtggca   43860
ccatgctttt ggacttccca gcctctagaa ctgtgagcta aatcaattta ttttctttat   43920
aatcacccag tttgatattt tgtcatagca acagaatatg gacaagaaa gaaaattaat    43980
gcaagaagta gagttttttac tgtaacagat tcctgaaaat gtggaagtgg ctttggaact  44040
gggtgatggg aataggttgg aagagttttg aggagcaggc tagaaaaagc ctgtattgtc   44100
aagaatggag cattaggcca ggcacggtgg ctcagactta taatcccagc actttgggag   44160
gccaaagcag gtggatcacc tgaggtcagg agttcgagac cagcctggct aacatggtga   44220
aacgctgttt ctaccaaaaa tacaaaaaat tagctgggca ctctggcgca cacctgtaat   44280
cccagctact caggaggctg aagcaggaga atcacttgaa cccaggaggc agaggttgca   44340
gtgagctgag atcgtgctat tgcactccag cttgggcaac aagagcaaaa ctccaactca   44400
aaaaaaaaaa aaaagaaaa agaaaagaa tggagcatta aagacagttc tacagttctg    44460
gtgagggctt aaaagaagac cccagaacta gggaaagtct ggaacttctt aatggttact   44520
gaagtcgttg agatcagaat gctgatagaa atgtggctgg tgaaggccat tctgatgagg   44580
tctcagatgg aactgaagaa ccacgtgttg gaaactggag caaaggtcat cctttttata   44640
aagaagcaaa gatcttagct gaactttgtc tgtgccagag tcatttatgg aaagcagaaa   44700
atccgtaggt cacccatgtt gtagagaatg aaagaacatt ttcagctgag aaaactgaga   44760
gtgtgaccaa gctaccgatt gataagaaaa ctagtacaca taaattagcc aggcgtggtg   44820
gtgggcgcct gtagtcccag ctacatggga ggctgaggca ggagaatggc atgaacccgg   44880
gaggcagagc ttgcagtgag ccgagatcgc gccactgcac tccagcctgg gcgacaaagc   44940
gagactccat ctcaaaaaaa aaaaaaaaaa aaggaagaa agaaaattag tacacataga    45000
acaaagccag aggctgttca tcaggacaag ggagaaaaac tccaaagcca tttcagagat   45060
cttcaagact gccctcccca ttactggccc agagctctaa gagggcagaa tggtttggaa   45120
tgaccagctg ctgcccaggg ctgccttggg tctctgctcc ccacatttct ggtgcagcat   45180
```

```
tcctcagcca tcccagctgt ggttcaagtg gccacaggtg tgatgtggaa ggtaaaagtc    45240
ataaaccttg gcagcataca catggcacta attttgcagg tgtgcagaat gcaaaagctg    45300
agggggcatg ccttctccca cctacatttc aaagggtgct gtgaacggcc accccagaga    45360
gccccctagta gagcaaggtc tagtggagct acaagggtgg ggccaccgcc aagaccccag   45420
aatggtagag ctatcatagt gcaatgccag cttgggagaa ctgcaggcat gagactccaa    45480
cctgtgcgaa gtgcaacatg ggcagaaccc agcaaaacca caggggcaga gctcccgaa     45540
gcttcggggg tccaaattcc atagtgtgtc caggaggtgg cacacagagt aaaagatcat    45600
tctgaaggtt taaggtttaa tgttgttttc tatgttgggt tttgtacttt cctggaacca    45660
gttaccctt ttcccttgcc tcttttttcct tttagaatgg gaatgtctgt cctatgcctg    45720
ttccactgtt gtattttgga agtcaataac ttgttttgac tttacaggct tacagccaga    45780
gggaatctcc catagaatga attgtacctt aagtctcacc cacatctgat ttagatgaga    45840
ccatggactt tggaattttg agttggtgct ggaacaagtt aagactttgg gggttgtcta    45900
agtgtggtgt ttcatgcctg taatcccagt gatttgggag gctgaggtgg gaggattgct    45960
tgagcccagg agttcaagac cagcctaggc aacatagtga gacctgtctc tacaaaaata    46020
aaaataaaaa gttagccagg tattgtggca tgtgcctgta attctagcta ctcaggaggc    46080
tgaggtgaga ggatcacttg agcccaggag tttgaggctg cagtgagcta tggtcgtgcc    46140
actgcattcc agccagggca acagagtgag actctgtctc tacaaataag attaaataaa    46200
cgtagctgga gatggtggca cacgtctgta gtcctagcta ctcaggaggc tgagacagga    46260
ggattacttg agccaaggag tttgaggctg cagtgagcta tgatcatgcc actgcattcc    46320
agcctggatg atagagcaaa atcccatctt taaaaaaaa aaaaaaaaa aaaaaatat       46380
atatatatat atatatatat atatatatat atatatatat actttggtgc tattgggatg    46440
aattttgcat gtacgaagga catgcatttt gggggctggg gcagaatgct atggtttgaa    46500
tgcatccctc aaatttcatg tgttggagac ttaatctcca aattcatatg ttgatgaaat    46560
tggaggtgaa gcctttggga ggtaactagg attagataaa gtcatcaggg tggggcccct    46620
atgatgagac tggtggctta caagaggaag agagacctga gctgacatgc tcttgccctc    46680
ttgccatgtg ataccctctg ccatgttatg gcacagcaag aaggtcctca acagatgcca    46740
gcagcatgct cttagacttc ccagcctcca gaaccatgag ctatatataa ttattttata    46800
aattacccat tctgtggtat tctgttatag caacagaaag tgaactgaga taatatacat    46860
ggaatcatac agtaagtctg tgcttttgta tgcttctttt actcaacatt gtagttgtga    46920
gattcatcca ggttgttaag cattgctgta ctttttttcc actgggatat agtgttctgt    46980
catgcttggg tcttaattta taaggtgac tgagtggcat tttcttccag tattattgga    47040
aggaaagttt tgttgttcac agttcccctg taaaaaagag gcagaacacg tcttgcaggg    47100
ccacacaaaa ctgtgtcatc cagggaccag gcagcagaaa gagaggggga actgggccta    47160
tgcctttatg aaaagagtg gtgggagagt aactgggtga gggcatccac taatgggcag     47220
gaagtgaaaa cacatatgtt ggaatttgta gctgaggggt ttataatatg agtttcccat    47280
gcctgagaaa gctgacttgc aagaaaacga gataaacaac tttggccatt agtgtggccc    47340
tgtcataaat gaatgccgga tagacaaatc gagaatctaa gaaaagatag ttggaacaag    47400
tgttccattg tgtgaatgca gcagaattta tttatccatt attgaggagg atttgggtag    47460
tttccagttt ggagctatta tgaatattct agtattgctc ctctgaacat tctagcactt    47520
ttgttttttgg agcacacgaa tgcacttctg ttgattatat gcctagaagt gaaattgttg    47580
```

```
agttatacag tattcacaca gtcagcctta gtggctactg ctaaacagtt ttctctagta   47640
gtttgcgcca atctaatcac cagtagtgta tagaagctcc ttttactcca cattttgtta   47700
acacttggtg ttttccttct ttttgattag tcatttagca gtgaaaccta ttttttacat   47760
tttgatatct ccaataacta actaaatgga gcacttttaa tatgctttt ggacagttga    47820 atatcttttc ttgtgaaatg tctattcaag ttagtttgcc cattttctat tgtggtgttc   47880
tgtctttttc ttattgattt taggaattcc ttacatatcc tggatatgaa tcccactatg   47940
tggcttacct ttttccttct ttcttttga aacagagtct ccttctgtca cccaggctgg    48000
aatgcagtgg cgctatctca gctcactaca acctctgcct cccaggttca agcaattctc   48060
atacttcagc ctcctgagta gcttagatta caggtgcatg ccaccatgcc caccgaattt   48120
ttgtatagac aaaataattt ttggtagaga cagggttttg ccatgttggc caggctgatc   48180
ttgaatccta gcctcaactt tggcccacct tggcctccca aagtgccagg attacaggtg   48240
tgagccacca tgcccagccc accttttact ttcttaatgg tgtcttttga acaaggaggt   48300
tcttaatttt aatatagccc aatttatcat tgttcccttt atgcttagtt cttttatgtc   48360
ctgtttaaga atttttgcag ccagctcggt ggctcacacc tgtaatccca gcactttggg   48420
aggctgaggc tggcagatca caaggtcaag agatcgagat catcctggcc aacatggtga   48480
aaccctgtcc ttactaaaaa tacaaaaaat tagctgggcg ttgtggctct tgcctgtagt   48540
ctcagctact cgggaggctg agatcacgcc actgcactcc agcctggtga cacagcaaga   48600
ctccatctaa aaaaaaaaga aatttgcaag gtcatgcata tgtcccctg aattttttc    48660 taaaaatcac ttaattttag atcaatgaat tgagtaattg actccatttt tcagtcattc   48720
aacaaacatt tccctgaggt tttgataacc tgaactgtgt ttggagctgg ggaggaagca   48780
aactattgaa tatatacaaa gatggcaaag atgagggcct ggagcttgcc acacggaagg   48840
ggggatggct gcctgaatgg ttgggcaggt agttgttgac atctgcactc cctacaagag   48900
cagcagggtg gcaactcttt ttatctttt aatttatttt tctttctct ttttttttg     48960 agatggagtc ttgctctgtt gcccaggctg gagtgcagtg gcgtgatctc agctcactgc   49020
aaactccacc tcctgggttc acaccgttct cctgcctcag cctcctgagt agctgggact   49080
gcaggcacct gccaccactc ccggctaatg ttttgtattt ttagtagaga aggggtttca   49140
ctgtgttagc caggatggtc tccatctcct gacctcatga tccacccgcc tcggcctccc   49200
aaagtgcggg gattacaggt gtgagccacc acacccggcc ttaatttatt tttctagtct   49260
gcaggtaatt ctttttaatt ctctccactc tcctatgatc ttatgaggta gggactgtga   49320
ttatttctcc cactttataa tgaacaatca gtaaagacag ggaagataac caaatgacat   49380
acaaggtggg gtccaccccca tgaggctgca ggcttggagc tttcctttgt cttaaaaatg   49440
agaacatgag ctgcccacct gttgagacaa gaaataggaa aggcttaaaa aactggcttg   49500
ttgtgtacaa ctatccgtgg ggctgcagtg aacgggctgg cagtgcccag gtgcatgctg   49560
aaccctggga caatcacatt cagcatccag ggccccccgt aatagcttaa tgtttgaatt   49620
gaacccctgg ggttgccttg aaggagagag atcctggaag tatgttcaag gggtagggat   49680
gggcagggga gatgggtctg aaagccaagc tctaccccac ccaccttgcc caagagaaa    49740 tagaaccttc atctttaatt gcctaacgag aaaactgggg ctggccagat gtggtggctc   49800
atgtctgtaa tcccagcaat tgggaggcc aaggcgggca gatcacttga ggtcaggagt    49860
tcgagttcag cctggtcaac atggtgaaac cccgtctcta ttaataatac aaaaattatc   49920
```

```
caggtatggt ggcgcatgcc tgtagtccca gctacttgag gcacaagaat cgcttgaacc   49980
tgggggacag aggttgcagt gagccgacca ctgcactcca gtctggacga cagagtgaga   50040
ctccatctca caaacaaaaa cagaaaaaaa aaaaaaaaa agagagagag agaaaactgg    50100
aggctctgag aggttaaagg acttgcccag ggtcttgcag ctagtaagtg acagagctgg   50160
gacttgagct tgggttttct gactcctggt ctggttcatt atccatgagg tgctgggaac   50220
taaaataagc cacaatcttg gaatctccgt cgcctccctc cctcccacat gtctgcgtgg   50280
ctttttggga aaatgccagg ggaatgtacc agccagggag aggacccttg ttttcctcat   50340
ggcccttcct ggcaatggca ctactgacac cgacagtcct ttttgtccct gatgacctct   50400
gctgcctgat gcccaagtga ccacctctgc tttgtcattt ctaggattgg cttccaggtc   50460
ctcctcagca ttgggaact cagcttggcc atcgtgatag ctctcacgtc tggtctcctg    50520
acaggtcagt gtgaggccac ctttcttcca ccattgccag gacacagcac ccacgtccag   50580
agcgcaccct gccgtgtggc tggatgtcta tgtgccccat ctccttccct gaggatcaca   50640
taatttcaga attggaaagg ttcttagagg tcacctgctg ctaatgtgga ctgtgaggcc   50700
agggcaggga agggacatcc ctgaggttat aagtagggtg agtggcaacg ttgcagactt   50760
ttgaacccag ggctggtgat cacactcagt tttgcacaga agcccgagaa aatccttaca   50820
cccaaaagcc tacctttat ttctgaggac acccataata ctattttatt caacagatat    50880
ttattcaata tccactatga gccaggcact ggggacacag cagtgagcaa aacaaattcc   50940
ctgaccccat ggaattgacc ttctagtggg ggaaggtatt agcaataaat agacaaataa   51000
gtgtctacta cgccagatgg gaagaagtgg ctgtgaagac agagcaaact agagaaacat   51060
agagtcaatg tgggatgggg tgttcttta gggggtggt cagggaaagc ttatctgagt    51120
agttagcttt taagcagaga ccccaatgaa gaggagggag atatgcgatg catttagtta   51180
ggggaagaac attccatgaa aataggatag caagtgcaaa ggccctgaga cagcagcatg   51240
ctttgtgtgt tgaggaaca gtaaggagac cagtgtggtt ggtgtgaatg gagtgagaag    51300
gagcagcagg ggttgagggc agaatggtag tgaggagcag gcccttataa aagatgggaa   51360
gccactggaa atctttcaac aaagggaaa agtatgtttc tgttcttgca atacaataga    51420
aaagcaaaaa atctagggga gttgctaatt agccagtttt acttatatgc caggtgaaaa   51480
tatgtggcta ggtgcagtgg ctcataccctg taattgcagc agtttgggag accgaagtgg   51540
gcagatcatc tgaggtcagg attcaagacc agcctggcca acatggtgaa accctgtctc   51600
tactaaaaat taaaaaatta gccaggcgtg gtggtgggca cctgtaatcc cagctacttg   51660
ggaggctgag gcaggagaat tgcttaaacc cgggaggcag aggttgcagt gggccgagac   51720
tctgtctaaa aaaaaagaa aatacacatt caggccaggc acagtggctc acgcctgtaa    51780
tcccagcact ttgggaggct gaggcaggta gatcacctga ggtcaggagt tcgagaccag   51840
cctgaccaac atgggaaaac cctgtctctg ccagaaatac aaaaattagc caggcgtggt   51900
ggtgtgtgcc tgtagtccca gctactcggg aggctgaagt aggggaatgg cttgacccca   51960
ggaggtggag gttatagtga gccaaggttg caccagccta ggtgacagag tgagactgtc   52020
tcaaaaaaaa aaaaagaaa gaaaatatac attccatcca gaacttgtta ttctacaagc    52080
aaacatcttt tattggttag acacccatat atgtgtccct aagcaggagg tggatgccaa   52140
ataagagaca aatggcgtaa gacactatga gttgtgtggt gacattgggc atgtcacttc   52200
actccctctg agccttggtt agcttctctg taaaatgaaa ggattatggt aactaagctg   52260
gcttccttcc agctttaaca aactgtatgg aggtacattt tggagttact tgggtaattt   52320
```

```
ttgagtgtga gattggctag aattgcttta atataccaat gtctggcctt agcttttggc    52380
agagtctgtg tgaagaagca gaggcggagt agagttaatt ccgtaagtta acgttcagtt    52440
cgtggcagct ggcaatccaa ccctgggaaa ggctgccgga tttagcaaaa atgcaaggtg    52500
tctgttttta aattcgcaat gaattgggta tcctgcattt tatttggcaa ccctgtcctg    52560
ggactcacac tattcactgt tatcactggt atattcgaag tggtgctgac ttgccctctg    52620
tcttgcaaag tacccggggg tcttttctta tgcttcactg gagtcaaaaa agagaataga    52680
ggaaaagaca atcatattgt tcctttaaga gttaagacca acaagctttc ttctttacat    52740
gttgttttg acatgagcaa actggtgatt aaaaacaact tgggtggctc atacttgtaa     52800
tcccagcact ttggaaagct gaggtgggag aatagcttga ggccaggagt tcaagccagg    52860
gcaatcctat agtgagaccc catctctaca aaagatacaa aaattagcca ggtgtggtgg    52920
tacacctgta gtcccagctg ctccggaggc tgagatggga ggatcagttg agcttgggag    52980
gcagaagttg cagtgagctg agatcgtgcc actgcactcc agcctggaca acagagcaag    53040
accctgtctc aaaaaaggaa acaaaacaac ttggacaatg aaggggggag aaagttcctc    53100
aagaagccaa aattgcacca aatggactcc cagaagccaa gcatttaact tgttaattga    53160
gccctctgtg ggcctgtcta tacttattta aggaacaatc ctatcaagca tagttattgg    53220
gtttctcagc ccaggtagat tagaaatagc agattagagg tgggctaggt ttctagaggt    53280
aaagtacacc agcagaagtt agaagtgaaa gcaaagagcc taacagagga agagaaattc    53340
tttttttttt ttttagacgg agttttgctc ttgttgccca ggctggagtg caatggcgct    53400
atctcggctc aacgcaacct ccgcctcctg ggttcaagtg attctcctgc ctcagcctcc    53460
tgagtagctg ggattacagg catgcaccac cacgcccggc taattttgta tttttagtag    53520
agacagggtt tctccatgtt ggtcatgctg gtctcgaact cctgacctca ggtgatccgc    53580
ccaccttggc ctcccaaagt gctgggatta caggcataag ccactgtgcc cggccaacaa    53640
attcttaaaa ctggacacaa gaacacaaaa cgcttgggct gctgagagat tagaccaaca    53700
accctccacg gctacaaacc ttttccacgt tatatggcac gttataagtg ggtgttccta    53760
gtgatggttc tgatttttt tttaaaaagt ctaaatatgt ttaatgttgt ctcagaagac     53820
aaaatatatt ttagacagat attcctcagt gatgagtaag cctcagctat ctggaaaatt    53880
catgcaggcg ccagagatca ttactgagta attcaagcta ataactgcgt catgctggtt    53940
gtaccctgca tgccaatatc tgctaaaagc agcaccacga aagggaaata cgaatctcac    54000
taagcactca cccattcttg ttaacgacac tggaactgat catccttaat aatacacaga    54060
taaatctatc aggagcattt ccttgcttcc tgtgaaagga agtactcatt ccatgtgtcc    54120
tgtgaaattc agccagcttc gggaagctgg aggaatacat atggccaagc tacctgggca    54180
gagagtagac agggaatgga ggttgggcac agtggctcac acctgtaatt gcagcccttt    54240
agaaggcaaa ggcgggcaga tcacttgagc tcaggtgttc aagaccagcc tgggcaacat    54300
ggctaaaccc cgtctctgca aaaaatacaa aaaaatgagc tgggtatggt agcacacact    54360
tgtggtccca gctacttggg aggctgaggt gggggggttg cttgtgcctg ggagtttgag    54420
gctgcaatga gctgtgattg tgccactgca ctccagcctg gataacagaa tgagaccctg    54480
ttccaaaaat aaaaaataaa atcaaagaca cttaaaaaga tggggaaaag gaaggacagg    54540
cacttaagca agttataagc tactttccta actacacaag tggaatctta agctgaggtt    54600
cccaggagtt gactggagcc agagaagaca gacctatagg agcacccaac tggagtcgcc    54660
```

```
ctccatagta gcccatatgt cttacatgga tcagctttcg tggggcccctt ctactccgtc   54720
tggggaaggg cgtcagatct gtggctctca tgtactgctc agtacactgc cattcccagt   54780
tcttttttc  aaaaaaaaaa aaattgttta cagaatcggc cgggtgtggt ggcttatgcc   54840
tataatacta gcaatttgga aggctgaggt gggtggatca cctgaggtca ggagttcgag   54900
accagcctgg ccaacatggt gaaaccccat cctactaaaa aaaaaaaaa  aaaaaaatta   54960
gctggatgtg gtggcaggcg cctataatct tagctacttg ggaggctgag gcaggagaat   55020
cgcttgaacc tgggaggcag aggctgcagt gagccgagat catgccacgg tactccagcc   55080
tgggtgatag agtgagactc tgtctcaaaa taaataaaat aaaataaaat aaaataaaat   55140
aaaataaaat agtctacaga attaagctgg tccaggaatg cagggcgtc  catttatttg   55200
tctttcaatt gtgggagaaa aaggatttct gttgagacac tgtcgttttg acacacacaa   55260
tattttgatt aatcttgaga ttaaaaatcc tgtgctccaa atcttttaac attaaattat   55320
gcatttaaac aggtttgctc ctaaatctca aaatatggaa agcacctcat gtggctaaat   55380
attttgatga ccaagttttc tggaaggtaa gattttttcac ctattaacgt gatagatttt  55440
gagtgcatga acttaaaaac atacctgggt atatatgttg acttgctgtt tatgagtaaa   55500
acaaaaacaa aaatggagta aggagcattg caggaggaac tagaggagaa acaaatccat   55560
gatatgcatg tgtgtggggg agggtggcgg ggaggtggta aaggtcacca tttccctgat   55620
acctcaaatt cattcagagt cagggatgag acagctttca ctggccacac ttcccctccc   55680
gctatctgca gtcctcagcg tagccaaata gtttgacatg cgggtgacag aacccccgcaa  55740
tgcaaaagct ggaagaaacc tcaagccttg gagtccaacc cctttttga cagatgctaa   55800
gagtggagac atgacttatc aagatcttac aactggctgg gcacggtggc tgacgcctgt   55860
aatcccagca ctttgggagg ctgaggtggg gcgatcacct gaggcagga  gttcgagacc   55920
agcctggcca acgtgtcaaa accccatctc tactaaaaat acaaaagtta gctgggcgtg   55980
gtagcacatg cctgtaatcc cagttactca ggaggctgag gcaagagaat cgcttgaaat   56040
caggaggcag aggttgcagt gagctgagat tgcgccactg cactccagcc tgggtgacaa   56100
gagctgacac tctgtctcaa aaaaaaaaa  aaaaaaaaa  aattcttaca gtgtgtgagt   56160
atccaggctg agtcctgaac acagctcttg ataaatgata acaagcaggc acaaaaaat   56220
tgtagtacag gagtctgagg tcacttagca aagggacata aagttcaaac agctcagcag   56280
ctgctgaggg tcccgtgtta cattgtagca tttgttgttg tgactgggct agaaagaagg   56340
tgaagaaggt tggagctcac tccctgcctc ccctcccact ctcctcccttt tgacctacac   56400
tcatagttca cgcagcactc tgatgtgtcc ccttaggcca tcctctagtc aatgctgtgg   56460
gtaggctgga ccagcaggga ccagtattgt cacagcaagt ccaggccaac agtggtcagg   56520
ctgctgcccg gtgttgtgcc tttgtgagtg gcagatccaa gaccggaacc caggccttct   56580
gagtcccagg ccaatgcttg ccccacccag catccaagat gttgctcact aaagagacag   56640
agaagcagcc ttattatggg cctggacacc tgtgcatgag gggtcaagca gagaggacct   56700
ggggagagac cctgcccctt cttttccttc tccttcctct cctttctctt cttcttcctc   56760
ttcaaatagc ttttttgagt gtaactggca tacaatcaat tgtacatatt taggctgggt   56820
atggtggctc acgcctgtaa tcccagcact ttgggaggcc aaggcgggtg gatcacttga   56880
ggtcaggagt ttgagaccag cctgggcaac ccgtgaaaac cccgtctcca ctaaaactac   56940
aaaaattagc caggcgtggt ggcagctgcc tgtaatcccg ctactcggg  aggctgaggc   57000
aggagaatca cttgaacctg ggaagcgaag tttgcagtga tctgagatca tgccactgca   57060
```

```
ctccagcctg ggtgacagag cgagactttg cctcaaaaac aaaacaaaac aattgtacat  57120
atttaaagtg ttgtaaccaa gtgagttaca gagaaacacc acactttgag cctaattcag  57180
gagtccttta ttagccggcg acctagagac gactagtgct caaaattctc tcggcccaa   57240 agaaggggct agattttctt ttataccttg gtttagaaag gggaggggga attgagctga  57300
agcaatctta cagaagtaaa acaggcaaaa aagttaaaaa gacaaatggt tacaggaaaa  57360
caaacagttc caggtgcagg agctttaaag ccatcacaag gtgacaggtg cggggctct   57420 gggtgctatc tgccggacac aaacgcaggg gcactagagt actatcaccc gggcaaattc  57480
ctgggaactg cggacacagc ttgccacagt accttatcag ctaattgcac tctttgatgt  57540
gctgggagtc agcttgcaca agttaagtcc ttgaggaagg gggtgggtaa ggagccctta  57600
acgtcttgca aatgaaggag ccgaatggaa tccctccggc tttcttagct aagagagagt  57660
caatcaagtt aatacaagtt agggtatcac aaaagtatat aatttgatac attttaacgt  57720
atttatacac tgaagagacc atcaccacca tcaagacaag gagcacaccc atcacttcca  57780
cacacttcct cctgctcctt tgaaattcct cccttcctac ccacctggtc ccacccaaag  57840
gcaaccactg aactactttc tgtcactaag gtttgcgttt tctgtaattt ttttgtttga  57900
gacagggtct cactccgcca cccacaccgt aatgcagtgg caccatcatg actcactgta  57960
gcctcaacct ccccaggctc aggagatcct cccccctcag cctcctgagt agctaggacc  58020
acaggtgtag gccaccatgg caggctaatt tttgtatttt tttgtagaga tggggtttca  58080
ccgtattacc taggctggtc tcgaactcat gggttcaagc aatcctcctg ccttggcctc  58140
tcaaagtgct gggattatag gcatgagcca ctgtgcccag ccctctgtaa tgttacacaa  58200
agggaatcat gcagcacgta ctgcccttgg tctggcctct tttgctcagc atgattattc  58260
tgagaatcat ccgtgttgtt gcgtgtaact gacttcatca gcttctctct gcagctgtca  58320
gctcttggct tctcccaaca gccaatctct ctttatcccc tgcaagtgtt cttgcctatt  58380
tagcagaatc aaggtactct atcgaaaaga ctcggaaaat tggtttaatc tattcattca  58440
ttcctcaggt atttatcgaa taactattct ataccaagta ctatgctaat caaccaagga  58500
cagcacaaac aggagaaatc tccagctcag tcacttgagt tgcaataaat atttgctgga  58560
taggtcaggt gcagtggctc acacttgtaa tcccagcact tgggattca ctgagacggg   58620 aggatctctt gagcccagga ggccaaggct gcagagaacc atgatcatgc cactgcactc  58680
cagcctgggt gacagagtga gatcctgtct ctgaaaaaaa atatttgctg gataaattaa  58740
ggaaatctga cgaaccccat cagtagccat tgcagcaaca ggtaaactag aacgagtgtg  58800
aatttggaat gaggaaaccc gatgttggcc atcattctgt aatgtcatgt attatgtaat  58860
gtattatata ttaatgtatg tattatgtag gcaagttcct tgacctctct cactggtaac  58920
ataagagtag taatctttgt gctacttcac tgggttattt caaagatcaa gtgaggtaat  58980
aatgtctgta acaacattct gtaaaatgca aaccgccaca tgaatgtgaa agtttattac  59040
tagggattta gccaaccaca agggaatgtg tgagcataag agctatcata ttgcaagcct  59100 acagttctg attttgtgct aggtgctttt ccacattacc tgattttatc ctcacaacag   59160
tcctgcataa aagtaagtat gtcgcccagg tgcggtggct catgcctata atcccagcac  59220
tttgggagcc cgaggtgggc aaatcacttg agatcaggag tttgaaacca gcctggtcaa  59280
cgtggtgcaa ccctgtctct actaaaaata caaaaaaaaa ttagacaggc gtggtggtgg  59340
atgcctgtaa tcccagctac ttgggaagct gaggcaggag aatggcttga gcccgggaga  59400
```

```
tggagattgc agtgagatga gattgcgcca ctgcactcca gcctgggtga cagagcaagg    59460
ctatgtctca aaagagaaaa aaaaagtaag tatctcagtc ttgaagatga tgaaatggag    59520
gcctagagag attaagtaac ttgcccaaaa tgacagaact aatgcataga aaagaagaaa    59580
tgtgatgtct tttggctcca aagacacccc acatatgcgt tggttacagt tactagagaa    59640
aagttattcc accccccaccc caccccccaga aatcttctga cttgttttct cgcagttgag    59700
taggaccatt tattcggcag tgtaccattc tcagcttgca gttgaaagcc aaatatccat    59760
taaagaggca aggatgcaaa cttgctaagc tgataaatcc aggggtgatt ttttttttt    59820 ttgcaaacca tccaacaaga cattttaaat actcattgaa tttcatagaa ctgactgcca    59880
ggattggaaa gacattaaag ccagctcagc cactgcctcg ctggttggcc agaccacgcc    59940
tggcacttct ggggagggagc actcaccacc ccccaagggc acccatctca tcctccgaag    60000
gtttatgaaa atgcactcat catttgctaa ttcattccac tacgtgtatt acctaatttg    60060
tgacacgatg tgaagtacca gagagataat tctaaataaa atatagttat gggtctcaag    60120
gagccagata tgctaatctc ctatcctcct gcagtttaca gtggtcctca ccagatactt    60180
atttacaaaa attcagttta ttatttattt ttttgagaca gagtcttgct ctatagctca    60240
ggctagagtg taatggtgtg atctcggctc acttcaacct ctgcctccca ggttcaagtg    60300
attctcctgc ctcaacctcc caagtagctg ggactacagg cacctgccac cacggctaat    60360
ttttggagtt ttagtagaga cagggtttca ccacgttggc caggctggcc tcgaactcct    60420
gacctcaggt gatctgccca catcagcctc ccaaaatgtt gggattacag gcgtgagcca    60480
ccatgcccgg ccaaaacttc agtttataac acaatctttc acgtgtcttc tgctttcatt    60540
aaaagaatag acagttccct tctttatttc agtttaataa accatggatt ttatttcatg    60600
ctttgcaaaa cacaagggct cactgacatg cacttcttaa actaattctg ctggtcgcc    60660 tgtaattcca gcactttggg aggctgaggc cgacagatca cttcaagtca ggagttcaag    60720
accagcctgg ccaatatggt gaaaccacgt ctctaccaaa aatataaaaa attagccagg    60780
tgtggtggtg cgtgactata atcccagcta ctcaggggcc tgaggcagaa aaatcacttg    60840
aacccgggag gcggaggtta cagtgagctg agatcgcgcc actgcactcc agcctgggcg    60900
acagagtgag actctgtctc aaaaaataaa taaatacaaa taatgtaaaa tacgaaacaa    60960
gcaatcctgg cagtagctgc tggaatgaga ggagggagag gtcataggga ggtcgggac    61020 aatggagcat ggagttgtgt tggatttggc taagcagcag gaagtgcaag gcattccaag    61080
caagaggagg ggggcaggtg gggagcatct gcaagaacag aagcagcatg agcaacctgg    61140
ctcggcagtg tgtgaaaagg ctgaaaggtg gctagagcca cttcaatttc atccttcagg    61200
caaatgggaa attcccaaag gttttgagtgg ggaagcaatg cctacaatga agtttgaga    61260 gtgaagcaga gtgatcgaat taagcatgta ggccgagttc tgaaataact gcaatgtgct    61320
gaagatcatc cattggcttc tgaatgagta tttgcagttt attttttaaa atgattttat    61380
tgccaagaaa gataaacact actgttttgg tacaaaaaca taacaaaatg tgttgagtcc    61440
ctcttgctgt tttacgcgaa gttttaaaaa tctactcttg tcacagtggt atcaccccta    61500
cttctgattt caaataaatg ttctagagac acagtaaggg cccaacaaac gcttgttcaa    61560
caacacaagg agagccagct tttaaagtag gaaaacaggc cgggcgccgt ggctcacacc    61620
tgtaatccca cactttggg aggctgaggt gggcagatca cttgaggtca ggagttcaag    61680
aacagcttgg ccaacatggt gaaaccctgt ctctactaaa aacacaaaca ttagccaggc    61740
gtggtggtgc acaccagtag tcccagctat tcaggaggct gaggcaggaa aatggcttga    61800
```

```
actgggagg cagtggttgc agtgagccga gatcgtgcca ctgcactcca gcctggggga   61860
cagagggaga ctccatctca aaataaaaca aacaaaacc aaatcataca aaacattag    61920 ctgggtgtgg tggtgcatac ctgtaatccc agctacttgg gaagctgagg cagaattact  61980 tgaaccctg gggggaggtt gcagtgagct gagatcttgc cactcactc cagcctgggc    62040 aacagagtga ggagactctg tctcaaaaaa tatatatatt aaaaaaaga aaaaaaaag    62100 taaactagga aaacacatca gcagcctgcc aacagactcc cctagcctcg gtgagggcca  62160
gtgttctggg aggcagatct gaattctagt cctagttcac ccactggcag gctggtgccc  62220
ttgggcaggt cgcttctctg gggctcagtt tcttcctcta taaatgaga tcaaatccca    62280 tgttctaaga gtttgtgctc tggagtcaga cagatctggg ttctaccact gccagctctg  62340
tgatcttgta gcttcagtct cgtcatctga catggagata acagtaactg tctcactgtg  62400
ttgttagggt ttaaggaga taatgtatgt gaaatgttag caaacaagtg ttagctaccc   62460
tgatttccgg tttcagagtt ctgtggtccc agtttatgcc acatgcagtg acgttgtatg  62520
gtaggctgtg gtgtggcacc acttcagaac tcagcgcatg cacagcttgc agaagagaag  62580
gccagaggag acctaagaag gctcttcgaa cacttgaaag accggcatgt aggccgggcg  62640
cagtgactca cgcctgtaat cccagcagtt ttggaggtcg aggcgggtgg atcacctgag  62700
tttgggagtt tgataccagc ctgaccaaca aggtgaaacc ccgtctctac taaaaaatac  62760
aaacattagc tgggcatggt ggcgggtgcc tgtaatccca gctactccgg tggttgaggc  62820
agaattgctt gaacccggga ggcagaggtt gcagtgagct gagattgcat cactgcactc  62880
cagcctgaga caagagcgaa actccatctc aaacaaaaca aacaaccaac caaacaaaac  62940
caaaaaaaaa actggcatgt agaagaaaaa tacttttct ctacacttct ccaaagaatt   63000
taactaggcc caggggaggt gcagtataaa tttctaacaa tctcaactgt ctgccaaatg   63060
gaatgagcta cttcatatgg cagtagtgag tcctctgtct ttggaggcat tcaaataaaa  63120
gccagatggc catttatcaa caatccatgt aaaacgttag atgaaataaa acctatatat  63180
ccaagatctc ttccaattca gattttatga aagaatttct aaggtctttg taatgagaca  63240
tttaggctgt ttcaagagat caagccaaaa tcagtatgtg ggttcatctg caataaaaat  63300
gtttgttttg cttttacagt ttcctcattt ggctgttgga ttttaagcaa aagcatccaa  63360 gaaaacaag gcctgttcaa aaacaagaca acttcctctc actgttgcct gcatttgtac   63420
gtgagaaacg ctcatgacag caaagtctcc ttatgtataa tgaaacaagg tcagagacag  63480
atttgatatt aaaaaattaa agactaaaaa cttagtttaa gagtcaattt aataagttta  63540
aaataaatgt ttagtttcat taggatgatg ctatcaatat tttcttggtt acagacacat  63600
tattaaagtt ttgggttaat tttattgaca attcttaaga ttctttctca tgcttaataa  63660
agcatgctac tcagttaact cttgtctaca tcagcaaagc agataataca aaacaggaaa  63720
attacaaatc actgatactt agtccttgtg ggaatcatgc ttttctccca gcagttttac  63780
aaggtggctg gcattccctg agcatattct gaattgcact gtggggaaag aggttgtgct  63840
cagttgtagg gtgggggat gcactgcctg aggattaaaa aactagttct gtgaccgtga   63900
ggaagtcgtt taaatttcca tggtctgttc cctcctatgt gaaaagagaa ggtgggcttc  63960
aacctctaag atcttctcca gttttcacat tttatggact tttgtagaaa aaacatcagg  64020
agttcatgtg ggatgacagc aagtcatttc tttgaggaga gtcttgatca ccaggcaata  64080
ttcacagtgt agagactgtc agatgaccat ggctagcatg gaaatgagac ccacacattt  64140
```

-continued

```
aaatcaccca gcaaatattc cgaaggctaa ttgtagcaca ttttatgaaa gacatttcaa    64200
actgtggtcc tgaagagtgt atcccatctt gcagaggtgg ggagcctggg gggacaagag    64260
ttctgaagag gaagagacaa caagagttcc cagtagctaa tgtttgtcat tctagttgac    64320
cgtgctggtc tattaggcta gtggttcagt acacagatga aatgcaacat ggaacccagt    64380
ttattatcag aacaactaca aagaaattgt ccctgtcta agactggagt gtcaagtctc     64440 tgccctttt tcctttcctt caatggtgga tgtggagtga ctgtgcatcc caccagaacc     64500
acgtgtcatg gctgagtcac atcttcctgc ccttggaatg agaggcacag cggaagacct    64560
tcccatggaa gggacacagg gagcctggtg gctggaccat ggtgcttctc tcttccaaca    64620
cgtccactca ccccttggga gaccctcaaa agccagttac attacatgtt cacagaattt    64680
ttggtaaaag taaataccaa ttatagtgag gaagaattt gaccacggaa tattttaaaa     64740
actaaaaaat gtttatattt catttaacat ttgacacaga agagaccaca tttgaataaa    64800
cacattaaat cttcagagca ctttcattgt ggttttggac ctcagatatg acaaatactt    64860
acattgacaa atccataatt tcttttgtaa tttcttttta tttttacaaa ttataccatg    64920
ataaaatttg acaaaaatta ttcatgtgaa agtttcctct aacattttat aagttaatca    64980
agtgcatacc acaatagatt tttggttgtt gtttaggtgt tctcgtgatt ttagtattac    65040
acaactttaa gctgagacta cactcagaaa taagtttaga aaatggcatt acaaaaggtt    65100
gggagtgagc agtaaaaaaa caaacaaacc catgcagggc tgttgtgctg tgggaaatca    65160
gatgtgttca ctgccataag tcttcagtgc ggccaaactt aaaaaccagc cctctgtgaa    65220
taaaacaaga aatatcacat gactccctga atttgagaaa agagtatgtg agatttcgag    65280
aatggtgtga acaaacaac gaagaataat tgatgagttg tagaagaaat tttggtacga    65340
aatgtatcaa aacagaaact gatcattcta aggtagtgaa ttcttccatt atgttcaact    65400
gtgctattaa ccaccatatt cccaacaacc ttaactttca agtactgaat acacatgtga    65460
cttttaaaaa gttaccagtg tttactatgt aaccattata tgtctgattt tttttttttt    65520
ttttgagaca gagtcttgct ctgtcgccca ggctggagtg cagtggcgtg atctcggctc    65580
actgcaagct ctgcctcccg ggttcatgcc attctcctgc ctct                    65624
```

<210> SEQ ID NO 24
<211> LENGTH: 27
<212> TYPE: DNA
<213> ORGANISM: Artificial sequence
<220> FEATURE:
<223> OTHER INFORMATION: Synthetic sequence: Probe

<400> SEQUENCE: 24
caaaagctga tatgtcatgt ttagtta                                       27

<210> SEQ ID NO 25
<211> LENGTH: 25
<212> TYPE: DNA
<213> ORGANISM: Artificial sequence
<220> FEATURE:
<223> OTHER INFORMATION: Synthetic sequence: Primer

<400> SEQUENCE: 25
gcaaatatgg aaatttgatc atgta                                         25

<210> SEQ ID NO 26

```
<211> LENGTH: 31
<212> TYPE: DNA
<213> ORGANISM: Artificial sequence
<220> FEATURE:
<223> OTHER INFORMATION: Synthetic sequence: Primer

<400> SEQUENCE: 26
cttaatcaca agattatttt cagaatctaa c                                    31

<210> SEQ ID NO 27
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 27
gggccttgga caagttgtta                                                 20

<210> SEQ ID NO 28
<211> LENGTH: 26
<212> TYPE: DNA
<213> ORGANISM: Artificial sequence
<220> FEATURE:
<223> OTHER INFORMATION: Synthetic sequence: Primer

<400> SEQUENCE: 28
ggcaaatatg gaaatttgat catgta                                          26

<210> SEQ ID NO 29
<211> LENGTH: 250
<212> TYPE: DNA
<213> ORGANISM: Homo sapiens

<400> SEQUENCE: 29
ttattcccaa ggcaaatatg gaaatttgat catgtactaa tcataataaa gctggattct     60
ctttaagaga ttgagaaatt aaaaggcaaa agctgatata tcatgtttag ttatattgtg    120
agtcttataa gaagctggga ggcaacccca ttaactcacc agaatacaga actcagtctc    180
acaacttaga tataattcct ctcaaacctt ttcctcaaag attaaattct gaaaataatc    240
ttgtgattaa                                                          250

<210> SEQ ID NO 30
<211> LENGTH: 249
<212> TYPE: DNA
<213> ORGANISM: Homo sapiens

<400> SEQUENCE: 30
ttattcccaa ggcaaatatg gaagtttgat catatgctaa tcatactaaa gctggattct     60
ctttaagaga ttgagaaatt aaaaggcaaa agctgatata tcatgtttag ttatactgtg    120
agtcttataa gaagctggga ggcaacccca ttaactcacc agaatacaga actcagtctc    180
acaacttaaa tataattcct ctcaaacctt ttcctcaaag ttaaattctg aaaataatct    240
tgtgattaa                                                           249

<210> SEQ ID NO 31
<211> LENGTH: 249
```

```
<212> TYPE: DNA
<213> ORGANISM: Homo sapiens

<400> SEQUENCE: 31
ttattcccaa ggcaaatatg gaaatttgat catgtactaa tcatactaaa gctggattct      60
ctttaagaga ttgagaaatt aaaaggcaaa agctgatatg tcatgtttag ttatattgtg     120
agtcttataa gaagctggga ggcaacccca ttaactcacc agaatacaga actcagtctc     180
acaacttaaa tataattcct ctcaaacctt ttcctcaaag ttaaattctg aaaataatct     240
tgtgattaa                                                             249

<210> SEQ ID NO 32
<211> LENGTH: 250
<212> TYPE: DNA
<213> ORGANISM: Homo sapiens

<400> SEQUENCE: 32
ttattcccaa ggcaaatatg gaaatttgat catgtactaa tcataataaa gctggattct      60
ctttaagaga ttgagaaatt aaaaggcaaa agctgatatg tcatgtttag ttatattgtg     120
agtcttataa gaagctggga ggcaacccca ttaactcacc agaatacaga actcagtctc     180
acaacttaga tataattcct ctcaaacctt ttcctcaaag attaaattct gaaaataatc     240
ttgtgattaa                                                            250
```

DISCRIMINATION OF BLOOD TYPE VARIANTS

FIELD OF THE INVENTION

The invention relates to methods for genotyping and blood cell antigen determination, which in particular may discriminate the RHD*r's or RHD*r's-like blood type variants, which encode $C^{+W}$ antigen and no D antigen, from RHD*DIIIa, RHD*DIVa-2 and other blood type variants. The invention also relates to products, in particular, probes, primers and kits for use in such methods.

BACKGROUND TO THE INVENTION

The success of blood transfusion often depends on the degree of compatibility between donor and recipient. The degree of compatibility, in turn, is a function of the similarity in Red Blood Cell (RBC) antigen content between donor and recipient. Expression of many RBC antigens in an individual can be predicted from the analysis of their genomic DNA. Therefore, analysis of donor and/or recipient DNA can be used to facilitate blood matching and thus enable proper blood transfusion practice.

Hemolytic reactions are more common in multi-transfused than in singly transfused individuals, not only because of the increased probability of such an event as the number of transfused units increases, but also because of the accumulative nature of the immune response in the recipient. An example of a condition whose treatment includes repeated blood transfusions is Sickle Cell Disease (SCD). From the above follows that a high degree of compatibility with donor blood is often critical for the long-term success of transfusion in SCD patients.

While SCD is more prevalent among individuals of African ancestry, the blood donor population in the USA and other Western countries is largely Caucasian. As a consequence of this disparity, differences in RBC antigens between both racial groups often become responsible for blood transfusion failures in SCD patients.

The genetic variant RHD*DIIIa-CE(4-7)-D, also known as RHD-CE-$D^S$, RHD-CE(4-7)-D, (C)$ce^S$, or $r'^S$, (RHD*$r'^S$ henceforth) can be found in up to 5-10% of the African-American population, but is extremely rare in Caucasians. This variant poses a special challenge to blood transfusion because it encodes a rather complex antigen profile, which includes absence of D antigen, altered forms of C ($C^{+W}$) and e antigens, expression of low-frequency VS antigen, no expression of V antigen, and absence of the high-frequency $hr^B$ antigen. Among them, D and C antigens are the clinically most relevant ones.

The antigenic complexity of RHD*$r'^S$ correlates with its genetic complexity, which includes a substitution of part of RHD exon 3, RHD exons 4-7, and the intervening introns by their RHCE counterparts, a G>T substitution at position 186 (exon 2), a C>T substitution at position 410 (hybrid exon 3), a C>G substitution at position 733 (exon 5), and a G>T substitution at position 1006 (exon 7). In addition to the changes in the RHD gene, RHD*$r'^S$ occurs in cis with RHCE*$ce^S$1006T, an RHCE gene that also encodes substitutions C>G at position 733 (exon 5) and G>T at position 1006 (exon 7).

To add to the antigenic and genetic complexity, knowledge about the molecular basis of RHD*$r'^S$ is incomplete. For instance, the precise points of RHCE/RHD recombination have not been reported to date. Furthermore, two types of RHD*$r'^S$ variant have been described and named Type 1 and Type 2, which differ not only in their genetic composition but also in their antigen profiles.

Several publications (Westhoff et al., Transfusion (2010), 50: 1303-1311, Pham et al., Transfusion (2009), 49: 495-504, and Tax et al., Transfusion (2002) 42: 6234-6644) have uncovered the genetic similarity between RHD*$r'^S$ and other RHD variants, in particular RHD*DIIIa and RHD*DIVa/RHD*DIVa-2 (RHD*DIVa-2 henceforth). A number of molecular methods for the specific detection of RHD*$r'^S$ rely on the detection of polymorphisms located in D-CE hybrid exon 3 locus of RHD. These polymorphisms are now known to be shared with variants RHD*DIIIa and RHD*DIVa-2. Consequently, to date, identification of RHD*$r'^S$ in a sample by DNA analysis requires detection of hybrid exon 3 polymorphisms and discrimination from RHD*DIIIa and RHD*DIVa-2. This discrimination is clinically relevant since the latter variants encode a different antigen profile, which includes expression of partial D and absence of $C^{+W}$.

EP1780217 describes the detection of RHD positive haplotypes in D-negative individuals. Silvy et al., British Journal of Haematology, (2012 Dec. 30) doi: 10.1111/bjh. 12179 [Epub ahead of print], describe identification of a polymorphism said to be restricted to the (C)$ce^S$ type 1 haplotype. WO2012/171990 describes discrimination of blood type variants in a method making use of polymorphisms in intron 7 of the RHD gene and/or intron 7 of the RHCE gene. EP2471949 describes a method for the identification by molecular techniques of genetic variants that encode no D antigen ($D^-$) and altered C antigen ($C^{+W}$).

Antibody reagents commonly used to detect C antigen do not discriminate between $C^{+W}$ and $C^+$. Therefore, the phenotype is often reported as $C^+$. In cases where the antibody reagent does discriminate between $C^{+W}$ and $C^+$ but the sample contains a normal RHCE*C allele in trans to a RHD*$r'^S$ allele, $C^{+W}$ is obscured by $C^+$, resulting in a $C^+$ phenotype for the sample. Therefore, RHCE*C needs to be tested for and shown absent prior to assignment of a $C^{+W}$ phenotype to a sample. Accordingly, there remains a need for further methods for distinguishing RHD*r'S from RHD*DIIIa and RHD*DIVa-2. The present invention addresses these and other objects.

SUMMARY OF THE INVENTION

The present inventors have surprisingly found that methods and, in particular, PCR primers as described herein are able to amplify a portion of intron 3 of the RHD gene found in $r'^S$ samples in a specific manner, and that this specificity is retained even under multiplex PCR conditions. Considerable disadvantages of previously-described primers and reaction methods are addressed by the methods and primers of the present invention, as demonstrated by the examples herein. The present invention mitigates false positive readings displayed by previously-described methods and primers, and is advantageously able to discriminate $r'^S$ from closely-related alleles, including a newly-described variant of RHD*DIIIa.

Accordingly, the present invention provides, in a first aspect, an oligonucleotide polymerase chain reaction (PCR) primer, the nucleotide sequence of which is of the formula:

X—Y—Z wherein:
X is $X_1$ or $X_2$, wherein:
$X_1$ is the final n nucleotides in the nucleotide sequence ATATGGAAATTTGATCATGT (SEQ ID NO: 1), wherein n is a number between 0 and 20, inclusive; and $X_2$ is a variant of $X_1$ differing by no more than one nucleotide substitution;

Y is $Y_1$ or $Y_2$, wherein:

$Y_1$ is the nucleotide sequence $AS_1TAATS_2ATAC$ (SEQ ID NO: 2), wherein $S_1$ and $S_2$ are independently selected from G and C; and $Y_2$ is a variant of $Y_1$ differing from $Y_1$ by no more than one nucleotide substitution, provided that said nucleotide substitution is not a substitution of the first A or final C of $Y_1$;

Z is the first m nucleotides in the nucleotide sequence TAAAG, wherein m is a number between 0 and 5, inclusive.

In some cases, the primer of this and other aspects of the invention is such that $X_1$ is the nucleotide sequence of AAATTTGATCATGT (SEQ ID NO: 3) or ATGT. That is to say, n may, in some cases, be 14 or 4. In certain cases, n may be 0, 1, 2, 3, 4, 5, 6, 7, 8, 9, 10, 11, 12, 13, 14, 15, 16, 17, 18, 19 or 20.

In some cases in accordance with this and other aspects of the present invention, $Y_1$ is selected from the group consisting of: ACTAATCATAC (SEQ ID NO: 4); ACTAATGATAC (SEQ ID NO: 5); and AGTAATCATAC (SEQ ID NO: 6). Preferably, if $S_1$ is G, $S_2$ is C. Likewise, if $S_1$ is C, $S_2$ is preferably G. Thus, the selection of $S_1$ and $S_2$ may be chosen to keep the number of mismatches with the intended target template sequence to not more than one nucleotide mismatch. However, it is specifically contemplated herein that the number of mismatches may be more than one. For example, in certain cases, both $S_1$ and $S_2$ may be G. Alternatively, the number of nucleotide mismatches may be zero. In certain cases, both $S_1$ and $S_2$ may be C.

In some cases in accordance with this and other aspects of the present invention, m is 0. Therefore, the primer of the invention may have no Z, with the result that the last nucleotide in Y (which is a C that corresponds to the C/A polymorphic nucleotide at position 3046 of RHD intron 3, as numbered in FIG. 7) is the 3' nucleotide of the primer of the invention. Alternatively, m may be 1, 2, 3, 4 or 5.

In some cases in accordance with this and other aspects of the present invention, the primer is not more than 30, 29, 28, 27, 26, 25, 24, 23, 22, 21 or 20 nucleotides in length. In some cases, the primer may be at least 10, 11, 12, 13, 14, 15, 16, 17, 18, 19, 20, 21, 22, 23, 24 or at least 25 nucleotides in length. In certain cases the primer may be between 10 and 30 nucleotides in length, such as between 15 and 25 nucleotides in length. Particular cases include a primer in accordance with the first aspect of the invention which has a length of exactly 10, 11, 12, 13, 14, 15, 16, 17, 18, 19, 20, 21, 22, 23, 24, 25, 26, 27, 28, 29 or 30 nucleotides.

In some cases in accordance with this and other aspects of the present invention, the primer may be DNA or RNA. The primer is preferably DNA.

In some cases in accordance with this and other aspects of the present invention, the primer may include one or more, e.g. 1, 2, 3, 4 or 5 altered or non-natural bases and/or derivatised or modified nucleotide bases. In particular, one or more bases (e.g. a 5' or a 3' base) may be biotinylated or conjugated to a detectable label. Alternatively or additionally, one or more bases (e.g. 1, 2, 3, 4 or 5 nucleotide bases) may be locked nucleic acid (LNA) bases.

In some cases in accordance with this and other aspects of the present invention, the nucleotide sequence of the primer consists of a nucleotide sequence selected from the group consisting of:

(i) AAATTTGATCATGTACTAATCATAC; (SEQ ID NO: 7)

(ii) ATGTACTAATCATAC; (SEQ ID NO: 8)

(iii) AAATTTGATCATGTACTAATGATAC; (SEQ ID NO: 9) and (iv) AAATTTGATCATGTAGTAATCATAC. (SEQ ID NO: 10)

In some cases in accordance with this and other aspects of the present invention, the primer is suitable for use as a forward PCR primer in a PCR amplification of a portion of the $r'^S$ allele of intron 3 of the RHD gene.

In a second aspect, the present invention provides a plurality of oligonucleotide primers comprising:

(i) an oligonucleotide primer of the first aspect of the invention; and (ii) (a) a reverse primer that hybridises to a portion of intron 3 of $r'^S$, or its complement, which portion includes at least one position of single nucleotide polymorphism (SNP) that differs between $r'^S$ and RHD; or (b) one or more primers that hybridise to a region of the RHD gene and or the RHCE gene.

Preferably, said reverse primer (ii) (a) hybridises to the reverse complement of a portion of the $r'^S$ intron 3 sequence that is shown in FIG. 7 and which lies 3' of position 3050, as numbered in FIG. 7. In some cases in accordance with this and other aspects of the present invention said reverse primer hybridises to a portion of intron 3 of $r'^S$, or its complement, which portion includes the G/A polymorphism position 3189 of intron 3 of the RHD gene, said numbering being as shown in FIG. 7.

In some cases in accordance with the second aspect of the present invention, the plurality of primers comprises:

(i) an oligonucleotide primer of the first aspect of the invention; and (ii) at least one primer selected from the group consisting of:

(a) an oligonucleotide primer of between 26 and 30 nucleotides in length comprising the nucleotide sequence GGAAAAGGTTTGAGAGGAATTATATT (SEQ ID NO: 11) or a variant thereof differing by not more than 3 (e.g. not more than 2 or not more than 1) nucleotide substitutions from the nucleotide sequence of SEQ ID NO: 11, provided that said substitutions do not include substitution of the final T in the nucleotide sequence of SEQ ID NO: 11;

(b) an oligonucleotide primer consisting of the nucleotide sequence GGAAAAGGTTTGAGAGGAATTATATT (SEQ ID NO: 11);

(c) the RHCE c forward primer consisting of the nucleotide sequence TGGGCTTCCTCACCTCAAA (SEQ ID NO: 12);

(d) the RHCE c reverse primer consisting of the nucleotide sequence TGATGACCACCTTCCCAGG (SEQ ID NO: 13);

(e) the RHCE C forward primer consisting of the nucleotide sequence GGCCACCACCATTTGAA (SEQ ID NO: 14);

(f) the RHCE C reverse primer consisting of the nucleotide sequence GGTAGCAGGCGTCTGTAAAAA (SEQ ID NO: 15);

(g) the RHCE exon 1 forward primer consisting of the nucleotide sequence CATAGACAGGCCAGCACAG (SEQ ID NO: 16);

(h) the RHCE exon 1 reverse primer consisting of the nucleotide sequence TGCCCCTGGAGAACCAT (SEQ ID NO: 17);

(i) the RHCE exon 5 forward primer consisting of the nucleotide sequence AAATTAAAATAAG-CATTTGACCATC (SEQ ID NO: 18);

(j) the RHCE exon 5 reverse primer consisting of the nucleotide sequence CCTGAGATGGCTGTCAC-CAC (SEQ ID NO: 19);

(k) the RHCE exon 7 forward primer consisting of the nucleotide sequence ACATGCCATTGCCGTTC (SEQ ID NO: 20); and (l) the RHCE exon 7 reverse primer consisting of the nucleotide sequence TCTCACCTGCCAATCTGCT (SEQ ID NO: 21).

In some cases the plurality of oligonucleotide primers comprise at least:

an oligonucleotide primer of the first aspect of the invention, and an oligonucleotide primer of between 26 and 30 nucleotides in length comprising the nucleotide sequence GGAAAAGGTTTGAGAGGAATTATATT (SEQ ID NO: 11) or a variant thereof differing by not more than 3 (e.g. not more than 2 or not more than 1) nucleotide substitutions from the nucleotide sequence of SEQ ID NO: 11, provided that said substitutions do not include substitution of the final T in the nucleotide sequence of SEQ ID NO: 11.

In some cases the plurality of oligonucleotide primers comprise at least the primer pair:

```
                                       (SEQ ID NO: 7)
AAATTTGATCATGTACTAATCATAC;
and (SEQ ID NO: 8)
GGAAAAGGTTTGAGAGGAATTATATT.
```

In a third aspect the present invention provides a kit for assessing a subject's blood type, said kit comprising:

a plurality of primers of the second aspect of the invention;

optionally, one or more probes and/or primers that span one or more polymorphic positions in intron 3, exon 3, exon 4, intron 7 and/or exon 7 of the RHD gene locus; and/or optionally, one or more probes and/or primers that span one or more polymorphic positions in exon 7 of the RHCE gene locus.

In a fourth aspect, the present invention provides a system for use in determining a subject's blood type, the system comprising:

a kit of the third aspect of the invention; and at least one detector arranged to detect a signal from detectably labelled DNA obtained from said subject or a detectably labelled amplicon produced by PCR amplification carried out on DNA obtained from said subject;

at least one controller in communication with the at least one detector, the controller being programmed with computer-readable instructions to transform said signal into predicted blood type haplotypes, and optionally, to transform said predicted blood type haplotypes into a predicted blood type phenotype.

In a fifth aspect the present invention provides a method for determining the presence or absence of, or for discriminating between, blood type alleles in a DNA-containing sample, which method comprises amplification by polymerase chain reaction (PCR) of at least a portion of intron 3 of the RHD gene, wherein said PCR employs at least a forward primer and a reverse primer each capable of hybridising to the $r'^S$ sequence set forth in SEQ ID NO: 31 (FIG. 7), or its complement, and wherein said forward primer is the primer of the first aspect of the invention.

In some cases in accordance with the method of this and other aspects of the invention, the blood type alleles are alleles that comprise an RHD/RHCE hybrid exon 3. In particular, the blood type alleles may be selected from the group consisting of: RHD*$r'^S$; RHD*$r'^S$-like; RHD*$r'^S$ Type 1; RHD*$r'^S$ Type 2; RHD*DIIIa; RHD*DIIIa IVS3+3100G; RHD*DIII_FN; RHD*DIVa-2; RHD*DIVa; RHD*DIII-type4; RHD*DIII-type6; RHD*DIII-type7; RHD*DIII-type8; RHCE*$ce^S$; RHCE*$ce^S$1006T; RHCE*$ce^S$1006C; RHCE*ce733G; RHCE*ce48C,733G,1025T; RHCE*ce48C,697G,733G; RHCE*ce340T,733G; and RHCE*ce48C,733G,748A.

In some cases in accordance with the method of this and other aspects of the invention the PCR amplifies $r'^S$, but does not amplify one or more of: RHD; RHCE*ce; RHD*DIIIa; RHD*DIIIa IVS3+3100G; and RHD*DIVa. In particular, said PCR may in certain cases amplify $r'^S$, but not any of RHD; RHCE*ce; RHD*DIIIa; RHD*DIIIa IVS3+3100G; and RHD*DIVa.

In some cases in accordance with the method of this and other aspects of the invention the method is for discriminating $r'^S$ from RHD*DIIIa IVS3+3100G. The ability to distinguish $r'^S$ from the newly-described variant, "RHD*DIIIa IVS3+3100G", which as far as the present inventors are aware has not previously been reported, is a major advance. The newly-described variant, "RHD*DIIIa IVS3+3100G" comprises the same RHD intron 3 position 3100 A to G polymorphism that has previously been reported to be specific for $r'^S$ (see Silvy et al., 2012). Reliance on the presence of the RHD intron 3 position 3100 A to G polymorphism to uniquely identify $r'^S$ would be expected to result in false positive results. The provision of a method that discriminates $r'^S$ from RHD*DIIIa IVS3+3100G is expected to provide a significant clinical contribution.

The method in accordance with this and other aspects of the present invention utilises a forward primer of the first aspect of the invention. Particular examples include a primer that consists of the nucleotide sequence AAATTTGATCATG-TACTAATCATAC (SEQ ID NO: 7). The method further utilises a suitable reverse primer, which may be any reverse primer capable of yielding a PCR product when used in combination with the forward primer of the first aspect of the invention. In certain cases, the reverse primer is capable of hybridising to a portion of intron 3 of $r'^S$, or its complement, which portion includes at least one position of single nucleotide polymorphism (SNP) that differs between $r'^S$ and RHD. In a certain cases, said position of SNP comprises the G/A polymorphism at position 3189 of intron 3 of the RHD gene, said numbering being as shown in FIG. 7 (see also SEQ ID NO: 31). In some cases, the reverse primer is of between 26 and 30 nucleotides in length and comprises the nucleotide sequence GGAAAAGGTTTGAGAGGAATTATATT (SEQ ID NO: 11). In certain cases, the reverse primer consists of the nucleotide sequence GGAAAAGGTTTGAGAGGAAT-TATATT (SEQ ID NO: 11).

In some cases in accordance with the method of this and other aspects of the invention the PCR is multiplex PCR. The multiplex PCR may further comprise amplification of one or more RHD and/or RHCE gene segments other than RHD intron 3. In some cases, the one or more RHD and/or RHCE gene segments are selected from the group consisting of: RHCE c; RHCE C; RHCE exon 1; RHCE exon 5; and RHCE exon 7. Accordingly, the method may employ additional PCR primers to be used in multiplex with the above-described PCR primers. In certain cases, the multiplex PCR further comprises employing 1, 2, 3, 4, 5, 6, 7, 8, 9 or all 10 of the following primers:
(i) the RHCE c forward primer consisting of the nucleotide sequence TGGGCTTCCTCACCTCAAA (SEQ ID NO: 12);
(ii) the RHCE c reverse primer consisting of the nucleotide sequence TGATGACCACCTTCCCAGG (SEQ ID NO: 13);
(iii) the RHCE C forward primer consisting of the nucleotide sequence GGCCACCACCATTTGAA (SEQ ID NO: 14);
(iv) the RHCE C reverse primer consisting of the nucleotide sequence GGTAGCAGGCGTCTGTAAAAA (SEQ ID NO: 15);
(v) the RHCE exon 1 forward primer consisting of the nucleotide sequence CATAGACAGGCCAGCACAG (SEQ ID NO: 16);
(vi) the RHCE exon 1 reverse primer consisting of the nucleotide sequence TGCCCCTGGAGAACCAT (SEQ ID NO: 17);
(vii) the RHCE exon 5 forward primer consisting of the nucleotide sequence AAATTAAAATAAGCATTTGACCATC (SEQ ID NO: 18);
(viii) the RHCE exon 5 reverse primer consisting of the nucleotide sequence CCTGAGATGGCTGTCACCAC (SEQ ID NO: 19);
(ix) the RHCE exon 7 forward primer consisting of the nucleotide sequence ACATGCCATTGCCGTTC (SEQ ID NO: 20); and
(x) the RHCE exon 7 reverse primer consisting of the nucleotide sequence TCTCACCTGCCAATCTGCT (SEQ ID NO: 21). Preferably, the primers are employed in pairs, said primers being paired as follows: (i) with (ii); (iii) with (iv); (v) with (vi); (vii) with (viii); and (ix) with (x).

In some cases in accordance with the method of the present invention, the sample is a sample which has previously been determined to comprise an RHD-RHCE hybrid exon 3. Alternatively, the sample may be suspected to comprise an RHD-RHCE hybrid exon 3 or be an unknown sample. The method may therefore further comprise a preceding step of determining whether the sample contains an RHD-RHCE hybrid exon 3.

In some cases in accordance with the method of the present invention, the method further comprises determining the presence or absence of an RHCE*C allele in the sample. In some cases the method further comprises genotyping the sample at one or more positions of polymorphisms in the RHD and/or RHCE gene loci. In certain cases, the method comprises genotyping the sample at position 410 of the RHD exon 3. In certain cases, the method comprises genotyping the sample at position 602 of the RHD exon 4. In certain cases, method comprises genotyping the sample at position 1048 of the RHD exon 7. In certain cases, the method comprises genotyping the sample at position 1006 of the RHCE exon 7. In certain cases, the method comprises genotyping the sample at position 3100 of the RHD intron 3.

In some cases in accordance with the method of the present invention, the method comprises genotyping not more than 50, 40, 30, 25, 20, 15, or not more than 10, single nucleotide polymorphic positions in the RHD gene locus and/or the RHCE gene locus.

In some cases in accordance with the method of the present invention, the method further comprises predicting an RHD phenotype and/or an RHCE phenotype for the subject based on, at least, the degree of amplification by PCR of said at least one portion of intron 3 of the RHD gene. This may, for example, include a visual or computer-aided inspection of the intensity of a band on a gel where the intensity is related to the degree of amplification of the PCR product. The skilled person will of course be readily able to make us of suitable techniques to evaluate the degree of PCR amplification, e.g., for classification of a sample as containing $r'^S$. Such techniques include, without limitation, real time PCR (qPCR), Luminex bead-based detection and agarose gel-based evaluation. The method may comprise detecting a positive result for $r'^S$-specific PCR amplification and thereby classifying a sample as containing an $r'^S$ allele. In some cases, the phenotype prediction is further based on:
(i) the presence or absence of an RHD/RHCE hybrid exon 3;
(ii) the identity of one or both alleles present at position 602 of the RHD exon 4;
(iii) the identity of one or both alleles present at position 1048 of the RHD exon 7;
(iv) the presence or absence of an RHCE*C allele in the RHCE gene locus;
(v) the identity of one or both alleles present at position 1006 of the RHCE exon 7; and/or
(vi) the identity of one or both alleles present at position 3100 of the RHD intron 3.

In some cases the sample is found to contain $r'^S$ and is therefore predicted to have $C^{+W}$ serology.

In accordance with this and other aspects of the present invention, the sample is preferably obtained or has been previously obtained from a human subject. In some cases the subject is undergoing, or is a candidate for, blood transfusion or bone marrow transplantation. In some cases the subject has sickle cell disease (SCD) or Thalassemia major. In some cases the subject has non-Caucasian ancestry. In some cases, the subject has African ancestry.

In accordance with this and other aspects of the present invention, the sample may be any suitable biological sample from which it is possible to obtain nucleic acid, particularly genomic DNA, for use in a PCR reaction. Suitable samples include any material of bodily origin (liquid, solid or aspirate) such as blood, hair, cheek cells and skin cells.

In accordance with this and other aspects of the present invention, the sample may be subjected to one or more treatments to extract a nucleic acid prior to or as part of said amplification by PCR.

In accordance with this and other aspects of the present invention, the method may comprise Allele-Specific Polymerase Chain Reaction (ASP).

In accordance with this and other aspects of the present invention, the method may comprise labelling a nucleic acid obtained from the sample or labelling the amplicon produced by said PCR amplification.

In accordance with this and other aspects of the present invention, the method may further comprise carrying out serological analysis on a blood sample that has been obtained from the subject. This may be particularly useful to corroborate or clarify a phenotype prediction made. Combining the genotype-based prediction of blood type with a serological-based prediction may be useful, e.g., to improve accuracy or to resolve ambiguous results. However, it is also specifically contemplated herein that the method of this and other aspects of the present invention may not comprise carrying out serological analysis. Removing the need to carry out serological analysis provides considerable savings in terms of time, cost and/or resources.

In a sixth aspect the present invention provides a method of blood matching, the method comprising:
carrying out the method of the fifth aspect of the invention on a recipient sample from a recipient subject in need of donor blood and on a donor sample from a potential donor subject;
comparing the blood type alleles present in the recipient sample with those present in the donor subject and thereby determining the compatibility of the recipient subject to receive blood from the potential donor subject.

In accordance with the present invention, the subject may be undergoing, or may be a candidate for, blood transfusion. In some cases, the subject may have SCD, or any other disease requiring repeated blood transfusions, such as Thalassemia major or certain blood cell malignancies.

In accordance with the present invention, the subject may be of non-Caucasian race. In particular, the subject may be of African ancestry (e.g. "Black persons"). In certain cases, the subject may have an ancestral origin in a Mediterranean country.

In accordance with the method of the invention, the sample may be any suitable biological sample from which it is possible to amplify at least a portion of intron 3 of the RHD gene locus and/or from which it is possible to determine the genotype of the subject at one or more polymorphic positions in the RHD gene and/or the RHCE gene. In certain case, the sample may conveniently take the form of a blood sample.

In certain cases in accordance with the method of the invention, the method may comprise carrying out an Allele-Specific Polymerase Chain Reaction (ASP) and/or Allele-Specific Hybridization (ASH).

In certain cases in accordance with the method of this and other aspects of the invention, the method may comprise labelling a nucleic acid obtained from the sample or labelling an amplicon derived from a nucleic acid obtained from the sample. The label is preferably a detectable label. In some cases, DNA derived from the sample, e.g. PCR product resulting from use of the DNA from the sample as template, may be labelled using a fluorescent label or dye (e.g. by conjugating said fluorescent label or dye to the PCR product before or after fragmentation of the PCR product).

In some cases, the method in accordance with the sixth aspect of the invention may be carried out for a plurality of recipient subjects and a plurality of potential donor subjects.

The invention will now be described in more detail, by way of example and not limitation, by reference to the accompanying drawings. Many equivalent modifications and variations will be apparent to those skilled in the art when given this disclosure. Accordingly, the exemplary embodiments of the invention set forth are considered to be illustrative and not limiting. Various changes to the described embodiments may be made without departing from the scope of the invention. All documents cited herein are expressly incorporated by reference.

DESCRIPTION OF THE FIGURES

FIG. 2 shows Luminex intensity results for a variety of samples $r'^S$, RHD*DIIIa IVS3+3100G and other non-$r'^S$ samples following multiplex PCR using the $r'^S$-specific primers shown in Table 1 and one or more primer pairs shown in Tables 2 and 3;

FIG. 3 shows a table of certain RHD and RHCE exon and intron features for $r'^S$, DIIIa, DIVa and the new variant "RHD*DIIIa IVS3+3100G";

FIG. 7 shows an alignment of a portion of intron 3 of the RHD gene numbered positions 3001 to 3250, numbered according to the RHD sequence (upper row). An identical nucleotide to that above is represented by a dot; a omitted/deleted nucleotide (i.e, a gap) is represented by a dash. The sequences shown are (from top to bottom): RHD, RHCE*ce, $r'^S$, DIVa, DIIIa and the newly-described variant RHD*DIIIa IVS3+3100G (shown as #425). The locations of the reference forward primer and reverse primer are indicated by shaded boxes.

SEQUENCE LISTING

Figure 1:
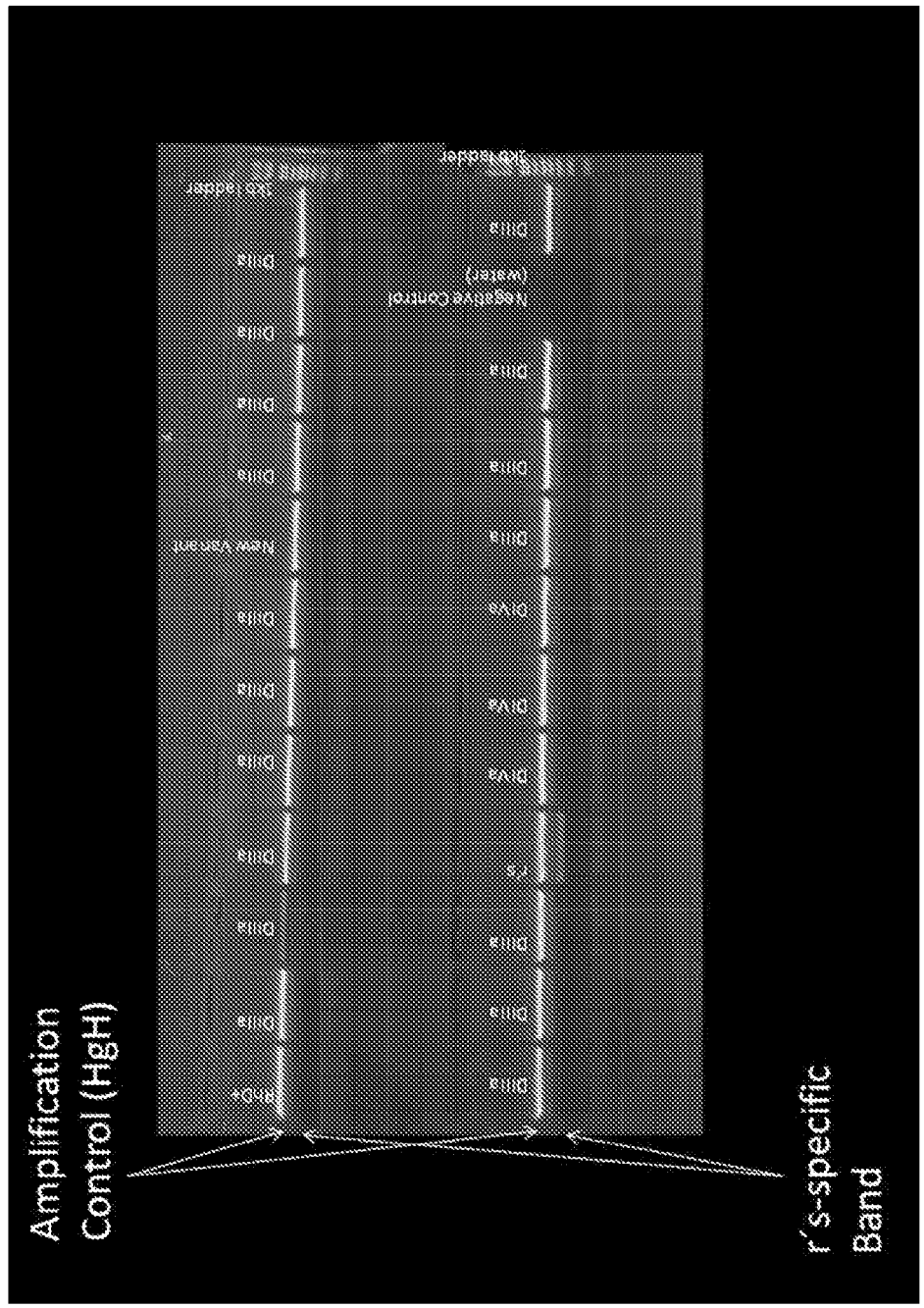
FIG. 1 shows a gel image depicting the PCR results of a reaction utilising primers for an amplification control (HgH) (upper band) and $r'^S$ (lower band) for a variety of samples (including RhD$^+$, DIIIa, RHD*DIIIa IVS3+3100G, $r'^S$, DIVa and a negative control.

The Sequence Listing is submitted as an ASCII text file in the form of the file named Sequence_Listing.txt, which was created on Mar. 8, 2013, and is 172.704 bytes, which is incorporated by reference herein.

DETAILED DESCRIPTION OF THE INVENTION

The present invention finds use in the determination of the clinically relevant RHD− and RHCE− encoded antigen phenotypes of a blood sample. The invention provides a method for detecting the presence or absence of, or for discriminating between, blood type variants, which method comprises amplification by polymerase chain reaction (PCR) of at least a portion of intron 3 of the RHD gene, wherein said PCR employs at least a forward primer and a reverse primer each capable of hybridising to the $r'^S$ sequence set forth in SEQ ID NO:31, or its complement, and wherein said forward primer nucleotide sequence is of the formula:

$$X—Y—Z$$

wherein:
X is $X_1$ or $X_2$, wherein:
  $X_1$ is the final n nucleotides in the nucleotide sequence ATATGGAAATTTGATCATGT (SEQ ID NO: 1), wherein n is a number between 0 and 20, inclusive; and
  $X_2$ is a variant of $X_1$ differing by no more than one nucleotide substitution;
Y is $Y_1$ or $Y_2$, wherein:
  $Y_1$ is the nucleotide sequence AS$_1$TAATS$_2$ATAC (SEQ ID NO: 2), wherein $S_1$ and $S_2$ are independently selected from G and C; and
  $Y_2$ is a variant of $Y_1$ differing from $Y_1$ by no more than one nucleotide substitution, provided that said nucleotide substitution is not a substitution of the first A or final C of $Y_1$;

Z is the first m nucleotides in the nucleotide sequence TAAAG, wherein m is a number between 0 and 5, inclusive.

Advantageously, the method of the present invention may further comprise determining the presence or absence of an RHD/RHCE hybrid exon 3 in said sample and/or genotyping a sample obtained from a human subject at one or more positions in intron 7 of the RHD gene and/or in intron 7 of the RHCE gene. Blood typing by making use of intron 7 polymorphisms is described in WO2012/171990, the entire contents of which is expressly incorporated herein by reference. Blood typing by making use of a combination of polymorphisms in the RHD gene and/or the RHCE gene are described in US2012/0172239 and EP2471949, the entire contents of which are both expressly incorporated herein by reference.

The Rh blood group D antigen is encoded by the RHD gene, which comprises 10 exons. The complete RHD gene sequence is available at NCBI Reference Sequence: NG_007494.1 No. NG_007494.1, GI:171184448, (SEQ ID NO: 22), the entire contents of which is incorporated herein by reference.

The Rh blood group C antigen is encoded by the RHCE gene, which comprises 10 exons. The complete RHCE gene sequence is available at NCBI Reference Sequence: NG_009208.2, GI:301336136, (SEQ ID NO: 23), the entire contents of which is incorporated herein by reference.

The term "sample" as used herein is intended to encompass any material (solid, liquid or aspirate) obtained directly or indirectly from a human subject and from which the identity of one or more nucleotides in a relevant genomic locus (e.g. intron 7 or the RHD locus and/or intron 7 of the RHCE locus) can be determined. In particular, the term "sample" includes any biological fluid such as blood, plasma, urine, saliva, cerebrospinal fluid and interstitial fluid, any solid matter, such as tissue, bone and hair, any cell or cell extract, any derived cell line, such as an immortalised tumour cell line and stem cell line, an extract of any of the preceding sample types, such as fixed or paraffin-embedded tissue. In certain preferred embodiments, the sample is an extract of human genomic DNA, optionally amplified and/or purified.

As used herein, the term "genotyping" is intended to encompass any method for determining the identity of the nucleotide at a particular position such as a polymorphic position at a specified locus. Thus, genotyping includes identifying one or both alleles of a particular gene. Genotyping may employ any of a variety of techniques, including but not limited to, allele-specific hybridisation, allele-specific PCR, sequencing of all or part of a gene.

Unless specified otherwise, all nucleic acid sequences, such as primer sequences, are set forth herein in the direct 5' to 3'. Thus, for example, the primer sequence AAATTTGATCATGTACTAATCATAC (SEQ ID NO: 7) may equally be written as 5'-AAATTTGATCATGTACTAATCATAC-3' (SEQ ID NO: 7).

As described herein in detail, certain blood type alleles are less common and a typically referred to as "variants" (e.g. RHD*$r^S$). Variant blood type alleles are in some cases referred to herein simply as "blood type variants".

Broadly, the present invention provides methods and products for the identification by molecular techniques of genetic variants RHD*$r^S$ or RHD*$r^S$-like, which encode no D antigen (D−), an altered form of D antigen (partial D), altered forms of C ($C^{+W}$) and e antigens, expression of low-frequency VS antigen, no expression of V antigen, and/or no $hr^B$ antigen ($hr^{B-}$) in blood cells. The present inventors have found that amplification of a region of intron 3 of the RHD locus may be $r^S$-specific when primers as described in detail herein are employed. This $r^S$-specific amplification enables discrimination between variants RHD*$r^S$ or RHD*$r^S$-like and other RHD/RHCE hybrid exon 3 variants, including but not limited to RHD*DIIIa, RHD*DIIIa IVS3+3100G, RHD*DIII_FN and RHD*DIVa-2. In certain embodiments, the method of the invention provides considerable efficiency savings in comparison with, for example, full DNA sequencing, or genotyping of a large number of polymorphisms, or determining the phenotype by serological methods. Nevertheless, it is specifically contemplated that the method of the invention may, in some cases, involve DNA sequencing in order to genotype the sample obtained from the subject.

A wide variety of techniques are suitable and may be used in accordance with the present invention. Allele-specific oligonucleotides, for example, used in a competitive or non-competitive PCR (ASP henceforth), can also be used to detect genetic variants.

In accordance with any aspect of the present invention, functional segments or their portions may be amplified, for example by PCR, using as a template genomic DNA. Amplified functional segments or their portions can be labelled (e.g. with a fluorescent label) to allow for their detection, and optionally fragmented to facilitate their pairing with oligonucleotide probes.

In accordance with any aspect of the present invention, labelled and fragmented functional segments or their portions may be incubated under conditions that maximize the sensitivity and specificity of pairing with probes attached to the solid support. The presence of probe-paired functional segments or their portions may be determined indirectly from the measurement of label, usually a fluorochrome, attached to the solid support. This measurement is referred to herein as signal intensity. By way of example, the fluorescence emitted by the fluorochrome may be collected by means of a fluorescence detection device, such as a confocal scanner.

EXAMPLES

Discrimination among genetic variants that share a RHD/RHCE hybrid exon 3 but encode different forms of D Ag (Partial D Ag vs. No D Ag) and RhC Ag (Normal C Ag vs. Altered/Weakened C Ag, sometimes abbreviated as $C^{+W}$)

The following example relates to a method of discriminating among RHD/RHCE hybrid exon 3 variants RHD*r's, RHD*DIIIa and RHD*DIVa-2 and a newly-discovered variant designated herein as "RHD*DIIIa IVS3+3100G".

Genomic DNA was extracted from nucleated cells in a blood sample by cell lysis. Extracted DNA was purified on an affinity column. Both, cell lysis and DNA purification are performed with a QIAamp Blood kit (Qiagen, Germany) by following manufacturer protocols and recommendations. Purity of DNA was determined by spectrophotometry on a Nanodrop instrument (Nanodrop, DE). Only DNA solutions with an $OD_{260}/OD_{280}$ 1.8±0.2 proceeded to subsequent analysis.

$r^S$-specific PCR Amplification

Purified DNA was used as a template for multiplexed Polymerase Chain Reaction (PCR) amplification of the gene segments of interest in a GeneAmp 9700 thermal cycler (Perkin-Elmer, CA). Primer sequences were as follows (5'-3'):

TABLE 1

| $r'^s$ Forward | AAATTTGATCATGTACTAATCATAC | SEQ ID NO: 7 |
|---|---|---|
| Reverse | GGAAAAGGTTTGAGAGGAATTATATT | SEQ ID NO: 11 |

Cycling conditions consist of a denaturation/polymerase activation step at 95° C. for 15 min, followed by 40 cycles of denaturation at 95° C. for 30 sec, annealing at 60° C. for 30 sec, extension at 72° C. for 80 sec, and a final extension step at 72° C. for 7 min.

Amplified DNA was separated by electrophoresis on a 2% agarose gel, stained with SYBR Safe dye (Invitrogen, OR), and photographed under UV illumination. Amplification vs. no amplification of a segment was determined visually by a trained laboratory technician.

The following samples of known identity were subjected to allele-specific PCR using the above $r^{\prime S}$-specific primer pair: RhD$^+$ (one sample), DIIIa (17 samples), the newly-discovered variant "RHD*DIIIa IVS3+3100G" (one sample), $r^{\prime S}$ (one sample), DIVa (3 samples) and a water negative control (one sample). As a positive control for PCR amplification, primers for amplification of HgH were also employed. The PCR reaction products were run on an agarose gel (see FIG. 1).

specific (due to the design of the forward primer). In other words, it is not necessary for the detection probe itself to interrogate a sequence that is specific to $r^{\prime S}$.

As a non-limiting example, the procedure for Luminex® xMAP®-based detection employed herein, was as follows:

DNA Sample Preparation

Human genomic DNA was extracted from whole blood with EDTA as anti-coagulant. Genomic DNA extraction was carried out in the pre-PCR area.

Genomic DNA input was 100 ng. Genomic DNA purity ($OD_{260}/OD_{280}$ ratio) was in the 1.63-1.95 range.

Genomic DNA samples were stored frozen at −15 to −25° C. for up to one month. Multiple freeze/thaw cycles were avoided.

The following procedure was applied:

Procedure

The ID-CORE XT™ protocol consists of 4 steps:

As shown in FIG. 1, the upper band which indicates the presence of the HgH positive control PCR product is visible for all samples with the exception of the water negative control. The $r^{\prime S}$-specific band (lower band) is visible only on the is sample (lower panel; lane 4). These results clearly demonstrate that $r^{\prime S}$-specific PCR is able to discriminate between $r^{\prime S}$ and other RHD/RHCE hybrid exon 3 variants such as DIIIa, DIVa and the newly-discovered variant "RHD*DIIIa IVS3+3100G".

Multiplex PCR and Probe-Based Genotyping

The following primers (5'-3') were used in multiplex with the $r^{\prime S}$ primers described above:

TABLE 2

| RHCE c | Forward | TGGGCTTCCTCACCTCAAA | SEQ ID NO: 12 |
|---|---|---|---|
| | Reverse | TGATGACCACCTTCCCAGG | SEQ ID NO: 13 |
| RHCE C | Forward | GGCCACCACCATTTGAA | SEQ ID NO: 14 |
| | Reverse | GGTAGCAGGCGTCTGTAAAAA | SEQ ID NO: 15 |

TABLE 3

| RHCE Exon 1 | Forward | CATAGACAGGCCAGCACAG | SEQ ID NO: 16 |
|---|---|---|---|
| | Reverse | TGCCCCTGGAGAACCAT | SEQ ID NO: 17 |
| RHCE Exon 5 | Forward | AAATTAAAATAAGCATTTGACCATC | SEQ ID NO: 18 |
| | Reverse | CCTGAGATGGCTGTCACCAC | SEQ ID NO: 19 |
| RHCE Exon 7 | Forward | ACATGCCATTGCCGTTC | SEQ ID NO: 20 |
| | Reverse | TCTCACCTGCCAATCTGCT | SEQ ID NO: 21 |

The following probe sequence was used to determine the presence of absence of the intron 3 amplicon:

(SEQ ID NO: 24)
CAAAAGCTGATATGTCATGTTTAGTTA

A single probe may be used to determine presence or absence of the intron 3 amplicon because the PCR is allele- Each batch of samples was processed with a negative control (molecular biology grade water that is known to be free of any DNA contamination).

I. Amplification

Work in the pre-PCR area and use aerosol-barrier tips. Use a new tip for each DNA sample.

Briefly vortex and spin tubes before use.

It is not necessary to set up the PCR reaction on ice.

1. Turn on the thermocycler.
2. Take the following reagents out of the refrigerator and freezer: ID-CORE XT™ PCR Master Mix and HotStarTaq® DNA polymerase, respectively.

Note: HotStarTaq® DNA polymerase must be removed from the freezer immediately before use and returned to the freezer immediately after use. Alternatively use ice or a microtube cooler. The stock enzyme should be mixed by gently flicking the tube.

3. Set up the ID-CORE XT™ PCR reaction mix as shown in the following table (all volumes in μL):

| Number of samples | 1 | 8 | 24 | 48 |
|---|---|---|---|---|
| ID-CORE XT ™ PCR Master Mix | 22.5 | 180 | 540 | 1080 |
| HotStarTaq ® DNA Polymerase (5 U/μL) | 0.5 | 4 | 12 | 24 |

NOTE:
the stated volumes already include an excess to account for pipetting error.

4. Vortex and spin the ID-CORE XT™ PCR reaction mix.

5. Immediately dispense 20 µL per sample into the wells of a 96-well PCR plate.
6. Add 5 µL of sample DNA, positive control DNA and negative control to the appropriate wells in this order.
7. Seal the plate with the adhesive film.
Work in the post-PCR area.
8. Spin down the PCR plate to collect the liquid at the bottom of the wells.
9. Verify that all wells are properly sealed and that the lid of the thermocycler has reached the pre-set temperature.
10. Place the plate in the thermocycler. Place the compression pad over the plate.
11. Close the thermocycler lid and start the ID XT PCR amplification program.

|  | Temperature | Time | Cycles |
| --- | --- | --- | --- |
| Polymerase Activation | 95° C. | 15 min | 1 |
| Denaturation | 95° C. | 30 s | 40 |
| Annealing | 60° C. | 30 s | 40 |
| Extension | 72° C. | 80 s | 40 |
| Final extension | 72° C. | 7 min | 1 |
| Hold | 4° C. | ∞ | 1 |

Amplification reaction volume: 25 µL

II. Hybridization
Work in the post-PCR area. Use a new tip for each sample. Whenever necessary during dispensing steps, dry the surface of the Costar plate using a low-lint wipe.
Handling and Storage of the ID-CORE XT™ Beads Master Mix:
  a. Beads settle and aggregate with time. Before pipetting, bring them to a homogeneous suspension by vigorous vortexing for 30 seconds.
  b. During ID-CORE XT™ Beads Master Mix dispensing, keep beads in suspension by vortexing frequently (every 8 samples).
  c. Do not centrifuge the plate once the ID-CORE XT™ Beads Master Mix has been dispensed to avoid bead aggregation.
  d. Beads contain an internal fluorescent dye. To avoid photobleaching, protect them from light during storage and usage.
Luminex® System Preparation:
  a. Turn on the Luminex® 100/200™ system between 30 minutes and 4 hours before assaying the samples.
  b. Set the XYP instrument heater temperature at 52° C. and verify that the heater block is on the plate holder.
  c. Perform Luminex® 100/200™ daily startup maintenance.
1. Turn on the thermocycler.
2. Take the ID-CORE XT™ Beads Master Mix out of the refrigerator and let equilibrate to room temperature.
3. Vortex the ID-CORE XT™ Beads Master Mix for 30 seconds.
4. Dispense 46 µL of the ID-CORE XT™ Beads Master Mix into a Costar plate. Avoid bubble formation during dispensing.
5. Spin down the PCR plate to collect the liquid at the bottom of the wells.
6. Add 4 µL of PCR product into each well of the Costar plate.
7. Mix gently by pipetting up and down several times. Avoid bubble formation during dispensing and pipetting.
8. Seal the plate with a BioRad sealing film.
9. Verify that all wells are properly sealed and that the lid of the thermocycler has reached the pre-set temperature.
10. Place the plate and the corresponding silicone compression mats on the thermocycler block.
11. Close the thermocycler lid and start the ID XT HYB hybridization program.

|  | Temperature | Time |
| --- | --- | --- |
| Denaturation | 95° C. | 2 min |
| Hybridization | 52° C. | 30 min |
| Hold | 52° C. | ∞ |

12. During the hybridization step prepare the labeling mix (see Labeling section) and perform the "Create a New Batch" step in the Luminex® software (see Data Acquisition section).
Note: PCR products must be labeled immediately after hybridization. The process cannot be stopped after the hybridization step.
III. Labeling
Work in the post-PCR area.
1. Bring the following reagents to room temperature: SAPE and SAPE Dilution Buffer.
2. Prepare the labeling mix as shown in the following table (all volumes in µL):

| Number of samples | 1 | 8 | 24 | 48 |
| --- | --- | --- | --- | --- |
| SAPE Dilution Buffer | 87 | 696 | 2088 | 4176 |
| SAPE | 4.6 | 36.8 | 110 | 221 |

NOTE:
the stated volumes already include an excess to account for pipetting error.

3. Vortex the labeling mix and keep it protected from light at room temperature.
4. At the 52° C. hold step, open the thermocycler lid and remove the compression pads and the sealing film with care, while keeping the plate on the thermocycler for the labeling step.
5. Dispense 80 µL of the labeling mix into each well of the hybridization plate and mix gently by pipetting up and down once.
6. Analyze the samples using the Luminex® system immediately after labeling.
IV. Data Acquisition and Analysis
Luminex® System Preparation:
Refer to Luminex® User's Manual (Luminex® 100™ IS 2.3. User Manual, Luminex® 200™ User Manual, or xPONENT® 3.1 Software Manual) for instrument preparation and operation, including daily startup, calibration, maintenance, and shutdown procedures.
1. Select Create a New Batch from an existing Protocol in the HOME page (for Luminex® IS 2.3 software) or Batches tab option (for Luminex® xPONENT® 3.1 software) and select the corresponding protocol.
2. Enter the sample IDs.
3. Follow the stepwise instructions that appear on the screen for creating batches. For further instructions on creating batches and multibatches, refer to the corresponding Luminex® User's Manual.
4. Select the Eject icon to eject the plate holder. Place the hybridization plate in the Luminex® XYP instrument heater block present on the plate holder.
5. Select the Retract icon. The samples are now ready to be analyzed.

6. Start the analysis process by clicking the Start icon (for Luminex® IS 2.3 software) or the Run icon (for Luminex® xPONENT® 3.1 software).
7. After a batch is complete, the data are exported as a Comma Separated Values (csv) file. This file is saved in a folder with the Batch Name entered into the Luminex® software.
8. Perform Luminex® 100/200™ daily shutdown maintenance.
9. The system can be turned off at this point if it is not going to be used for the remainder of the day.

Proprietary software (Progenika Biopharma S.A.) is used to transform fluorescence intensity values for the particular allelic variants detected, singly or in combination, into blood group genotypes, and from genotypes into predicted blood group phenotypes.

Figure 2:
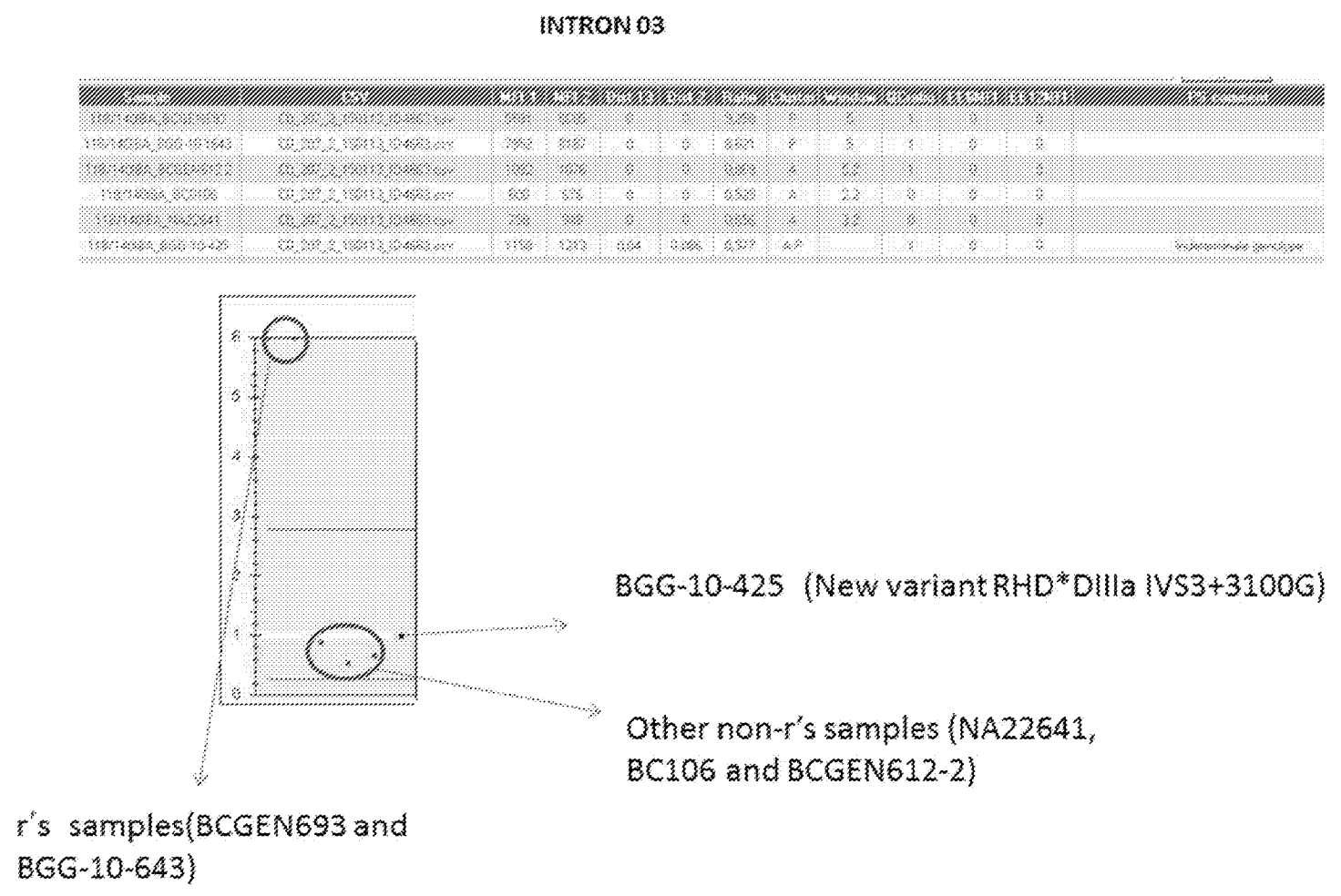

FIG. 2 shows the output and graphical representation (vertical axis is "normalised intensity") of a Luminex assay for $r'^S$ samples, the newly-discovered variant "RHD*DIIIa IVS3+3100G", and other non-$r'^S$ samples following multiplex PCR using the $r'^S$-specific primers shown in Table 1 and one or more primer pairs shown in Tables 2 and 3. The data shown in FIG. 2 confirm that the $r'^S$ samples are successfully amplified by PCR in multiplex and that the Luminex normalised intensity signal is markedly higher for the $r'^S$ samples than for non-$r'^S$ samples, including the newly-discovered variant "RHD*DIIIa IVS3+3100G". Indeed, the separation of normalised signal (greater than 6-fold higher for $r'^S$ samples) provides clear unambiguous discrimination between $r'^S$ samples and closely related non-$r'^S$ samples, despite the relatively less stringent PCR conditions utilised for multiplex PCR. These results therefore underscore the surprising adaptability of the primers of the present invention, in particular the forward primer as set forth in Table 1, for use in multiplex allele-specific PCR for identification of $r'^S$ samples.

As shown in FIG. 3, the ability of the $r'^S$-specific primers of the present invention to work in multiplex with primers for amplification of other segments of the RHD gene and/or RHCE gene loci allows for efficient use of sample, e.g., to interrogate other polymorphisms relevant to the classification of blood type variants. In particular, segments including all or part of one or more RHD and/or RHCE exons and/or introns may be amplified and the amplification products interrogated by allele-specific probes in order to detect the presence or absence of, and/or identity of: an RHCE c; an RHCE C; RHCE exon 1; RHCE exon 5; RHCE exon 7; an RHD/RHCE hybrid exon 3 allele; a G/C polymorphism at position 602 of RHD exon 4; a C/G polymorphism at position 1048 of RHD exon 7; presence or absence of an RHCE*C allele; a G/T polymorphism at position 1006 of RHCE exon 7; and/or a G/A polymorphism at position 3100 of RHD intron 3.

Comparison with a Previously-Described Primer

Silvy et al., British Journal of Haematology, (2012 Dec. 30) doi: 10.1111/bjh.12179 [Epub ahead of print], describe PCR amplification of a portion of intron 3 of the RHD gene. The amplification is said to be selective for $r'^S$ (referred to therein as (C)ce$^S$ type 1 haplotype. The primer pair employed by Silvy et al. included (see FIG. 1 and Supporting information Appendix S1 of Silvy et al.):

a forward primer ("RHD-for") that is specific for RHD-containing sequence having the sequence (5' to 3'):

(SEQ ID NO: 25)
GCAAATATGGAAATTTGATCATGTA;

a reverse primer ("RHCE-rev") that is specific for RHCE-containing sequence having the sequence (5' to 3'):

(SEQ ID NO: 26)
CTTAATCACAAGATTATTTTCAGAATCTAAC;

a control reverse primer ("RHDCE-rev") that hybridised to both RHD-containing and RHCE-containing sequence having the sequence (5' to 3'):

(SEQ ID NO: 27)
GGGCCTTGGACAAGTTGTTA.

The method taught by Silvy et al. relies on the amplification of a 240 bp amplicon by the primer pair RHD-for and RHCE-rev being specific for $r'^S$, as compared with, e.g., RHD*DIVa2 and RHD*DIIIa (see Silvy et al., FIG. 1(B)). Although Silvy et al. report amplification of 52 (C)ce$^S$ type 1 haplotype samples and negative amplification of all other samples in a 118 sample set, regardless of the RHD and RHCE alleles present, this method suffers from a number of important drawbacks. In particular, the specificity is achieved by means of the intersection of the two specific primers, RHD-for and RHCE-rev, rather than either primer itself being specific for $r'^S$. This means that, for example, the RHD-for primer also hybridises to other RHD sequence-containing template, including RHD*DIIIa and RHD*DIVa2.

As described below, the present inventors have found that the method and primers of Silvy et al. result in poor discrimination of $r'^S$ from, e.g., RHD*DIIIa and RHD*DIVa2 under the less stringent PCR conditions typically employed in multiplex PCR.

Moreover, Silvy et al. teach that the IVS3+3100a>g SNP is specific to (C)ce$^S$ type 1 haplotype (i.e. $r'^S$). However, the present inventors have now discovered that this is not the case. In particular, a variant provisionally termed "RHD*DIIIa IVS3+3100G" has been identified herein, which is not $r'^S$, but actually a variant of RHD*DIIIa having the same intron 3 position 3100 A to G polymorphism. Therefore, reliance on the presence of the intron 3 position 3100 A to G polymorphism in order to identify $r'^S$ can and will lead to false positive results where a "RHD*DIIIa IVS3+3100G" sample would be incorrectly assigned as an $r'^S$ sample. This is clinically relevant because "RHD*DIIIa IVS3+3100G" is C-serologically, rather than C$^{+W}$. Thus, reliance on the presence of intron 3 position 3100 A to G polymorphism in order to identify $r'^S$ is undesirable.

As shown in the alignment of FIG. 7, the forward primer of Silvy et al. (RHD-for) will anneal to all of the following: RHD, $r'^S$, DIVa, DIIIa and the newly-described "RHD*DIIIa IVS3+3100G" sample. Although the intersection of sequences that match the RHD-for and RHCE-rev primers of Silvy et al. can be expected to be confined to $r'^S$, the amplification will only be specific under stringent conditions. Under less stringent conditions, the forward primer of Silvy et al. results in a number of non-specific amplifications. In contrast, the forward primer of the present invention is specific only to $r'^S$.

In the process of designing the forward primers of the present invention, the inventors sought to mitigate the drawbacks associated with the forward primer disclosed in Silvy et al.

Figure 4:
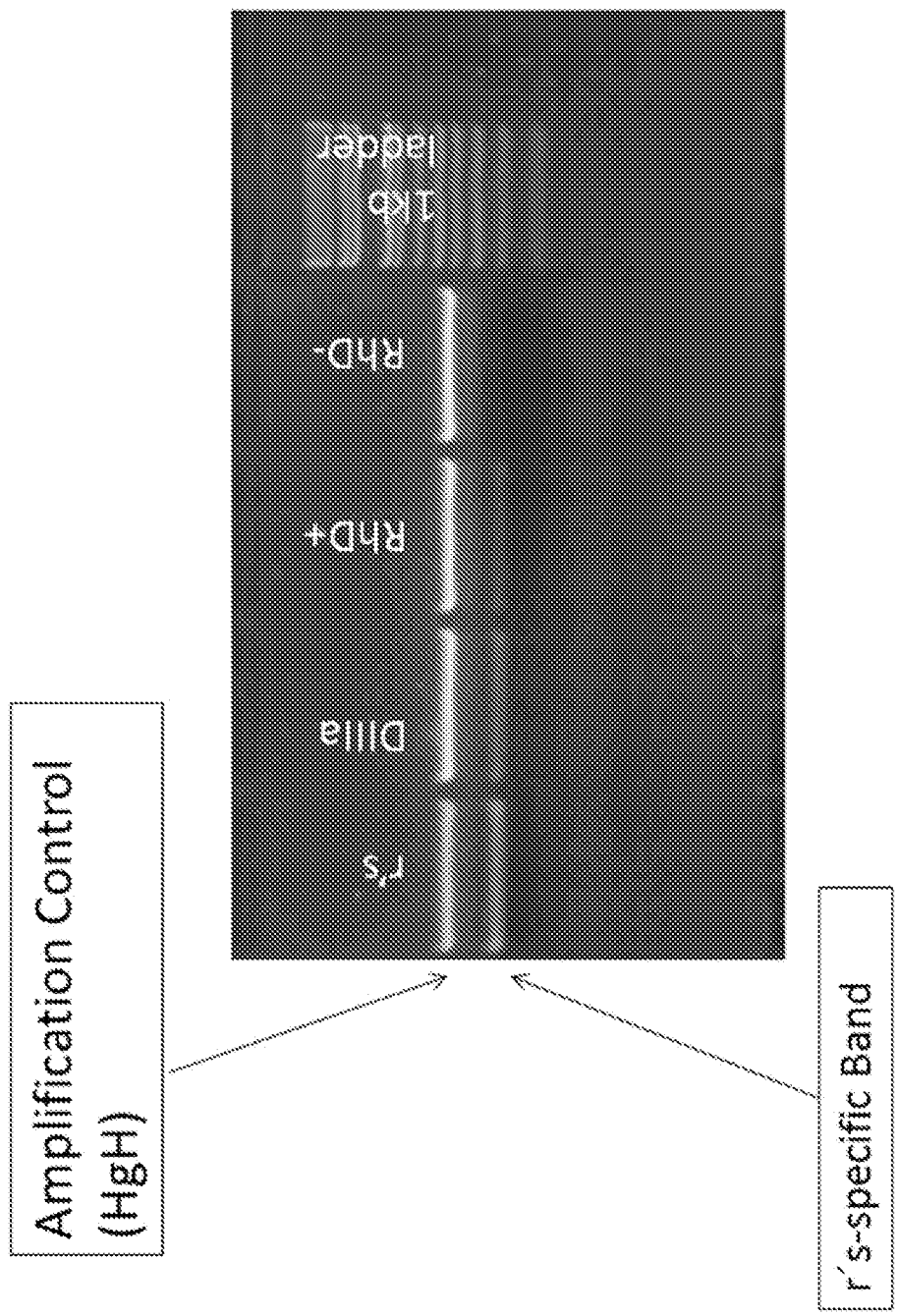
FIG. 4 shows a gel image depicting the PCR results of a reaction utilising primers for an amplification control (HgH) (upper band) and $r'^S$ (lower band) for a variety of samples (including RhD$^+$, DIIIa, RhD$^-$ and $r'^S$)

FIG. 4 shows the results of using the RHD-for primer of Silvy et al. having the sequence GCAAATATGGAAATTTGATCATGTA (SEQ ID NO: 25) together with the RHCE-specific reverse primer having the sequence GGAAAAGGTTTGAGAGGAATTATATT (SEQ ID NO: 11) under PCR conditions suitable for multiplex PCR. The upper band shows the amplification control (HgH), while the lower band is, theoretically, an amplicon which is specific for r$^{'S}$. Lane 1 shows that the sample "BGG-10-656", which is a known r$^{'S}$ sample is indeed amplified by the above primer combination. However, lane 2, which is the sample "BGG-10-628", being a known DIIIa sample, and lane 3, which is "L22", a known RhD+ sample, both exhibit positive amplification of the supposedly r$^{'S}$-specific amplicon. These results demonstrate that the forward primer RHD-for of Silvy et al. results in false positive results under the conditions tested. These results may be contrasted with the results obtained when using a forward primer of the present invention, in which case no such false positive results were found.

Figure 5:
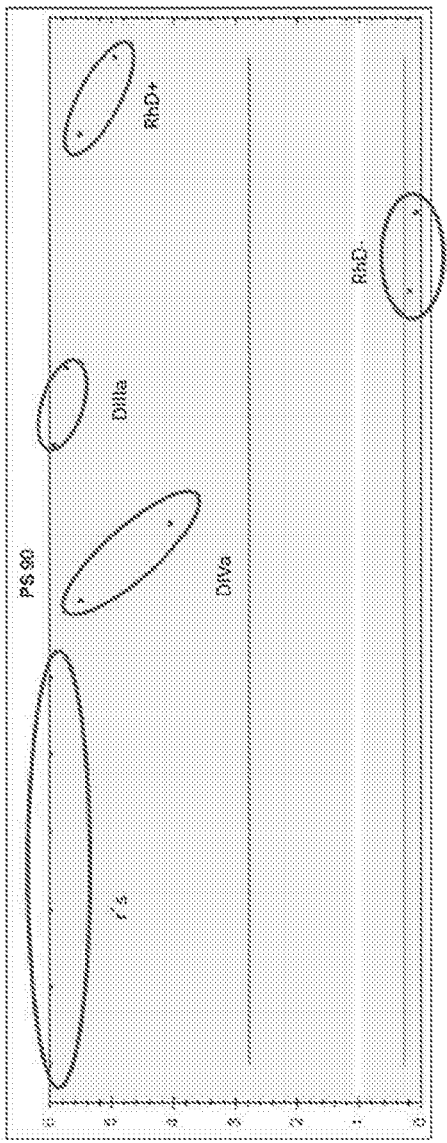
FIG. 5 shows Luminex intensity results for a variety of samples $r'^S$, $r'^S$/RHD+ heterozygous, $r'^S$ hemizygous, DIVa-2, DIIIa, RHD− and RHD+ samples.

The results shown in FIG. 5 likewise demonstrate that the forward primer of Silvy et al. results in non-specific amplification and therefore false positive results. In particular, samples which are known DIVa, DIIIa and RhD+ all exhibited Luminex mean fluorescence intensity signal above the threshold line to be classified as r$^{'S}$ (as did the samples known to be r$^{'S}$). Samples known to be RhD− did not exhibit positive results in this experiment. These data can be contrasted with the r$^{'S}$-specific results shown in FIG. 2, wherein a forward primer of the present invention was employed.

Variant Primers of the Invention

The present inventors sought to provide primers that contain sequence modifications compared with the "reference" forward primer having the sequence AAATTTGATCATGTACTAATCATAC (SEQ ID NO: 7). By way of example, the following changes were made to the "reference" forward primer sequence, while retaining r$^{'S}$-specificity.

In a first modification, the reference primer was shortened by deleting 10 nucleotides at the 5' end, in order to decrease annealing temperature for the PCR. This modification results in the forward primer of the invention having the following nucleotide sequence: ATGTACTAATCATAC (SEQ ID NO: 8).

In a second modification, the reference primer was altered by introducing one nucleotide substitution (replacing a C with a G) to increase specificity. This modification results in the forward primer of the invention having the following nucleotide sequence (the substitution position being underlined): AAATTTGATCATGTACTAAT$\underline{G}$ATAC (SEQ ID NO: 9).

In a third modification, the reference primer was altered by introducing one nucleotide substitution that differs from the substitution described above in relation to the second modification. This substitution was also a replacement of a C with a G to increase specificity, but was at a different position. This modification results in the forward primer of the invention having the following nucleotide sequence (the substitution position being underlined): AAATTTGATCATGTA$\underline{G}$TAATCATAC (SEQ ID NO: 10).

Figure 6:
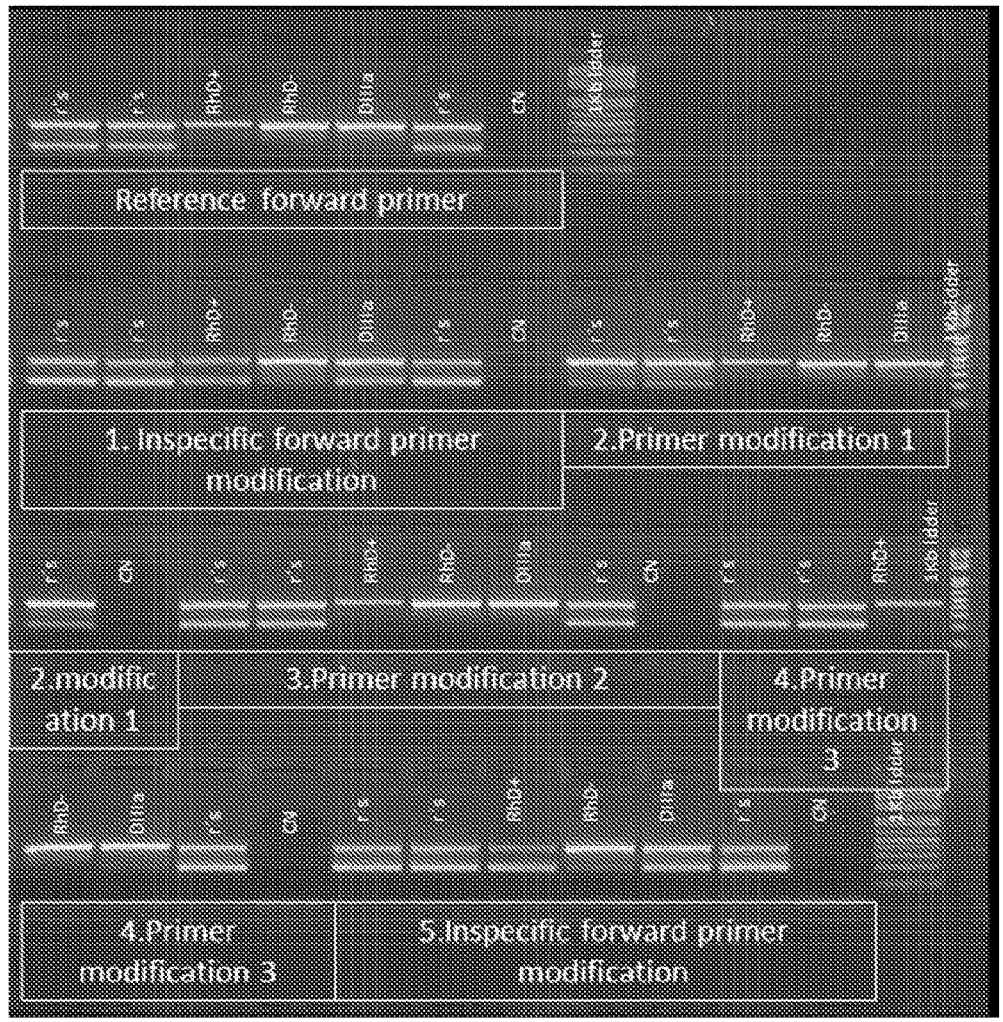
FIG. 6 shows a gel image depicting the PCR results of a number of PCR reactions comparing different primer combinations. An amplification control (HgH) (upper band) and $r'^S$ (lower band) are shown for a variety of samples ($r'^S$, RhD$^+$, RhD$^-$, DIIIa and a negative control.

FIG. 6 shows PCR results obtained using: the reference forward primer of the invention AAATTTGATCATGTACTAATCATAC (SEQ ID NO: 7); the "inspecific" forward primer of Silvy et al. GCAAATATGGAAATTTGATCATGTA (SEQ ID NO: 25); the variant primer of the invention having modification 1 ATGTACTAATCATAC (SEQ ID NO: 8); the variant primer of the invention having modification 2 AAATTTGATCATGTACTAATGATAC (SEQ ID NO: 9); the variant primer of the invention having modification 3 AAATTTGATCATGTAGTAATCATAC (SEQ ID NO: 10); and a modified version of the "inspecific" forward primer of Silvy et al. having the sequence GCAAATATGGAAATTTGATCATGTA (SEQ ID NO: 28). In all cases the reverse primer used was GGAAAAGGTTTGAGAGGAATTATATT (SEQ ID NO: 11).

FIG. 6 shows the PCR amplification results of the above-described primers. The top band is a control and the lower band is intended to be an r$^{'S}$-specific amplification product, to the extent that the primers used in fact amplify in an r$^{'S}$-specific manner under the conditions employed. As shown in FIG. 6, the reference forward primer (upper panel) exhibits r$^{'S}$-specific amplification (positive for three known r's samples (lanes 1, 2 and 6) and negative for non-r$^{'S}$ (RhD+ in lane 3, RhD− in lane 4 and DIIIa in lane 5). The negative control of lane 7 shows no amplification.

The inspecific forward primer in box 1 (second panel down; left hand side) exhibits positive r$^{'S}$ band presence of not only r$^{'S}$ samples, but also RhD+ and DIIIa (see lanes 3 and 5), thus confirming false positive results.

The primer modification 1 results are shown in box 2 (spanning the second panel, right hand side and third panel, left hand side). The r$^{'S}$ band, although somewhat less bright than the upper control band, is clearly visible in all r$^{'S}$ samples (lanes 1, 2 and 6), while all other lanes (RhD+, RhD−, DIIIa and negative control) are without any r$^{'S}$ band. These results confirm that the modification to the reference forward primer (shortening it by deleting the 5' 10 nucleotides) nevertheless retains r$^{'S}$ specificity.

The primer modification 2 results are shown in box 3 (third panel, centre). The r$^{'S}$ band is clearly visible in all r$^{'S}$ samples (lanes 1, 2 and 6), while all other lanes (RhD+, RhD−, DIIIa and negative control) are without any r$^{'S}$ band. These results confirm that the modification to the reference forward primer (C to G substitution to generate a single base mismatch) nevertheless retains or even increases r$^{'S}$ specificity.

The primer modification 3 results are shown in box 4 (spanning the third panel, right hand side and fourth panel, left hand side). The r$^{'S}$ band is clearly visible in all r$^{'S}$ samples (lanes 1, 2 and 6), while all other lanes (RhD+, RhD−, DIIIa and negative control) are without any r$^{'S}$ band. These results confirm that the modification to the reference forward primer (C to G substitution to generate a single base mismatch) nevertheless retains or even increases is specificity.

The inspecific forward primer in box 5 (fourth panel right hand side) exhibits positive r$^{'S}$ band presence of not only r$^{'S}$ samples, but also RhD+ and DIIIa (see lanes 3 and 5), thus confirming false positive results. There is even a faint r$^{'S}$ band visible in the RhD− sample (lane 4).

Taken together, the present results demonstrate that the reference forward primer of the present invention exhibits superior performance compared with that of the Silvy et al. RHD-for primer and that the forward primer of the present invention is tolerant to a number of sequence modifications, including a 5' truncation of 10 nucleotides (i.e. reducing the value of n in the formula X—Y—Z as defined herein) and nucleotide substitutions that result in mismatches with the target sequence (i.e. selection of $S_1$, $S_2$ and/or changes reflected in the substitution possibilities of $X_2$ and/or $Y_2$ of the formula X—Y—Z as defined herein. The present invention therefore provides, inter alia, a genus of related forward PCR primer designs that address the need for r$^{'S}$-specific amplification and mitigate the drawbacks associated with a previously-described primer.

EQUIVALENTS

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

All references, including patent documents, disclosed herein are incorporated by reference in their entirety for all purposes, particularly for the disclosure referenced herein.

The invention claimed is:

1. An oligonucleotide polymerase chain reaction (PCR) primer, the nucleotide sequence of which is of the formula:

$$X_1-Y-Z$$

wherein:
- $X_1$ is the final n nucleotides of the nucleotide sequence ATATGGAAATTTGATCATGT (SEQ ID NO: 1), wherein n is a number between 1 and 20, inclusive;
- Y is $Y_1$ or $Y_2$, wherein:
  - $Y_1$ is the nucleotide sequence $AS_1TAATS_2ATAC$ (SEQ ID NO: 2), wherein $S_1$ and $S_2$ are independently selected from G and C; and
  - $Y_2$ is a variant of $Y_1$ differing from $Y_1$ by no more than one nucleotide substitution, provided that said nucleotide substitution is not a substitution of the first A or final C of $Y_1$;
- Z is the first m nucleotides in the nucleotide sequence TAAAG, wherein m is a number between 0 and 5, inclusive, and wherein at least one nucleotide of said primer comprises a biotinylated nucleotide, a fluorescently labeled nucleotide, or a locked nucleic acid (LNA) base.

2. The primer according to claim 1, wherein $X_1$ is the nucleotide sequence of AAATTTGATCATGT (SEQ ID NO: 3) or ATGT.

3. The primer according to claim 1, wherein $Y_1$ is selected from the group consisting of: ACTAATCATAC (SEQ ID NO: 4); ACTAATGATAC (SEQ ID NO: 5); and AGTAATCATAC (SEQ ID NO: 6).

4. The primer according to claim 1, wherein m is 0.

5. The primer according to claim 1, wherein the primer is between 15 and 25 nucleotides in length.

6. The primer according to claim 1, wherein the nucleotide sequence of said primer consists of a nucleotide sequence selected from the group consisting of:

(i) AAATTTGATCATGTACTAATCATAC; (SEQ ID NO: 7)

(ii) ATGTACTAATCATAC; (SEQ ID NO: 8)

(iii) AAATTTGATCATGTACTAATGATAC; (SEQ ID NO: 9) and (iv) AAATTTGATCATGTAGTAATCATAC. (SEQ ID NO: 10)

7. The primer according to claim 1, wherein said primer is suitable for use as a forward PCR primer in a PCR amplification of a portion of the $r'^S$ allele of intron 3 of the RHD gene.

8. A plurality of oligonucleotide primers comprising:
(i) an oligonucleotide primer as defined in claim 1; and
(ii) at least one primer selected from the group consisting of:
  (a) an oligonucleotide primer of between 26 and 30 nucleotides in length comprising the nucleotide sequence GGAAAAGGTTTGAGAGGAATTATATT (SEQ ID NO: 11) or a variant thereof differing by not more than 3 nucleotide substitutions from the nucleotide sequence of SEQ ID NO: 11, provided that said substitutions do not include substitution of the final T of the nucleotide sequence of SEQ ID NO: 11;
  (b) an oligonucleotide primer consisting of the nucleotide sequence GGAAAAGGTTTGAGAGGAATTATATT (SEQ ID NO: 11);
  (c) the RHCE c forward primer consisting of the nucleotide sequence TGGGCTTCCTCACCTCAAA (SEQ ID NO: 12);
  (d) the RHCE c reverse primer consisting of the nucleotide sequence TGATGACCACCTTCCCAGG (SEQ ID NO: 13);

(e) the RHCE C forward primer consisting of the nucleotide sequence GGCCACCACCATTTGAA (SEQ ID NO: 14);
(f) the RHCE C reverse primer consisting of the nucleotide sequence GGTAGCAGGCGTCTGTAAAAA (SEQ ID NO: 15);
(g) the RHCE exon 1 forward primer consisting of the nucleotide sequence CATAGACAGGCCAGCACAG (SEQ ID NO: 16);
(h) the RHCE exon 1 reverse primer consisting of the nucleotide sequence TGCCCCTGGAGAACCAT (SEQ ID NO: 17);
(i) the RHCE exon 5 forward primer consisting of the nucleotide sequence AAATTAAAATAAGCATTTGACCATC (SEQ ID NO: 18);
(j) the RHCE exon 5 reverse primer consisting of the nucleotide sequence CCTGAGATGGCTGTCACCAC (SEQ ID NO: 19);
(k) the RHCE exon 7 forward primer consisting of the nucleotide sequence ACATGCCATTGCCGTTC (SEQ ID NO: 20); and
(l) the RHCE exon 7 reverse primer consisting of the nucleotide sequence TCTCACCTGCCAATCTGCT (SEQ ID NO: 21).

9. The plurality of oligonucleotide primers according to claim 8, wherein said primers comprise at least (i) and (ii)(a).

10. The plurality of oligonucleotide primers according to claim 9, wherein said primers comprise the primer pair:

```
                                          (SEQ ID NO: 7)
AAATTTGATCATGTACTAATCATAC;
and (SEQ ID NO: 11)
GGAAAAGGTTTGAGAGGAATTATATT.
```

11. A kit for assessing a subject's blood type, said kit comprising:
a plurality of primers as defined in claim 8;
optionally, one or more probes and/or primers that span one or more polymorphic positions in intron 3, exon 3, exon 4, intron 7 and/or exon 7 of the RHD gene locus; and
optionally, one or more probes and/or primers that span one or more polymorphic positions in exon 7 of the RHCE gene locus.

12. A system for use in determining a subject's blood type, the system comprising:
a kit as defined in claim 11; and
at least one detector arranged to detect a signal from detectably labelled DNA obtained from said subject or a detectably labelled amplicon produced by PCR amplification carried out on DNA obtained from said subject;
at least one controller in communication with the at least one detector, the controller being programmed with computer-readable instructions to transform said signal into predicted blood type haplotypes, and optionally, to transform said predicted blood type haplotypes into a predicted blood type phenotype.

13. A method for determining the presence or absence of, or for discriminating between, blood type alleles in a DNA-containing sample, which method comprises amplification by polymerase chain reaction (PCR) of at least a portion of intron 3 of the RHD gene, wherein said PCR employs at least a forward primer and a reverse primer each capable of hybridising to the portion of $r'^S$ intron 3 sequence set forth in SEQ ID NO: 31, or its complement, and wherein said forward primer is as defined in claim 1.

14. The method according to claim 13, wherein said blood type alleles are alleles that comprise an RHD/RHCE hybrid exon 3.

15. The method according to claim 13, wherein said blood type alleles are selected from the group consisting of: RHD*$r'^S$; RHD*$r'^S$-like; RHD*$r'^S$ Type 1; RHD*$r'^S$ Type 2; RHD*DIIIa; RHD*DIIIa IVS3+3100G; RHD*DIII_FN; RHD*DIVa-2; RHD*DIVa; RHD*DIII-type4; RHD*DIII-type6; RHD*DIII-type7; RHD*DIII-type8; RHCE*$ce^S$; RHCE*$ce^S$1006T; RHCE*$ce^S$1006C; RHCE*ce733G; RHCE*ce48C,733G,1025T; RHCE*ce48C,697G,733G; RHCE*ce340T,733G; and RHCE*ce48C,733G,748A.

16. The method according to claim 13, wherein said PCR amplifies $r'^S$, but does not amplify one or more of: RHD; RHCE*ce; RHD*DIIIa; RHD*DIIIa IVS3+3100G; and RHD*DIVa.

17. The method according to claim 16, wherein said PCR amplifies $r'^S$, but does not amplify any of RHD; RHCE*ce; RHD*DIIIa; RHD*DIIIa IVS3+3100G; and RHD*DIVa.

18. The method according to claim 13, wherein the nucleotide sequence of said forward primer consists of the nucleotide sequence AAATTTGATCATGTACTAATCATAC (SEQ ID NO: 7).

19. The method according to claim 13, wherein said reverse primer is of between 26 and 30 nucleotides in length and comprises the nucleotide sequence GGAAAAGGTTTGAGAGGAATTATATT (SEQ ID NO: 11).

20. The method according to claim 13, wherein the method further comprises genotyping the sample at one or more positions of single nucleotide polymorphism (SNP) in the RHD and/or RHCE gene loci.

21. The method according to claim 20, wherein the method comprises genotyping the sample at one or more of:
(i) position 410 of the RHD exon 3;
(ii) position 602 of the RHD exon 4;
(iii) position 1048 of the RHD exon 7;
(iv) position 1006 of the RHCE exon 7; and
(v) position 3100 of the RHD intron 3.

22. A method of blood matching, the method comprising:
carrying out the method according to claim 13 on a recipient sample from a recipient subject in need of donor blood and on a donor sample from a potential donor subject;
comparing the blood type alleles present in the recipient sample with those present in the donor subject and thereby determining the compatibility of the recipient subject to receive blood from the potential donor subject.

23. An oligonucleotide polymerase chain reaction (PCR) primer, the nucleotide sequence of which consists of:

```
AAATTTGATCATGTACTAATGATAC;        (SEQ ID NO: 9)
or

AAATTTGATCATGTAGTAATCATAC.        (SEQ ID NO: 10)
```

24. A plurality of oligonucleotide primers comprising:
(i) an oligonucleotide primer as defined in claim 23; and
(ii) at least one primer selected from the group consisting of:
(a) an oligonucleotide primer of between 26 and 30 nucleotides in length comprising the nucleotide sequence GGAAAAGGTTTGAGAGGAATTATATT (SEQ ID NO: 11) or a variant thereof differing by not more than 3 nucleotide substitutions from the nucleotide sequence of SEQ ID NO: 11, provided that said substitutions do not include substitution of the final T of the nucleotide sequence of SEQ ID NO: 11;
(b) an oligonucleotide primer consisting of the nucleotide sequence GGAAAAGGTTTGAGAGGAATTATATT (SEQ ID NO: 11);
(c) the RHCE c forward primer consisting of the nucleotide sequence TGGGCTTCCTCACCTCAAA (SEQ ID NO: 12);
(d) the RHCE c reverse primer consisting of the nucleotide sequence TGATGACCACCTTCCCAGG (SEQ ID NO: 13);
(e) the RHCE C forward primer consisting of the nucleotide sequence GGCCACCACCATTTGAA (SEQ ID NO: 14);
(f) the RHCE C reverse primer consisting of the nucleotide sequence GGTAGCAGGCGTCTGTAAAAA (SEQ ID NO: 15);
(g) the RHCE exon 1 forward primer consisting of the nucleotide sequence CATAGACAGGCCAGCACAG (SEQ ID NO: 16);
(h) the RHCE exon 1 reverse primer consisting of the nucleotide sequence TGCCCCTGGAGAACCAT (SEQ ID NO: 17);
(i) the RHCE exon 5 forward primer consisting of the nucleotide sequence AAATTAAAATAAGCATTTGACCATC (SEQ ID NO: 18);
(j) the RHCE exon 5 reverse primer consisting of the nucleotide sequence CCTGAGATGGCTGTCACCAC (SEQ ID NO: 19);
(k) the RHCE exon 7 forward primer consisting of the nucleotide sequence ACATGCCATTGCCGTTC (SEQ ID NO: 20); and
(l) the RHCE exon 7 reverse primer consisting of the nucleotide sequence TCTCACCTGCCAATCTGCT (SEQ ID NO: 21).

25. A method for determining the presence or absence of, or for discriminating between, blood type alleles in a DNA-containing sample, which method comprises amplification by polymerase chain reaction (PCR) of at least a portion of intron 3 of the RHD gene, wherein said PCR employs at least a forward primer and a reverse primer each capable of hybridising to the portion of $r^{rS}$ intron 3 sequence set forth in SEQ ID NO: 31, or its complement, and wherein said forward primer is as defined in claim 23.

26. An oligonucleotide polymerase chain reaction (PCR) primer, the nucleotide sequence of which is of the formula:

X—Y—Z wherein:
X is $X_1$ or $X_2$, wherein:
  $X_1$ is the final n nucleotides of the nucleotide sequence ATATGGAAATTTGATCATGT (SEQ ID NO: 1), wherein n is a number between 4 and 20, inclusive; and
  $X_2$ is a variant of $X_1$ differing by not more than one nucleotide substitution;
Y is $Y_1$ or $Y_2$, wherein:
  $Y_1$ is the nucleotide sequence $AS_1TAATS_2ATAC$ (SEQ ID NO: 2), wherein $S_1$ and $S_2$ are independently selected from G and C; and
  $Y_2$ is a variant of $Y_1$ differing from $Y_1$ by no more than one nucleotide substitution, provided that said nucleotide substitution is not a substitution of the first A or final C of $Y_1$;
Z is the first m nucleotides in the nucleotide sequence TAAAG, wherein m is a number between 0 and 5, inclusive, and wherein at least one nucleotide of said primer comprises a biotinylated nucleotide, a fluorescently labeled nucleotide, or a locked nucleic acid (LNA) base.

27. The primer according to claim 26, wherein n is a number between 5 and 20, inclusive.

* * * * *